United States Patent
Buhrlage et al.

(10) Patent No.: US 11,447,467 B2
(45) Date of Patent: Sep. 20, 2022

(54) COMPOUNDS FOR THE DEGRADATION OF STK4 AND TREATMENT OF HEMATOLOGIC MALIGNANCIES

(71) Applicant: DANA-FARBER CANCER INSTITUTE, INC., Boston, MA (US)

(72) Inventors: Sara Buhrlage, Somerville, MA (US); Kenneth C. Anderson, Wellesley, MA (US); Teru Hideshima, Brookline, MA (US); Nathanael S. Gray, Boston, MA (US); Xiaoxi Liu, Boston, MA (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 0 days.

(21) Appl. No.: 16/769,059

(22) PCT Filed: Dec. 13, 2018

(86) PCT No.: PCT/US2018/065453
§ 371 (c)(1),
(2) Date: Jun. 2, 2020

(87) PCT Pub. No.: WO2019/118728
PCT Pub. Date: Jun. 20, 2019

(65) Prior Publication Data
US 2020/0331889 A1 Oct. 22, 2020

Related U.S. Application Data

(60) Provisional application No. 62/597,973, filed on Dec. 13, 2017.

(51) Int. Cl.
*C07D 403/02* (2006.01)
*C07D 401/14* (2006.01)

(52) U.S. Cl.
CPC .................. *C07D 401/14* (2013.01)

(58) Field of Classification Search
CPC .................................... C07D 403/02
See application file for complete search history.

(56) References Cited

U.S. PATENT DOCUMENTS

| | | |
|---|---|---|
| 2012/0225857 A1 | 9/2012 | Augeri et al. |
| 2015/0291562 A1 | 10/2015 | Crew et al. |

FOREIGN PATENT DOCUMENTS

| | | | | |
|---|---|---|---|---|
| WO | 2016105518 A1 | 6/2016 | | |
| WO | WO-2016105518 A1 * | 6/2016 | ........... | C07D 471/04 |
| WO | 2016161145 A1 | 10/2016 | | |
| WO | WO-2016161145 A1 * | 10/2016 | ........... | C07D 513/04 |
| WO | 2017007612 A1 | 1/2017 | | |
| WO | 2017117474 A1 | 7/2017 | | |

* cited by examiner

*Primary Examiner* — John S Kenyon
(74) *Attorney, Agent, or Firm* — Burns & Levinson LLP; Daniel W. Clarke; Shawn P. Foley

(57) ABSTRACT

The application relates to a compound of Formula (I) which modulate the amount of STK4, a pharmaceutical composition comprising the compound, and a method of treating or preventing a disease or disorder associated with the modulation of STK4.

(I)

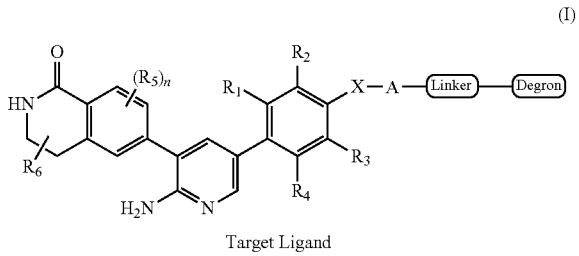

Target Ligand

20 Claims, 15 Drawing Sheets

COMPOUNDS FOR THE DEGRADATION OF STK4 AND TREATMENT OF HEMATOLOGIC MALIGNANCIES

RELATED APPLICATIONS

This application is a national stage application, filed under 35 U.S.C. § 371, of International Application No. PCT/US2018/065453, filed Dec. 13, 2018, which claims priority under 35 U.S.C. § 119(e) to U.S. Provisional Patent Appl. No. 62/597,973, filed on Dec. 13, 2017, the entire contents of each of which are incorporated herein by reference.

BACKGROUND OF THE APPLICATION

Hematologic malignancies, including multiple myeloma, lymphoma, and leukemia, contain pervasive DNA damage that leads to activation of a p53-independent proapoptotic network centered on relocalization of the ABL 1 kinase. Unlike normal cells, in which ABL1 kinase triggers cell death with the Hippo pathway co-activator YAP1, low levels of YAP1 in hematologic malignancies prevent nuclear ABL-induced apoptosis. YAP1 is under the control of a serine-threonine kinase, STK4/MST1. Genetic inactivation of STK4/MST1 restores YAP1 levels, triggering cell death in a large panel of hematological cancer cell lines, in vitro and in vivo.

STK4 is a serine-threonine kinase that is part of the Hippo signaling pathway. STK4 is involved in multiple cellular processes including proliferation, trafficking, apoptosis, immune response and stress response. Downregulation of STK4 with specific shRNAs has been shown to lead to a robust increase of YAP1 protein levels compared to scrambled shRNA. Inactivation of serine-threonine kinase 4 (STK4) has also been shown to restore YAP1 levels triggering cell death in vitro and in vivo demonstrating that YAP1 is under the control of STK4.

Thus, degradation of STK4 with small molecule compounds has the potential to be a treatment for cancers and other disorders. Known STK4 inhibitors have demonstrated poor kinase selectivity, cell penetration and pharmacokinetic properties. For these reasons, there is a need for novel, potent small molecule compounds capable of degrading STK4.

SUMMARY OF THE APPLICATION

The present application relates to novel compounds, which function to recruit STK4 to E3 ubiquitin ligase for degradation, and methods of preparation and uses thereof. In one embodiment, the compound is of Formula I:

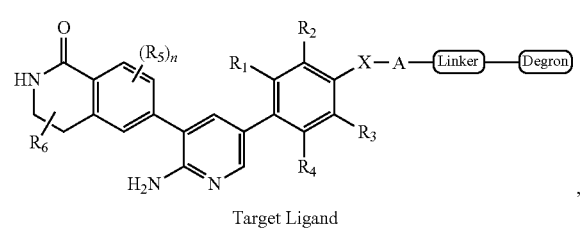

Target Ligand (I)

or an enantiomer, diastereomer, stereoisomer, or pharmaceutically acceptable salt thereof, wherein:

$R_1$, $R_2$, $R_3$, $R_4$, $R_5$, $R_6$, A, X, and n are each as defined herein;

the Targeting Ligand is capable of binding to STK4:

the Linker is a group that covalently binds to the Targeting Ligand and the Degron; and the Degron is capable of binding to a ubiquitin ligase, such as an E3 ubiquitin ligase (e.g., cereblon).

The present application also relates to targeted degradation of STK4 through the use of a compound of the present application.

The present application also relates to a pharmaceutical composition comprising a compound of the present application, or a pharmaceutically acceptable salt, hydrate, or solvate thereof, and a pharmaceutically acceptable carrier.

The present application also relates to a method of treating or preventing a disease or disorder, cancer, or hematopoietic disorder, comprising administering to a subject in need thereof an effective amount of a compound of the present application, or a pharmaceutically acceptable salt, hydrate, solvate, prodrug, stereoisomer, or tautomer thereof. In one embodiment, the disease or disorder, cancer, or hematopoietic disorder is mediated by STK4 (e.g., STK4 plays a role in the initiation or development of the disease or disorder).

The present application also relates to a method of modulating (e.g., decreasing) the amount of STK4 and/or modulating (e.g., increasing) the amount of YAP1, comprising administering to a subject in need thereof an effective amount of a compound of the present application, or a pharmaceutically acceptable salt, hydrate, solvate, prodrug, stereoisomer, or tautomer thereof.

Another aspect of the application relates to a compound of the present application, or a pharmaceutically acceptable salt, hydrate, solvate, prodrug, stereoisomer, or tautomer thereof, for treating or preventing a disease or disorder, cancer, or hematopoietic disorder.

Another aspect of the application relates to use of a compound of the present application, or a pharmaceutically acceptable salt, hydrate, solvate, prodrug, stereoisomer, or tautomer thereof, in the treatment or prevention of a disease or disorder, cancer, or hematopoietic disorder.

Another aspect of the application relates to use of a compound of the present application, or a pharmaceutically acceptable salt, hydrate, solvate, prodrug, stereoisomer, or tautomer thereof, in the manufacture of a medicament for the treatment or prevention of a disease or disorder, cancer, or hematopoietic disorder.

Another aspect of the application relates to a compound of the present application, or a pharmaceutically acceptable salt, hydrate, solvate, prodrug, stereoisomer, or tautomer thereof, for use in the treatment or prevention of a disease or disorder, cancer, or hematopoietic disorder.

Another aspect of the application relates to a compound of the present application, or a pharmaceutically acceptable salt, hydrate, solvate, prodrug, stereoisomer, or tautomer thereof, for use in the manufacture of a medicament for the treatment or prevention of a disease or disorder, cancer, or hematopoietic disorder.

Another aspect of the application relates to a compound of the present application, or a pharmaceutically acceptable salt, hydrate, solvate, prodrug, stereoisomer, or tautomer thereof, for modulating (e.g., decreasing) the amount of STK4 and/or modulating (e.g., increasing) the amount of YAP1.

Another aspect of the application relates to use of a compound of the present application, or a pharmaceutically acceptable salt, hydrate, solvate, prodrug, stereoisomer, or tautomer thereof, in the modulation (e.g., decrease) of the amount of STK4 and/or modulation (e.g., increase) of the amount of YAP1.

Another aspect of the application relates to use of a compound of the present application, or a pharmaceutically acceptable salt, hydrate, solvate, prodrug, stereoisomer, or tautomer thereof, in the manufacture of a medicament for the modulation (e.g., decrease) of the amount of STK4 and/or modulation (e.g., increase) of the amount of YAP1.

Another aspect of the application relates to a compound of the present application, or a pharmaceutically acceptable salt, hydrate, solvate, prodrug, stereoisomer, or tautomer thereof, for use in the modulation (e.g., decrease) of the amount of STK4 and/or modulation (e.g., increase) of the amount of YAP1.

Another aspect of the application relates to a compound of the present application, or a pharmaceutically acceptable salt, hydrate, solvate, prodrug, stereoisomer, or tautomer thereof, for use in the manufacture of a medicament for the modulation (e.g., decrease) of the amount of STK4 and/or modulation (e.g., increase) of the amount of YAP1.

The details of the application are set forth in the accompanying description below. Although methods and materials similar or equivalent to those described herein can be used in the practice or testing of the present application, illustrative methods and materials are now described. Other features, objects, and advantages of the application will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this application belongs. All patents and publications cited in this specification are incorporated herein by reference in their entireties.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

BRIEF DESCRIPTION OF THE DRAWINGS

In FIG. 3A, MM.1S cells were cultured with 2.5 µM I-19 for indicated time period (4-24 h). Whole cell lysates were subjected to Western blotting using anti-STK4 and anti-GAPDH antibodies. In FIG. 3B, MM.1S cells were cultured with 10 µM I-17 or I-10 for indicated time period (4-24 h). Whole cell lysates were subjected to Western blotting using anti-STK4, anti-IKZF1, and anti-GAPDH antibodies.

In FIG. 12A, whole cell lysates from MM.1S cells sensitive or resistant to lenalidomide (Len-R #1 and #2) were subjected to Western blotting using anti-CRBN and anti-GAPDH antibodies. In FIG. 12B, MM.1S cells resistant to lenalidomide (Len-R #1) were cultured with I-7 or I-10 (0.2-20 µM) for 72 h. Cell growth was determined by MTT assay.

In FIG. 14A, MM.1S cells were infected with lentiviral shRNA constructs (non-targeted control, STK4-sh #1, #2, #3 and #5). Cell viability was measured at Day 3, 5 and 7 after infection. In FIG. 14B, control and STK4 shRNA-infected MM.1S cells were harvested 3 days after infection. Whole cell lysates were subjected to Western blotting using indicated antibodies.

DETAILED DESCRIPTION OF THE APPLICATION

Compounds of the Application

Figure 1:
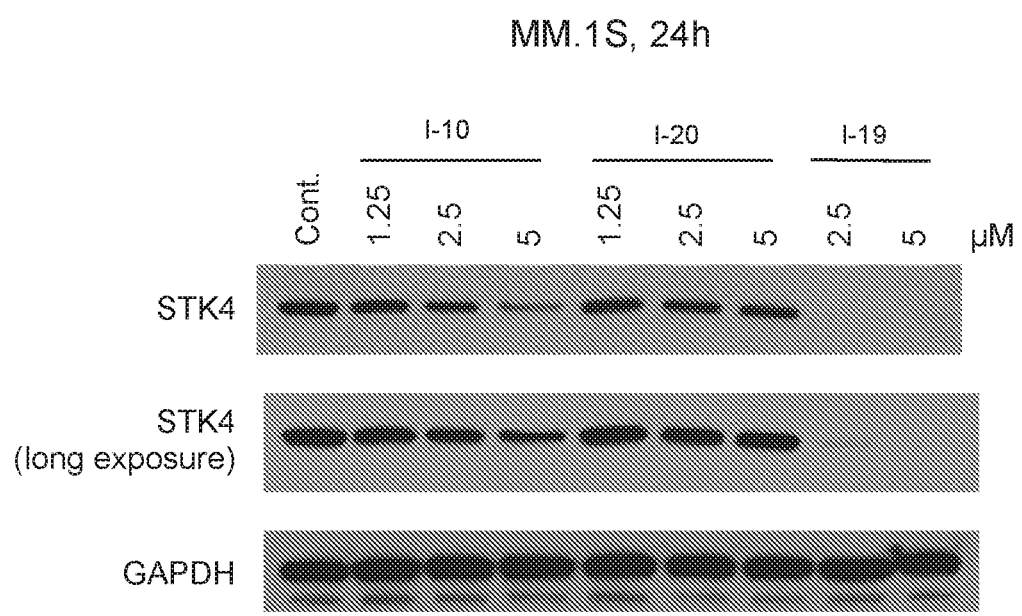
FIG. 1 shows dose dependent downregulation of STK4 in MM.1S cells by I-10, I-20, and I-19. MM.1S cells were cultured for 24 h in the presence of I-10, I-20, or I-19 at indicated concentrations. Whole cell lysates were subjected to immunoblotting using anti-STK4 and anti-GAPDH antibodies.
Figure 2:
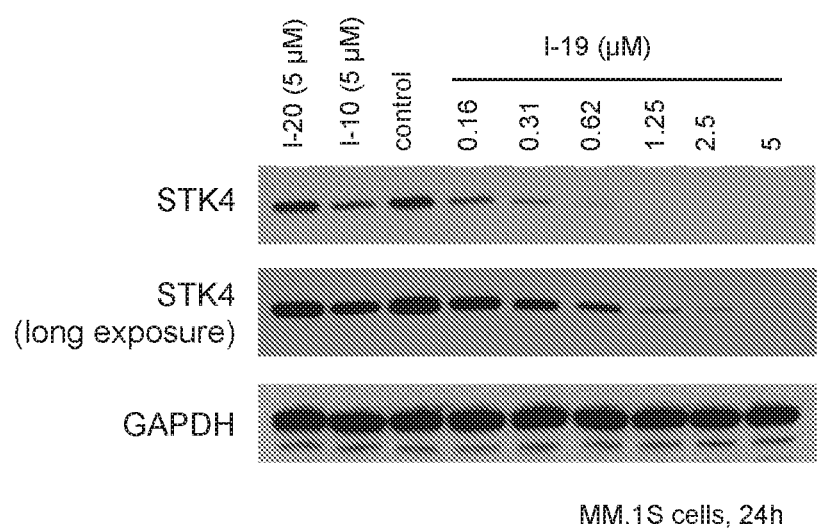
FIG. 2 shows dose dependent downregulation of STK4 in MM.1S cells by I-19. MM.1S cells were cultured for 24 h in the presence of I-20, I-10, or I-19 at indicated concentrations (0.15-5 µM). Whole cell lysates were subjected to Western blotting using anti-STK4 and anti-GAPDH antibodies.
Figure 3A:
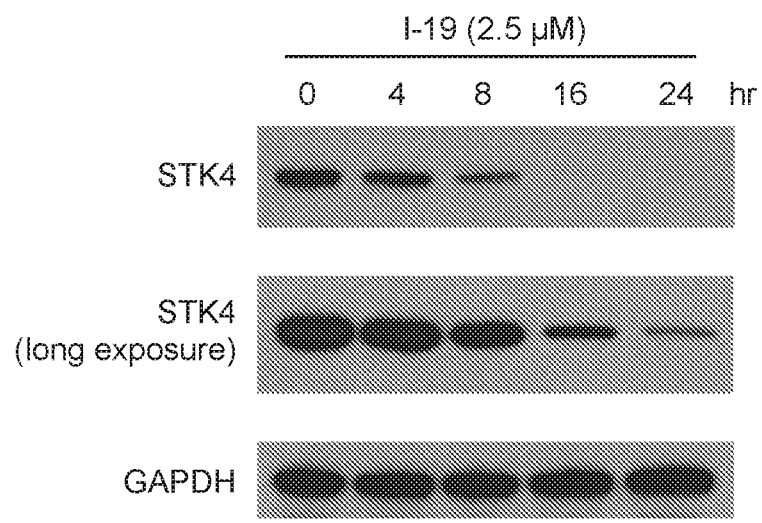
FIG. 3A and FIG. 3B show downregulation of STK4 by compounds of the application in a time-dependent fashion.
Figure 3B:
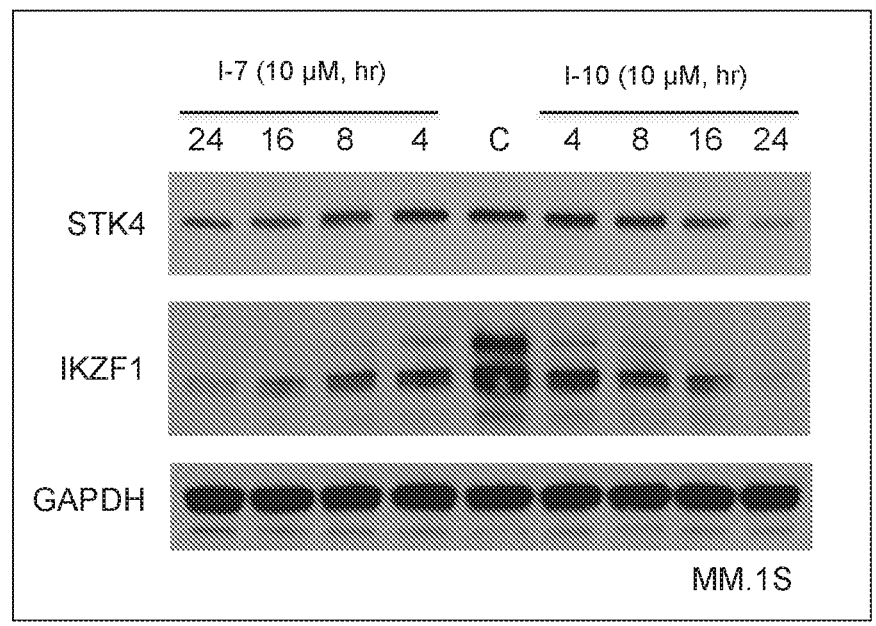
Figure 4:
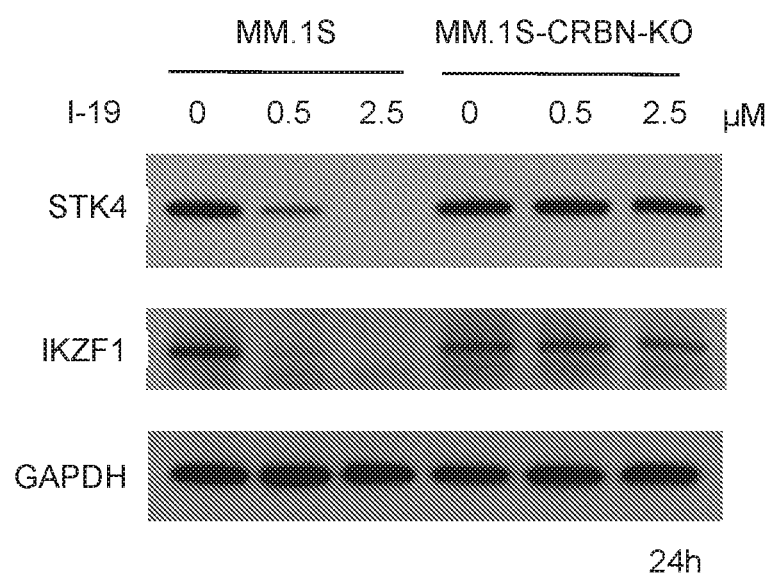
FIG. 4 shows the absence of degradation of STK4 in cereblon-knockout cells treated with I-19. Parental and cereblon (CRBN)—knockout MM.1S cells were cultured for 24 h in the presence of I-19 at indicated concentrations. Whole cell lysates were subjected to Western blotting using anti-STK4, anti-IKZF1, and anti-GAPDH antibodies.
Figure 5:
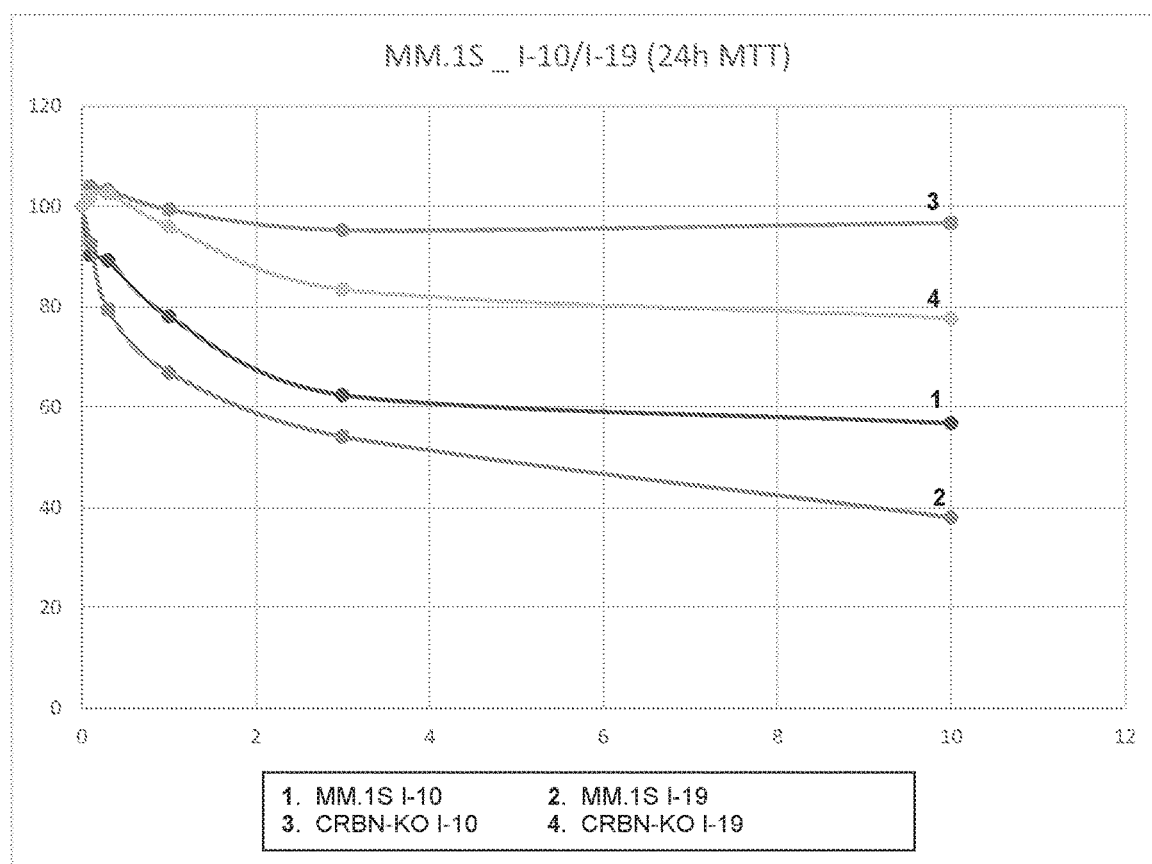
FIG. 5 shows decrease in cytotoxicity induced by I-10 or I-19 in CRBN-knockout cells. Parental or CRBN-knockout MM.1S cells were cultured for 24 h in the presence of I-10 or I-19 at indicated concentrations (0.1-10 µM). Cell growth was determined by MTT assay.
Figure 6:
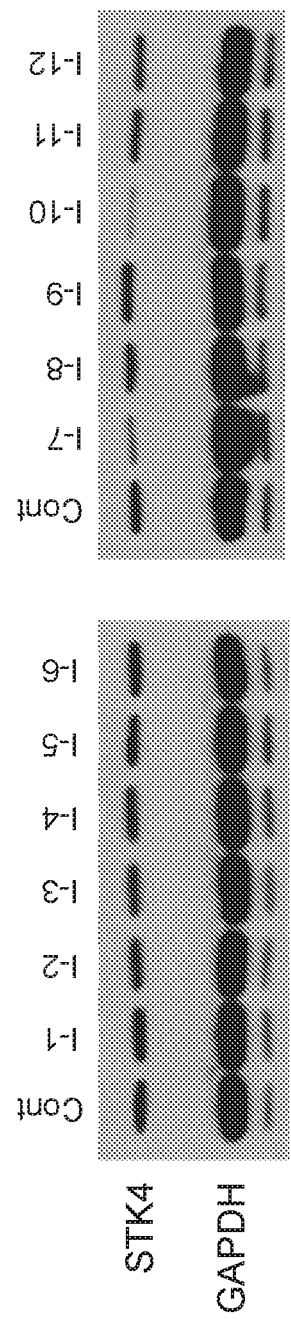
FIG. 6 shows level of STK4 downregulation by compounds I-1-I-12. MM.1S cells were cultured for 24 h in the presence of compounds I-1-I-12 (10 µM). Whole cell lysates were subjected to immunoblotting using anti-STK4 and anti-GAPDH antibodies.
Figure 7:
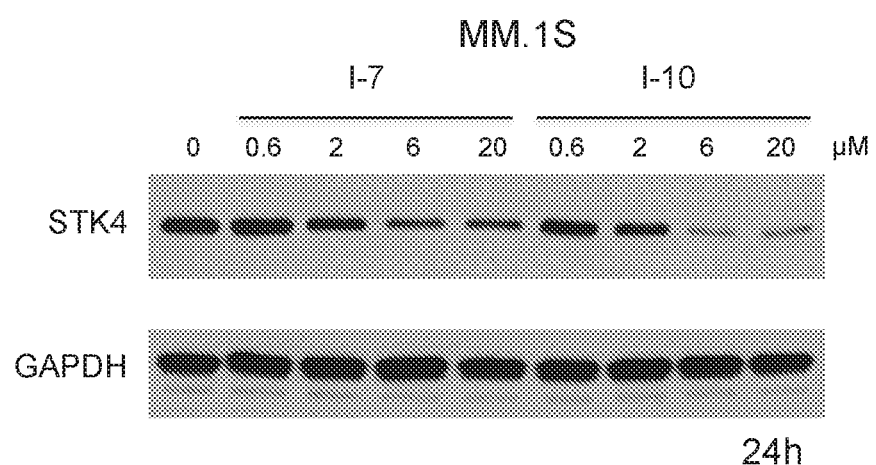
FIG. 7 shows dose dependent downregulation of STK4 in MM.1S cells by I-7 or I-10. MM.1S cells were cultured for 24 h in the presence of I-7 or I-10 at indicated concentrations (0.6-20 µM). Whole cell lysates were subjected to Western blotting using anti-STK4 and anti-GAPDH antibodies.
Figure 8:
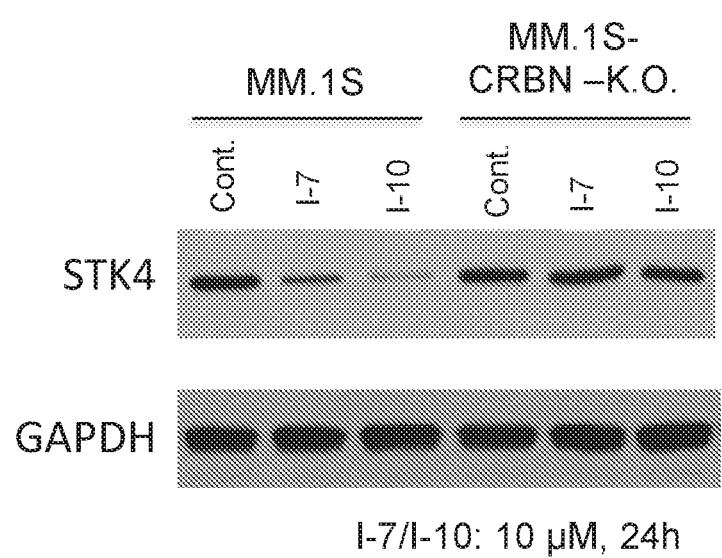
FIG. 8 shows the absence of degradation of STK4 in cereblon-knockout cells treated with I-7 or I-10. Parental and cereblon knockout (CRBN-K.O.) MM.1S cells were cultured for 24 h in the presence of I-7 or I-10. Whole cell lysates were subjected to Western blotting using anti-STK4 and anti-GAPDH antibodies.
Figure 9:
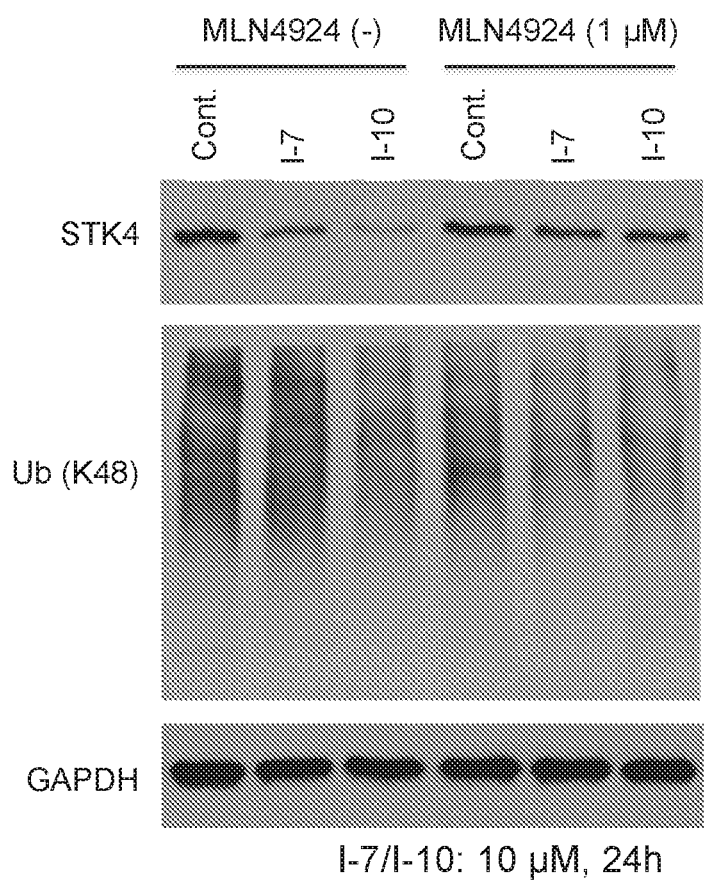
FIG. 9 shows the absence of degradation of STK4 in cells treated with I-7 or I-10 in the presence of MLN4924. MM.1S cells were cultured with I-7 or I-10 (10 µM) in the presence or absence of a NEDD8 (neural precursor cell expressed developmentally downregulated protein 8) inhibitor MLN4924 (1 µM) for 24 h. Whole cell lysates were subjected to Western blotting using anti-STK4, anti-Ub (lysine 48), and anti-GAPDH antibodies.
Figure 10:
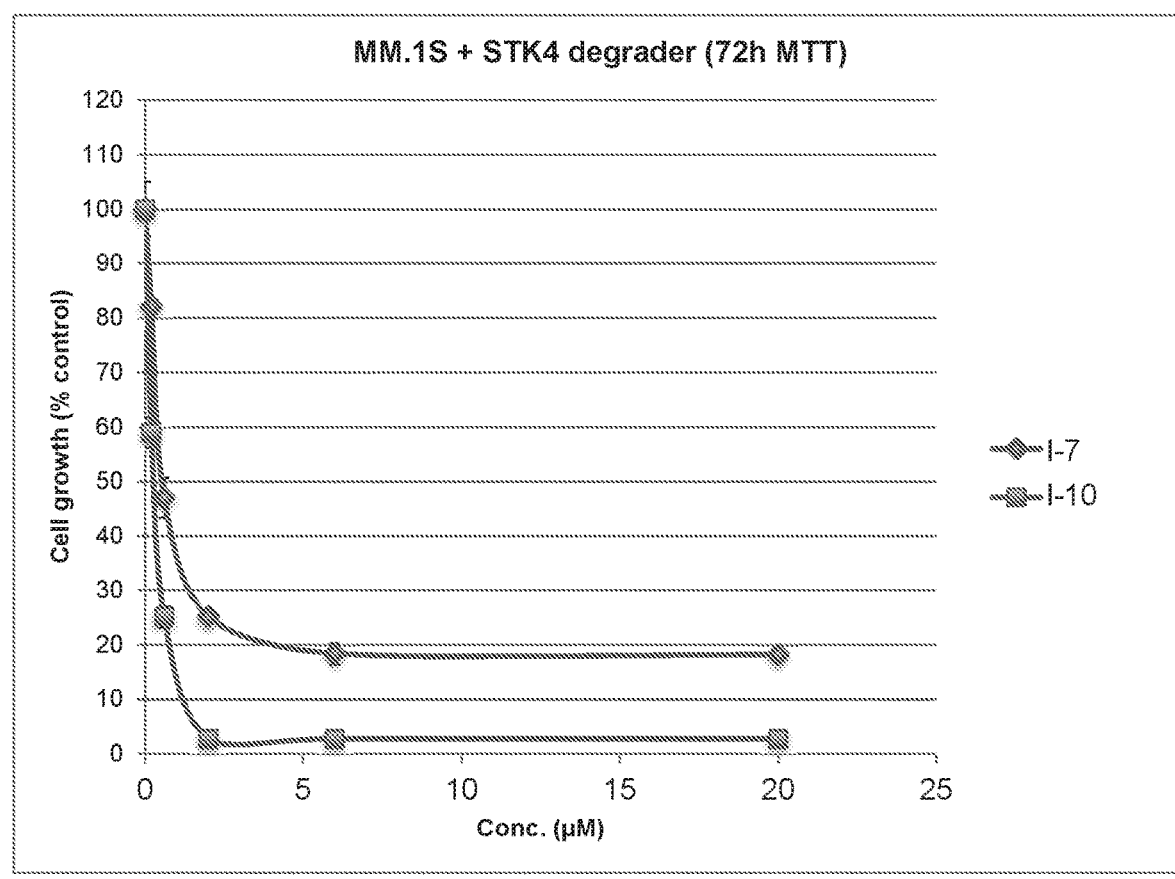
FIG. 10 shows potent MM cell growth inhibition by I-7 or I-10. MM.1S cells were cultured with I-7 or I-10 (0.2-20 µM) for 72 h. Cell growth was determined by MTT assay.
Figure 11:
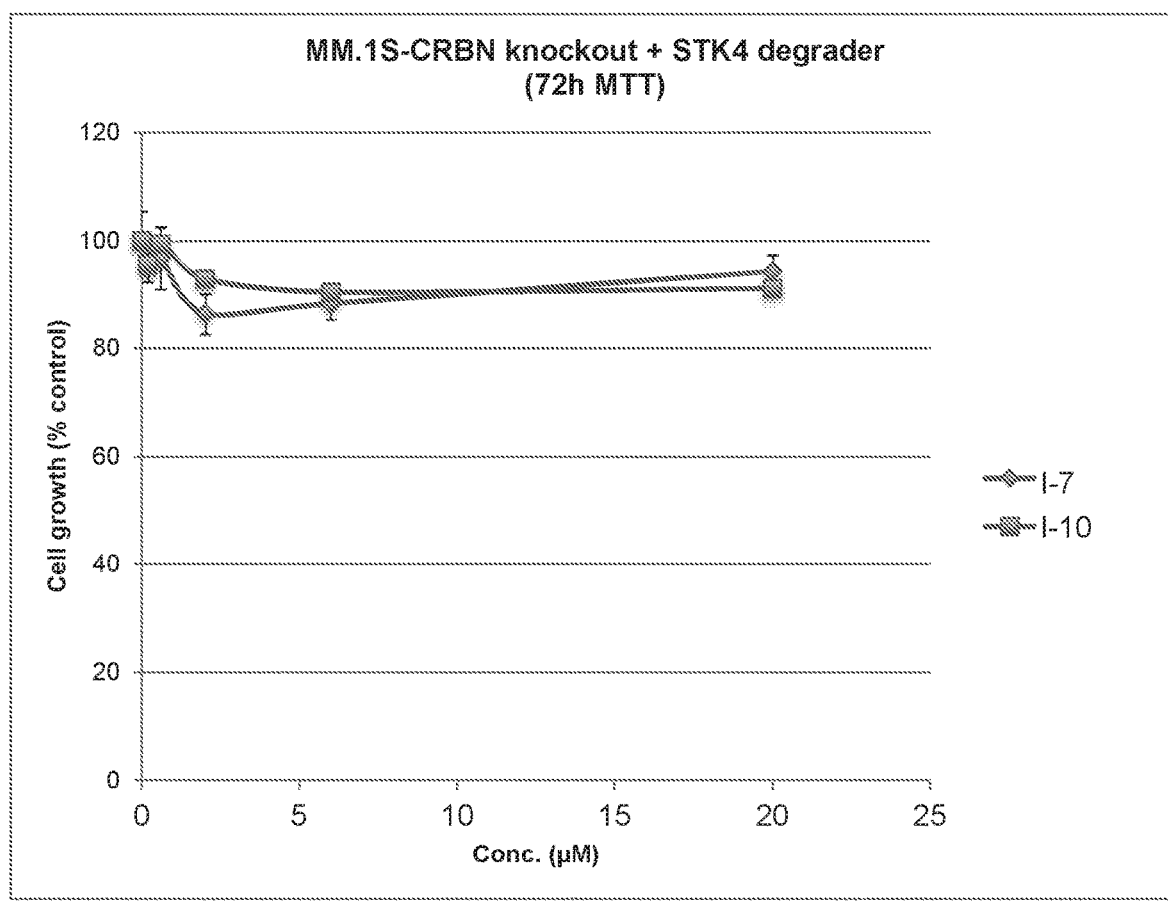
FIG. 11 shows decrease in cytotoxicity induced by I-7 or I-10 in CRBN-knockout cells. MM.1S cells were cultured with I-7 or I-10 (0.2-20 µM) for 72 h. Cell growth was determined by MT assay.
Figure 12A:
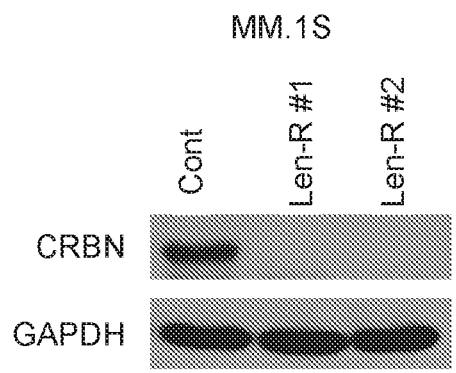
FIG. 12A and FIG. 12B show decrease in cytotoxicity induced by I-7- or I-10 in acquired lenalidomide-resistant cells.
Figure 12B:
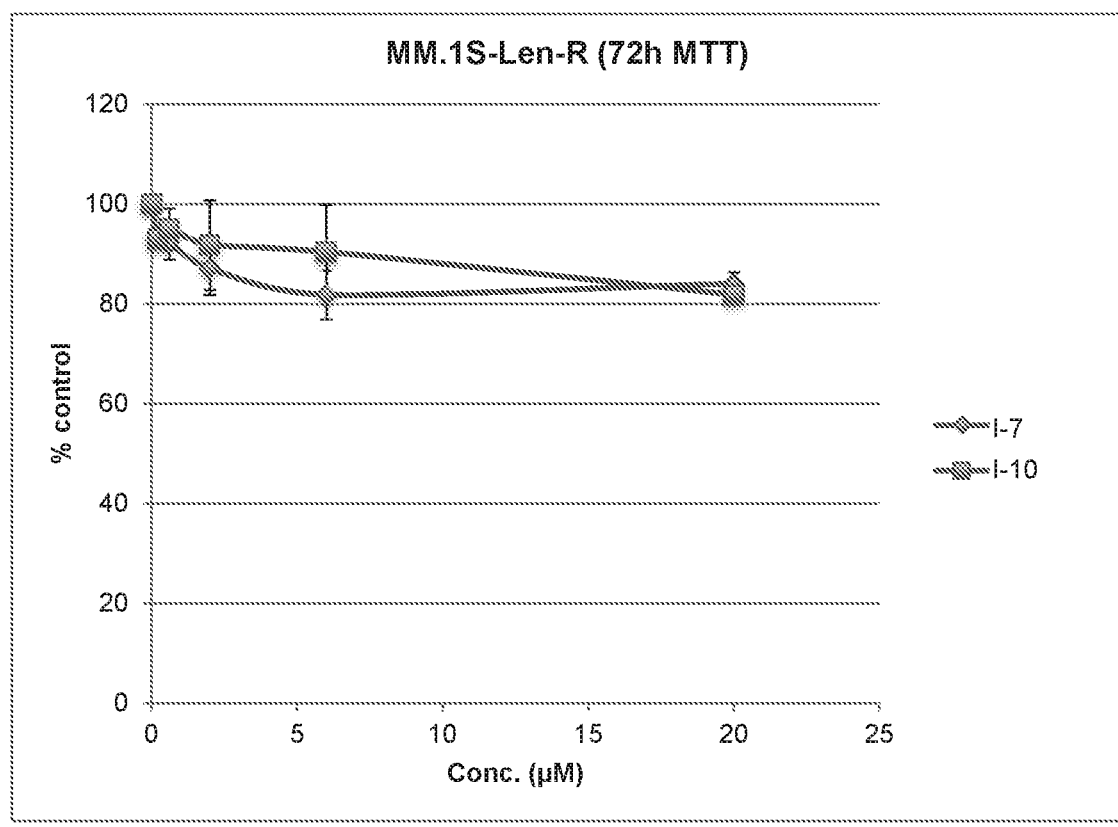
Figure 13A:
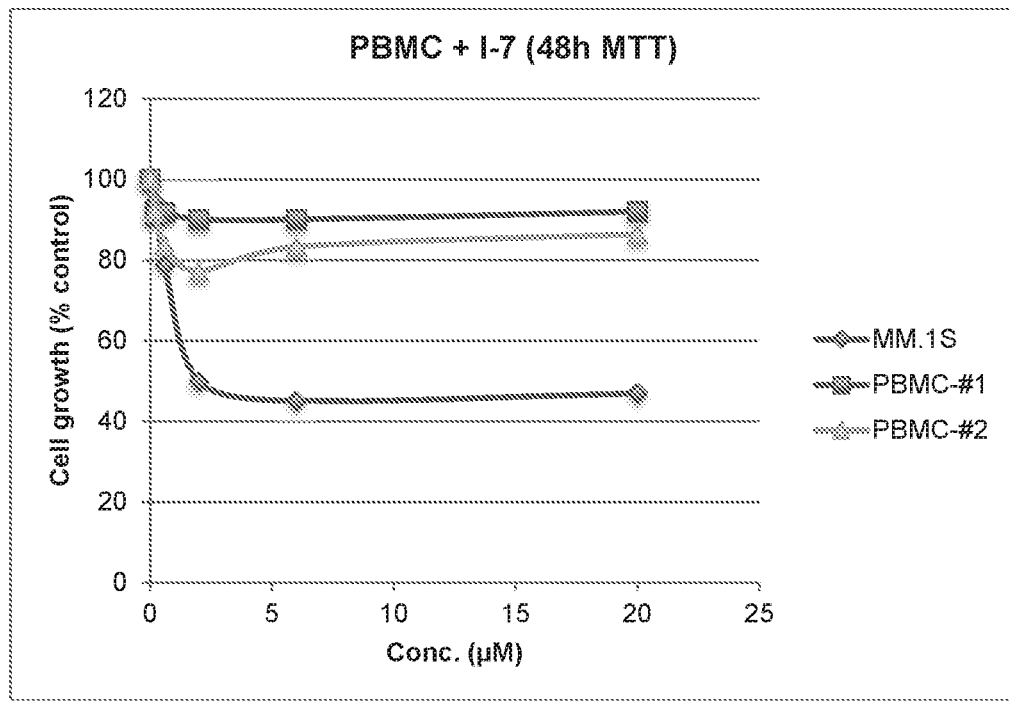
FIG. 13A and FIG. 13B show absence of cytotoxic to peripheral blood mononuclear cells induced by I-7 and I-10. Peripheral blood mononuclear cells (PBMCs) from healthy volunteer and MM.1S cells were cultured with I-7 (FIG. 13A) or I-10 (FIG. 13B) for 48 h. Cell growth was determined by MTT assay.
Figure 13B:
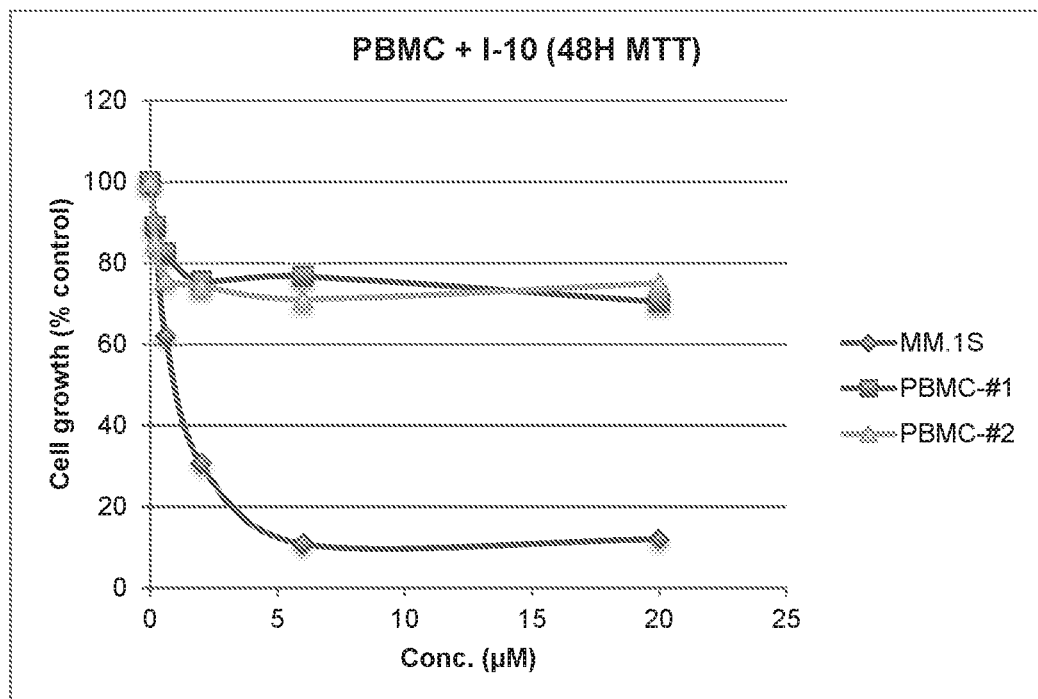
Figure 14A:
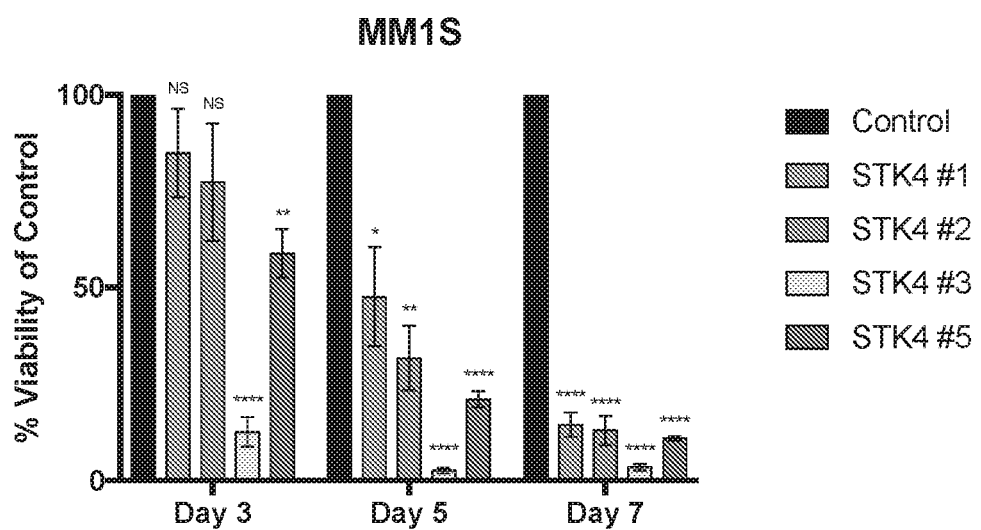
FIG. 14A and FIG. 14B show that STK4 knockdown is cytotoxic in MM cells.
Figure 14B:
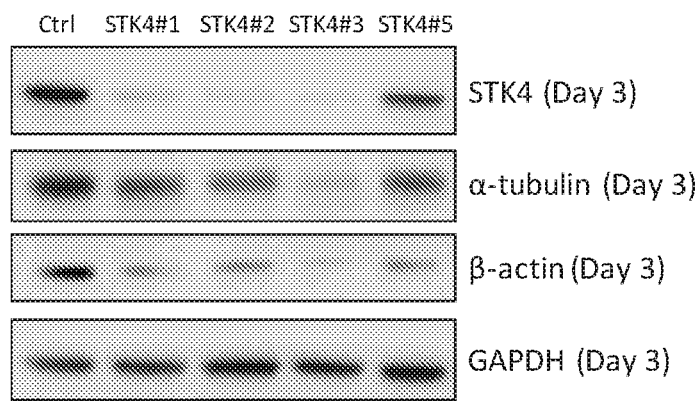
Figure 15:
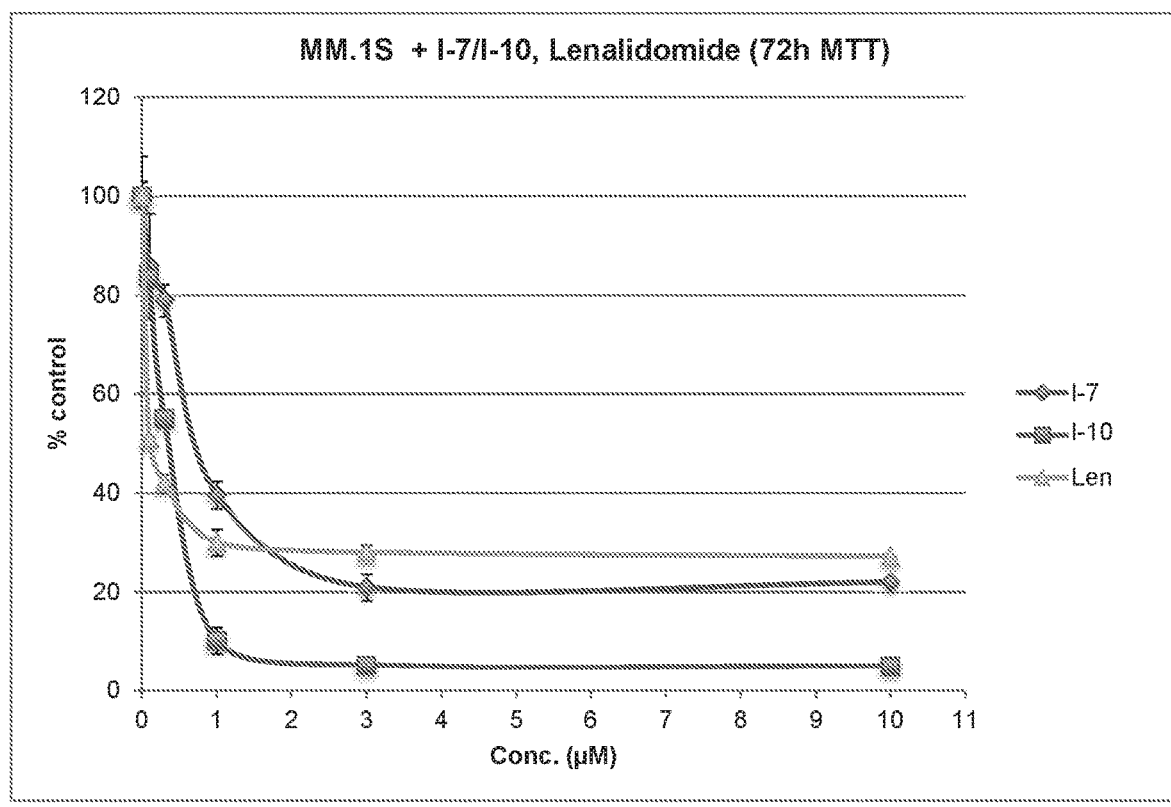
FIG. 15 shows greater potency of I-7 and I-10 in inhibiting MM cell growth as compared to lenalidomide. MM.1S cells were cultured with I-7, I-10, or lenalidomide (Len) for 72 h. Cell growth was assessed by MTT assay.

The present application relates to compounds having utility as modulators of ubiquitination and proteosomal degradation of STK4, especially compounds comprising a moiety capable of binding to STK4 that is degraded and/or otherwise inhibited by the compounds of the present application. In particular, the present application is directed to compounds which contain a moiety. e.g., a small molecule moiety (i.e., having a molecular weight of below 2,000, 1,000, 500, or 200 Daltons), such as a thalidomide-like moiety, which is capable of binding to an E3 ubiquitin ligase, such as cereblon, and a ligand that is capable of binding to STK4, in such a way that STK4 is placed in proximity to the ubiquitin ligase to effect degradation (and/or inhibition) of STK4.

In one embodiment, the present application provides a compound of Formula I:

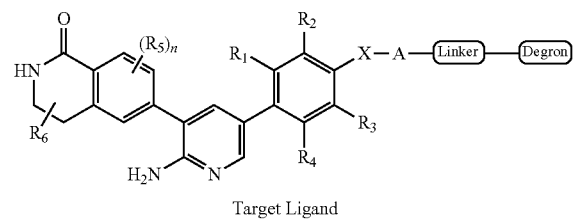

(I)

Target Ligand or an enantiomer, diastereomer, stereoisomer, or pharmaceutically acceptable salt thereof, wherein:

$R_1$, $R_2$, $R_3$, $R_4$, $R_5$, $R_6$, A, X, and n are each as defined herein;

the Targeting Ligand is capable of binding to STK4;

the Linker is a group that covalently binds to the Targeting Ligand and the Degron; and the Degron is capable of binding to a ubiquitin ligase, such as an E3 ubiquitin ligase (e.g., cereblon).

The present application further relates to a Degron of Formula DL

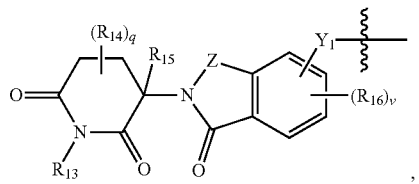

(D1)

or an enantiomer, diastereomer, or stereoisomer thereof, wherein $Y_1$, Z $R_3$, $R_{14}$, $R_{15}$, $R_{16}$, v, and q are each as defined herein.

The present application further relates to a Linker of Formula L0:

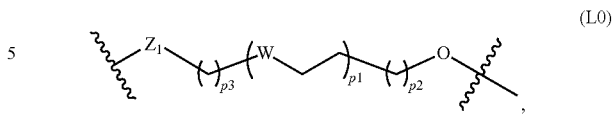

(L0)

or an enantiomer, diastereomer, or stereoisomer thereof, wherein p1, p2, p3, W, Q, and $Z_1$ are each as defined herein, the Linker is covalently bonded to a Degron via the ⟶ next to Q, and covalently bonded to a Targeting Ligand via the ⟶ next to $Z_1$.

Targeting Ligand

A Targeting Ligand (TL) (or target protein moiety or target protein ligand or ligand) is a small molecule which is capable of binding to STK4. In one embodiment, the Targeting Ligand is a compound of Formula TL-I or TL-Ia:

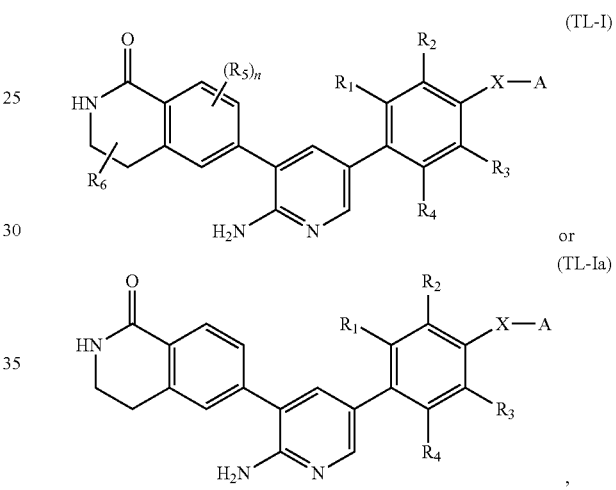

or an enantiomer, diastereomer, stereoisomer, or pharmaceutically acceptable salt thereof, wherein:

A is phenylene, $(C_1-C_4)$ alkylene, $(C_3-C_6)$ cycloalkylene, or heterocyclylene comprising one 5- or 6-membered ring and 1 to 3 heteroatoms selected from N, O, and S, wherein the phenylene, alkylene, cycloalkylene, or heterocyclylene is optionally substituted with one or more $(C_1-C_3)$ alkyl, $(C_1-C_3)$ alkoxy, $NO_2$, $NH_2$, or halogen;

X is $NR_XS(O)_m$, $S(O)_mNR_X$, $NR_XC(O)$, $C(O)NR_X$, or $NR_X$:

$R_X$ is H, $(C_1-C_3)$ alkyl, or $(C_3-C_6)$ cycloalkyl;
$R_1$ is H, $(C_1-C_3)$ alkyl, $(C_1-C_3)$ alkoxy, $NO_2$, or halogen:
$R_2$ is H, $(C_1-C_3)$ alkyl, $(C_1-C_3)$ alkoxy, $NO_2$, or halogen;
$R_3$ is H, $(C_1-C_3)$ alkyl, $(C_1-C_3)$ alkoxy, $NO_2$, or halogen;
$R_4$ is H, $(C_1-C_3)$ alkyl, $(C_1-C_3)$ alkoxy, $NO_2$, or halogen;
each $R_5$ is independently $(C_1-C_4)$ alkyl. $C(O)NR_7R_8$, CN, OH, or halogen;
$R_6$ is H, $(C_1-C_4)$ alkyl, $(C_1-C_4)$ alkoxy, or halogen;
$R_7$ and $R_8$ are each independently H or $(C_1-C_4)$ alkyl;
m is 0, 1, or 2; and
n is 0, 1, 2, or 3, wherein the Targeting Ligand is covalently bonded to a Linker via A.

For a Targeting Ligand of Formula TL-I or TL-Ia, where applicable:

(1a) In one embodiment, A is phenylene optionally substituted with one or more $(C_1-C_3)$ alkyl (e.g., methyl, ethyl, propyl, or i-propyl), ($C_1$-$C_3$) alkoxy (e.g., $OCH_3$, $OCH_2CH_3$, $OCH_2CH_2CH_3$, or $OCH(CH_3)CH_3$), $NO_2$, $NH_2$, or halogen (e.g., F, Cl, Br, or I). In one embodiment, a Linker is covalently bonded to A at the para-position of the phenylene ring. In another embodiment, a Linker is covalently bonded to A at the meta-position of the phenylene ring.

(b) In one embodiment. A is ($C_1$-$C_4$) alkylene (e.g., methylene, ethylene, propylene, i-propylene, butylene, i-butylene, or t-butylene) optionally substituted with one or more ($C_1$-$C_3$) alkyl (e.g., methyl, ethyl, propyl, or i-propyl), ($C_1$-$C_3$) alkoxy (e.g., $OCH_3$, $OCH_2CH_3$, $OCH_2CH_2CH_3$, or $OCH(CH_3)CH_3$), $NO_2$, $NH_2$, or halogen (e.g., F, Cl, Br, or I). In a further embodiment, A is ($C_1$-$C_4$) alkylene optionally substituted with halogen (e.g., F, Cl, Br, or I). In a further embodiment, A is ($C_1$-$C_3$) alkylene (e.g., methylene, ethylene, propylene, or i-propylene) optionally substituted with one or more ($C_1$-$C_3$) alkyl (e.g., methyl, ethyl, propyl, or i-propyl), ($C_1$-$C_3$) alkoxy (e.g., $OCH_3$, $OCH_2CH_3$, $OCH_2CH_2CH_3$, or $OCH(CH_3)CH_3$), $NO_2$, $NH_2$, or halogen (e.g., F, Cl, Br, or I). In a further embodiment, A is ($C_1$-$C_3$) alkylene optionally substituted with halogen (e.g., F, Cl, Br, or I). In a further embodiment, A is ($C_2$-$C_4$) alkylene (e.g., ethylene, propylene, i-propylene, butylene, i-butylene, or t-butylene) optionally substituted with one or more ($C_1$-$C_3$) alkyl (e.g., methyl, ethyl, propyl, or i-propyl), ($C_1$-$C_3$) alkoxy (e.g., $OCH_3$, $OCH_2CH_3$, $OCH_2CH_2CH_3$, or $OCH(CH_3)CH_3$), $NO_2$. $NH_2$, or halogen (e.g., F, Cl, Br, or I). In a further embodiment, A is ($C_2$-$C_4$) alkylene optionally substituted with halogen (e.g., F, Cl, Br, or I). In a further embodiment, A is propylene.

(1c) In one embodiment, A is ($C_3$-$C_6$) cycloalkylene (e.g., cyclopropylene, cyclobutylene, cyclopentylene, or cyclohexylene) optionally substituted with one or more ($C_1$-$C_3$) alkyl (e.g., methyl, ethyl, propyl, or i-propyl), ($C_1$-$C_3$) alkoxy (e.g., $OCH_3$, $OCH_2CH_3$, $OCH_2CH_2CH_3$, or $OCH(CH_3)CH_3$), $NO_2$, $NH_2$, or halogen (e.g., F, Cl, Br, or I).

(1d) In one embodiment. A is heterocyclylene comprising one 5- or 6-membered ring and 1 to 3 heteroatoms selected from N, O, and S, optionally substituted with one or more ($C_1$-$C_3$) alkyl (e.g., methyl, ethyl, propyl, or i-propyl). ($C_1$-$C_3$) alkoxy (e.g., $OCH_3$, $OCH_2CH_3$, $OCH_2CH_2CH_3$, or $OCH(CH_3)CH_3$), $NO_2$, $NH_2$, or halogen (e.g., F, Cl, Br, or I). In a further embodiment, the heterocyclylene comprises a 5- or 6-membered ring and 1 to 2 heteroatoms selected from N and O. In a further embodiment, the heterocyclylene is selected from pyrrolidinylene, imidazolidinylene, piperidinylene, piperazinylene, and morpholinylene. In a further embodiment, the heterocyclylene is piperidinylene.

(2a) In one embodiment, X is $NR_XS(O)_m$ or $S(O)_mNR_X$. In a further embodiment, X is $NR_XS$, $NR_XS(O)$, or $NR_XS(O)_2$. In one embodiment, X is $NR_XS(O)_2$. In another embodiment, X is $SNR_X$, $S(O)NR_X$, or $S(O)_2NR_X$. In a further embodiment, X is $S(O)_2NR_X$. In another embodiment, X is $NR_XS$ or $SNR_X$. In another embodiment, X is $NR_XS(O)$ or $S(O)NR_X$. In another embodiment, $NR_XS(O)_2$ or $S(O)_2NR_X$.

(2b) In one embodiment, X is $NR_XC(O)$. In another embodiment, X is $C(O)NR_X$.

(2c) In one embodiment, X is $NR_X$.

(3a) In one embodiment, $R_X$ is H.

(3b) In one embodiment, $R_X$ is ($C_1$-$C_4$) alkyl (e.g., methyl, ethyl, propyl, i-propyl, butyl, i-butyl, or tert-butyl).

(3c) In one embodiment, $R_X$ is ($C_3$-$C_6$) cycloalkyl (e.g., cyclopropyl, cyclobutyl, cyclopentyl, or cyclohexyl). In a further embodiment, $R_X$ is cyclopropyl.

(4a) In one embodiment, $R_1$ is H, halogen (e.g., F, Cl, Br, or I), or $NO_2$. In a further embodiment, $R_1$ is H. In another embodiment, $R_1$ is halogen. In a further embodiment, $R_1$ is F or Cl. In another embodiment, $R_1$ is $NO_2$.

(4b) In one embodiment, $R_1$ is H or ($C_1$-$C_3$) alkyl (e.g., methyl, ethyl, propyl, or i-propyl). In a further embodiment, $R_1$ is ($C_1$-$C_3$) alkyl. In a further embodiment, $R_1$ is methyl.

(4c) In one embodiment, $R_1$ is H or ($C_1$-$C_3$) alkoxy (e.g., $OCH_3$, $OCH_2CH_3$, $OCH_2CH_2CH_3$, or $OCH(CH_3)CH_3$). In a further embodiment, $R_1$ is ($C_1$-$C_3$) alkoxy. In a further embodiment, $R_1$ is $OCH_3$.

(5a) In one embodiment, $R_2$ is H, halogen (e.g., F, Cl, Br, or I), or $NO_2$. In a further embodiment, $R_2$ is H. In another embodiment, $R_2$ is halogen. In a further embodiment, $R_2$ is F or Cl. In another embodiment, $R_2$ is $NO_2$.

(5b) In one embodiment, $R_2$ is H or ($C_1$-$C_3$) alkyl (e.g., methyl, ethyl, propyl, or i-propyl). In a further embodiment, $R_2$ is ($C_1$-$C_3$) alkyl. In a further embodiment, $R_2$ is methyl.

(5c) In one embodiment, $R_2$ is H or ($C_1$-$C_3$) alkoxy (e.g., $OCH_3$, $OCH_2CH_3$, $OCH_2CH_2CH_3$, or $OCH(CH_3)CH_3$). In a further embodiment, $R_2$ is ($C_1$-$C_3$) alkoxy. In a further embodiment, $R_2$ is $OCH_3$.

(6a) In one embodiment, $R_3$ is H, halogen (e.g., F, Cl, Br, or I), or $NO_2$. In a further embodiment, $R_3$ is H. In another embodiment, $R_3$ is halogen. In a further embodiment, $R_3$ is F or Cl. In another embodiment. $R_3$ is $NO_2$.

(6b) In one embodiment. $R_3$ is H or ($C_1$-$C_3$) alkyl (e.g., methyl, ethyl, propyl, or i-propyl). In a further embodiment, $R_3$ is ($C_1$-$C_3$) alkyl. In a further embodiment, $R_3$ is methyl.

(6c) In one embodiment, $R_3$ is H or ($C_1$-$C_3$) alkoxy (e.g., $OCH_3$, $OCH_2CH_3$, $OCH_2CH_2CH_3$, or $OCH(CH_3)CH_3$). In a further embodiment. $R_3$ is ($C_1$-$C_3$) alkoxy. In a further embodiment, $R_3$ is $OCH_3$.

(7a) In one embodiment, $R_4$ is H, halogen (e.g., F, Cl, Br, or I), or $NO_2$. In a further embodiment, $R_4$ is H. In another embodiment, $R_4$ is halogen. In a further embodiment, $R_4$ is F or Cl. In another embodiment, $R_4$ is $NO_2$.

(7b) In one embodiment. $R_4$ is H or ($C_1$-$C_3$) alkyl (e.g., methyl, ethyl, propyl, or i-propyl). In a further embodiment, $R_4$ is ($C_1$-$C_3$) alkyl. In a further embodiment, $R_4$ is methyl.

(7c) In one embodiment. $R_4$ is H or ($C_1$-$C_3$) alkoxy (e.g., $OCH_3$, $OCH_2CH_3$, $OCH_2CH_2CH_3$, or $OCH(CH_3)CH_3$). In a further embodiment, $R_4$ is ($C_1$-$C_3$) alkoxy. In a further embodiment, $R_4$ is $OCH_3$.

(8a) In one embodiment, at least one $R_5$ is ($C_1$-$C_4$) alkyl (e.g., methyl, ethyl, propyl, i-propyl, butyl, i-butyl, or tert-butyl). In a further embodiment, at least one $R_5$ is methyl or ethyl.

(8b) In one embodiment, at least one $R_5$ is $C(O)NR_7R_8$.

(8c) In one embodiment, at least one $R_5$ is CN, OH, or halogen (e.g., F, Cl, Br, or I). In a further embodiment, at least one $R_5$ is CN. In another embodiment, at least one $R_5$ is OH. In another embodiment, at least one $R_5$ is halogen. In a further embodiment, at least one $R_5$ is F or Cl.

(9a) In one embodiment, $R_6$ is H or halogen (e.g., F, Cl, Br, or I). In a further embodiment, $R_6$ is H. In another embodiment, $R_6$ is halogen. In a further embodiment, $R_6$ is F or Cl.

(9b) In one embodiment, $R_6$ is H or ($C_1$-$C_4$) alkyl (e.g., methyl, ethyl, propyl, i-propyl, butyl, i-butyl, or tert-butyl). In a further embodiment, $R_1$ is ($C_1$-$C_4$) alkyl. In a further embodiment, $R_6$ is methyl or ethyl.

(9c) In one embodiment, $R_6$ is H or ($C_1$-$C_4$) alkoxy (e.g., $OCH_3$, $OCH_2CH_3$, $OCH_2CH_2CH_3$, $OCH(CH_3)CH_3$, $O(CH_2)_3CH_3$, $OCH_2CH(CH_3)CH_3$, or $OC(CH_3)$). In a further embodiment, $R_6$ is ($C_1$-$C_4$) alkoxy. In a further embodiment, $R_6$ is $OCH_3$ or $OCH_2CH_3$.

(10a) In one embodiment, $R_7$ is H or ($C_1$-$C_4$) alkyl (e.g., methyl, ethyl, propyl, i-propyl, butyl, i-butyl, or tert-butyl). In a further embodiment. $R_7$ is H. In a further embodiment, $R_7$ is methyl or ethyl.

(11a) In one embodiment, $R_8$ is H or ($C_1$-$C_4$) alkyl (e.g., methyl, ethyl, propyl, i-propyl, butyl, i-butyl, or tert-butyl). In a further embodiment, $R_8$ is H. In a further embodiment, $R_8$ is methyl or ethyl.

(12a) In one embodiment, m is 0, 1, or 2. In another embodiment, m is 1 or 2. In a further embodiment, m is 2.

(13a) In one embodiment, n is 0, 1, or 2. In another embodiment, n is 0 or 1. In another embodiment, n is 1 or 2. In another embodiment, n is 0.

Any of the substituents described herein for any of A, X, $R_X$, $R_1$, $R_2$, $R_3$, $R_4$, $R_5$, $R_6$, $R_7$, $R_8$, m, and n can be combined with any of the substituents described herein for one or more of the remainder of A, X, $R_X$, $R_1$, $R_2$, $R_3$, $R_4$, $R_5$, $R_6$, $R_7$, $R_8$, m, and n.

(i) In one embodiment of Formula TL-I or TL-Ia, where applicable, $R_1$, $R_2$, and $R_3$ are each H.

(ii) In one embodiment of Formula TL-I or TL-Ia, where applicable, n is 0 and $R_6$ is H.

(iii1) In one embodiment of Formula TL-I or TL-Ia, where applicable, X is as defined in (2a), and A is as defined in (1a). In a further embodiment, X is as defined in (2a), A is as defined in (1a), and $R_X$ is as defined in (3a). In a further embodiment, X is $NR_XS(O)_2$ or $S(O)_2NR_X$, and A is as defined in (1a). In a further embodiment, X is $NR_XS(O)_2$ or $S(O)_2NR_X$, A is as defined in (1a), and $R_X$ is as defined in (3a).

(iii2) In one embodiment of Formula TL-I or TL-Ia, where applicable, X is as defined in (2b), and A is as defined in (1a). In a further embodiment, X is as defined in (2b), A is as defined in (1a), and $R_X$ is as defined in (3a).

(iii3) In one embodiment of Formula TL-I or TL-Ia, where applicable. X is as defined in (2c), and A is as defined in (1a). In a further embodiment, X is as defined in (2c), A is as defined in (1a), and $R_X$ is as defined in (3a).

(iv1) In one embodiment of Formula TL-1 or TL-Ia, where applicable, X is as defined in (2a), and A is as defined in (1b). In a further embodiment, X is as defined in (2a). A is as defined in (1b), and $R_X$ is as defined in (3a). In a further embodiment, X is $NR_XS(O)_2$ or $S(O)_2NR_X$, and A is as defined in (1b). In a further embodiment, X is $NR_XS(O)_2$ or $S(O)_2NR_X$, A is as defined in (1b), and $R_X$ is as defined in (3a).

(iv2) In one embodiment of Formula TL-I or TL-Ia, where applicable, X is as defined in (2b), and A is as defined in (1b). In a further embodiment, X is as defined in (2b), A is as defined in (1b), and $R_X$ is as defined in (3a).

(iv3) In one embodiment of Formula TL-I or TL-Ia, where applicable, X is as defined in (2c), and A is as defined in (1b). In a further embodiment, X is as defined in (2c), A is as defined in (1b), and $R_X$ is as defined in (3a).

(iv4) In one embodiment of Formula TL-I or TL-Ia, where applicable, X is as defined in (2a), and A is as defined in (1b). In a further embodiment, X is as defined in (2a), A is as defined in (1b), and $R_X$ is as defined in (3c). In a further embodiment, X is $NR_XS(O)_2$ or $S(O)_2NR_X$, and A is as defined in (1b). In a further embodiment, X is $NR_XS(O)_2$ or $S(O)_2NR_X$, A is as defined in (1b), and $R_X$ is as defined in (3c).

(iv5) In one embodiment of Formula TL-I or TL-Ia, where applicable, X is as defined in (2b), and A is as defined in (1b). In a further embodiment, X is as defined in (2b), A is as defined in (b), and $R_X$ is as defined in (3c).

(iv6) In one embodiment of Formula TL-I or TL-Ia, where applicable, X is as defined in (2c), and A is as defined in (1b). In a further embodiment, X is as defined in (2c), A is as defined in (1b), and $R_X$ is as defined in (3c).

(v1) In one embodiment of Formula TL-I or TL-Ia, where applicable, X is as defined in (2a), and A is as defined in (c). In a further embodiment, X is as defined in (2a), A is as defined in (1c), and $R_X$ is as defined in (3a). In a further embodiment, X is $NR_XS(O)_2$ or $S(O)_2NR_X$, and A is as defined in (1c). In a further embodiment, X is $NR_XS(O)_2$ or $S(O)_2NR_X$, A is as defined in (1c), and $R_X$ is as defined in (3a).

(v2) In one embodiment of Formula TL-I or TL-Ia, where applicable, X is as defined in (2b), and A is as defined in (1c). In a further embodiment, X is as defined in (2b), A is as defined in (1c), and $R_X$ is as defined in (3a).

(v3) In one embodiment of Formula TL-I or TL-Ia, where applicable. X is as defined in (2c), and A is as defined in (1c). In a further embodiment, X is as defined in (2c), A is as defined in (c), and $R_X$ is as defined in (3a).

(vi1) In one embodiment of Formula TL-1 or TL-Ia, where applicable, X is as defined in (2a), and A is as defined in (1d). In a further embodiment, X is as defined in (2a). A is as defined in (1d), and $R_X$ is as defined in (3a). In a further embodiment, X is $NR_XS(O)_2$ or $S(O)_2NR_X$, and A is as defined in (1d). In a further embodiment, X is $NR_XS(O)_2$ or $S(O)_2NR_X$, A is as defined in (1d), and $R_X$ is as defined in (3a).

(vi2) In one embodiment of Formula TL-I or TL-Ia, where applicable, X is as defined in (2b), and A is as defined in (1d). In a further embodiment, X is as defined in (2b), A is as defined in (1d), and $R_X$ is as defined in (3a).

(vi3) In one embodiment of Formula TL-I or TL-Ia, where applicable, X is as defined in (2c), and A is as defined in (1d). In a further embodiment, X is as defined in (2c), A is as defined in (0d), and $R_X$ is as defined in (3a).

(vii1) In one embodiment of Formula TL-I or TL-Ia, where applicable, $R_1$, $R_2$, and $R_3$ are each H, and X, A, and $R_X$ are each as defined herein above, for example, as a combination in any of (iii1)-(vi3).

(vii2) In one embodiment of Formula TL-I or TL-Ia, where applicable, $R_6$ is H, n is 0, and X, A, and $R_X$ are each as defined herein above, for example, as a combination in any of (iii1)-(vi3).

(vii3) In one embodiment of Formula TL-I or TL-Ia, where applicable, $R_1$, $R_2$, and $R_3$ are each H, $R_6$ is H, n is 0, and X, A, and $R_X$ are each as defined herein above, for example, as a combination in any of (iii)-(vi3).

Degron

A Degron serves to link a targeted protein, through a Linker and a Targeting Ligand, to a ubiquitin ligase for proteosomal degradation. In one embodiment, the Degron is capable of binding to a ubiquitin ligase, such as an E3 ubiquitin ligase. In one embodiment, the Degron is capable of binding to cereblon.

In one embodiment, the Degron is of Formula D1:

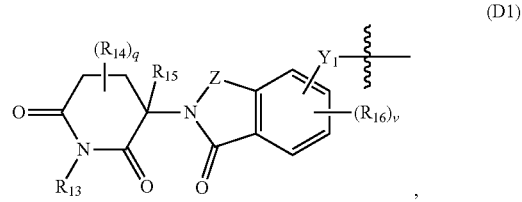

(D1)

or an enantiomer, diastereomer, or stereoisomer thereof, wherein:

$Y_1$ is a bond, $(CH_2)_{1-6}$, $(CH_2)_{0-6}$—O, $(CH_2)_{0-6}$—C(O)NR$_{11}$, $(CH_2)_{0-6}$—NR$_{11}$C(O), $(CH_2)_{0-6}$—NH, or $(CH_2)_{0-6}$—NR$_{12}$;

Z is C(O) or C(R$_{13}$)$_2$;
$R_{11}$ is H or $C_1$-$C_6$ alkyl;
$R_{12}$ is $C_1$-$C_6$ alkyl or C(O)—$C_1$-$C_6$ alkyl;
each $R_{13}$ is independently H or $C_1$-$C_3$ alkyl;
each $R_{14}$ is independently $C_1$-$C_3$ alkyl;
$R_{15}$ is H, deuterium, $C_1$-$C_3$ alkyl, F, or Cl;
each $R_{16}$ is independently halogen, OH, $C_1$-$C_6$ alkyl, or $C_1$-$C_6$ alkoxy;
q is 0, 1, or 2; and
v is 0, 1, 2 or 3,
wherein the Degron is covalently bonded to a Linker via

, wherein:

when $Y_1$ is $(CH_2)_{1-6}$—O, $Y_1$ can be bonded to the Degron via either the carbon atom or the oxygen atom, when $Y_1$ is $(CH_2)_{1-6}$—C(O)NR$_{11}$, $(CH_2)_{1-6}$—NH, or $(CH_2)_{1-6}$—NR$_{11}$, $Y_1$ can be bonded to the Degron via either the carbon atom or the nitrogen atom, and when $Y_1$ is $(CH_2)_{1-6}$—NR$_{11}$C(O), $Y_1$ can be bonded to the Degron via either the carbon atom in the CH$_2$ moiety or the carbon atom in the C(O) moiety.

In one embodiment, Z is C(O).

In one embodiment, Z is C(R$_{13}$)$_2$; and each $R_{13}$ is H. In one embodiment, Z is C(R$_{13}$)$_2$; and one of $R_{13}$ is H, and the other $R_{13}$ is $C_1$-$C_3$ alkyl selected from methyl, ethyl, and propyl. In one embodiment, Z is C(R$_{13}$)$_2$; and each $R_{13}$ is independently selected from methyl, ethyl, and propyl.

In one embodiment, $Y_1$ is a bond, O, or NH.
In one embodiment, $Y_1$ is a bond.
In one embodiment, $Y_1$ is O or NH.
In one embodiment, $Y_1$ is $(CH_2)_1$, $(CH_2)_2$, $(CH_2)_3$, $(CH_2)_4$, $(CH_2)_5$, or $(CH_2)_6$. In one embodiment, $Y_1$ is $(CH_2)_1$, $(CH_2)_2$, or $(CH_2)_3$. In one embodiment, $Y_1$ is $(CH_2)_1$ or $(CH_2)_2$.

In one embodiment, $Y_1$ is O, $CH_2$—O, $(CH_2)_2$—O, $(CH_2)_3$—O, $(CH_2)_4$—O, $(CH_2)_5$—O, or $(CH_2)_6$—O. In one embodiment, $Y_1$ is O, $CH_2$—O, $(CH_2)_2$—O, or $(CH_2)_3$—O. In one embodiment, $Y_1$ is O or $CH_2$—O. In one embodiment, $Y_1$ is O.

In one embodiment, $Y_1$ is C(O)NR$_{11}$, $CH_2$—C(O)NR$_{11}$, $(CH_2)_2$—C(O)NR$_{11}$, $(CH_2)_3$—C(O)NR$_{11}$, $(CH_2)_4$—C(O)NR$_{11}$, $(CH_2)_5$—C(O)NR$_{11}$, or $(CH_2)$—C(O)NR$_{11}$. In one embodiment, $Y_1$ is C(O)NR$_{11}$, $CH_2$—C(O)NR$_{11}$, $(CH_2)_2$—C(O)NR$_{11}$, or $(CH_2)_3$—C(O)NR$_{11}$. In one embodiment, $Y_1$ is C(O)NR$_{11}$ or $CH_2$—C(O)NR$_{11}$. In one embodiment, $Y_1$ is C(O)NR$_{11}$.

In one embodiment, $Y_1$ is NR$_{11}$C(O), CH—NR$_{11}$C(O), $(CH_2)_2$—NR$_{11}$C(O), $(CH_2)_3$—NR$_{11}$C(O), $(CH_2)_4$—NR$_{11}$C(O), $(CH_2)_5$—NR$_{11}$C(O), or $(CH_2)_6$—NR$_{11}$C(O). In one embodiment, $Y_1$ is NR$_{11}$C(O), $CH_2$—NR$_{11}$C(O), $(CH_2)_2$—NR$_{11}$C(O), or $(CH_2)_3$—NR$_{11}$C(O). In one embodiment, $Y_1$ is NR$_{11}$C(O) or $CH_2$—NR$_{11}$C(O). In one embodiment, $Y_1$ is NR$_{11}$C(O).

In one embodiment, $R_{11}$ is H. In one embodiment, $R_{11}$ is selected from methyl, ethyl, propyl, butyl, i-butyl, t-butyl, pentyl, i-pentyl, and hexyl. In one embodiment, $R_{11}$ is $C_1$-$C_3$ alkyl selected from methyl, ethyl, and propyl.

In one embodiment, $Y_1$ is NH, $CH_2$—NH. $(CH_2)_2$—NH, $(CH_2)_3$—NH, $(CH_2)_4$—NH, $(CH_2)$—NH, or $(CH_2)_6$—NH. In one embodiment, $Y_1$ is NH, $CH_2$—NH, $(CH_2)_2$—NH, or $(CH_2)_3$—NH. In one embodiment, $Y_1$ is NH or $CH_2$—NH. In one embodiment, $Y_1$ is NH.

In one embodiment, $Y_1$ is NR$_{12}$, $CH_2$—NR$_{12}$, $(CH_2)_2$—NR$_{12}$, $(CH_2)_3$—NR$_{12}$, $(CH_2)_4$—NR$_{12}$, $(CH_2)_5$—NR$_{11}$, or $(CH_2)_6$—NR$_{12}$. In one embodiment, $Y_1$ is NR$_{12}$. $CH_2$—NR$_{12}$, $(CH_2)_2$—NR$_{12}$, or $(CH_2)_3$—NR$_{11}$. In one embodiment, $Y_1$ is NR$_{12}$ or $CH_2$—NR$_{12}$. In one embodiment, $Y_1$ is NR$_{12}$.

In one embodiment, $R_{12}$ is selected from methyl, ethyl, propyl, butyl, i-butyl, t-butyl, pentyl, i-pentyl, and hexyl. In one embodiment, $R_{12}$ is $C_1$-$C_3$ alkyl selected from methyl, ethyl, and propyl.

In one embodiment, $R_{12}$ is selected from C(O)-methyl, C(O)-ethyl, C(O)-propyl, C(O)-butyl, C(O)-i-butyl, C(O)-t-butyl, C(O)-pentyl, C(O)-i-pentyl, and C(O)-hexyl. In one embodiment, $R_{12}$ is C(O)—$C_1$-$C_3$ alkyl selected from C(O)-methyl, C(O)-ethyl, and C(O)-propyl.

In one embodiment, each $R_{13}$ is H.

In one embodiment, at least one $R_{13}$ is $C_1$-$C_3$ alkyl selected from methyl, ethyl, and propyl. In one embodiment, at least one $R_{13}$ is methyl.

In one embodiment, q is 0.
In one embodiment, q is 1.
In one embodiment, q is 2.
In one embodiment, each $R_{14}$ is independently $C_1$-$C_3$ alkyl selected from methyl, ethyl, and propyl.
In one embodiment, v is 0.
In one embodiment, v is 1.
In one embodiment, y is 2.
In one embodiment, v is 3.

In one embodiment, each $R_{16}$ is independently selected from halogen (e.g., F, Cl, Br, and I), OH, $C_1$-$C_6$ alkyl (e.g., methyl, ethyl, propyl, butyl, i-butyl, t-butyl, pentyl, i-pentyl, and hexyl), and $C_1$-$C_3$ alkoxy (e.g., methoxy, ethoxy, propoxy, butoxy, i-butoxy, t-butoxy, and pentoxy). In a further embodiment, each $R_{16}$ is independently selected from F, Cl, OH, methyl, ethyl, propyl, butyl, i-butyl, t-butyl, methoxy, and ethoxy.

In one embodiment, $R_{15}$ is H, deuterium, or $C_1$-$C_3$ alkyl. In another embodiment, $R_{15}$ is H or $C_1$-$C_3$ alkyl. In a further embodiment. $R_{15}$ is in the (S) or (R) configuration. In a further embodiment, $R_{15}$ is in the (S) configuration. In one embodiment, the compound comprises a racemic mixture of (S)-$R_{15}$ and (R)-$R_{15}$.

In one embodiment, $R_{15}$ is H.
In one embodiment, $R_{15}$ is deuterium.
In one embodiment, $R_{15}$ is $C_1$-$C_3$ alkyl selected from methyl, ethyl, and propyl. In one embodiment, $R_{15}$ is methyl.

In one embodiment, $R_{15}$ is F or Cl. In a further embodiment, $R_{15}$ is in the (S) or (R) configuration. In a further embodiment, $R_{15}$ is in the (R) configuration. In one embodiment, the compound comprises a racemic mixture of (S)-$R_{15}$ and (R)-$R_{15}$. In one embodiment, $R_{15}$ is F.

Any of the groups described herein for any of $Y_1$, Z, $R_{11}$, $R_{12}$, $R_{13}$, $R_{14}$, $R_{15}$, $R_{16}$, q and v can be combined with any of the groups described herein for one or more of the remainder of $Y_1$, Z, $R_{11}$, $R_{12}$, $R_{13}$, $R_{14}$, $R_{15}$, $R_{16}$, q and v, and may further be combined with any of the groups described herein for a Linker.

For a Degron of Formula D1:
(1) In one embodiment, Z is C(O) and $Y_1$ is $(CH_2)_{0-6}$—NR$_{11}$C(O). In a further embodiment, $Y_1$ is $(CH_2)_{0-6}$—NHC(O). In a further embodiment, $Y_1$ is NHC(O).
(2) In one embodiment, Z is C(O) and $Y_1$ is $(CH_2)_{0-6}$—NH. In a further embodiment, $Y_1$ is NH.
(3) In one embodiment, Z is C(O) and $Y_1$ is $(CH_2)_{0-6}$—O. In a further embodiment, $Y_1$ is O.

(4) In one embodiment, Z is CH$_2$ and Y$_1$ is (CH$_2$)$_{0-6}$—NR$_{11}$C(O). In a further embodiment, Y$_1$ is (CH$_2$)$_{0-6}$-NHC(O). In a further embodiment, Y$_1$ is NHC(O).
(5) In one embodiment, Z is CH$_2$ and Y$_1$ is (CH$_2$)$_{0-6}$—NH. In a further embodiment, Y$_1$ is NH.
(6) In one embodiment, Z is CH$_2$ and Y$_1$ is (CH$_2$)$_{0-6}$—O. In a further embodiment, Y$_1$ is O.
(7) In one embodiment, q and v are each 0.
(8) In one embodiment, R$_{13}$ is H and q is 0
(9) In one embodiment, R$_{15}$ is H and q is 0
(10) In one embodiment, R$_{13}$ is H and R$_{15}$ is H.
(11) In one embodiment, R$_{13}$ is H, R$_{15}$H, and q is 0.
(12) In one embodiment, R$_{13}$ is H, R$_{15}$ is H, and q and v are each 0.
(13) In one embodiment, R$_{13}$, R$_{15}$, q, and v are each as defined, where applicable, in any of (7)-(12), and Y$_1$ and Z each as defined in any of (1)-(6).

In one embodiment, a Degron of Formula D1 is of Formula D1a, D1b, D1c, D1d, D1e, D1f, D1g, D1 h, D1i, D1j, D1k, or D1l:

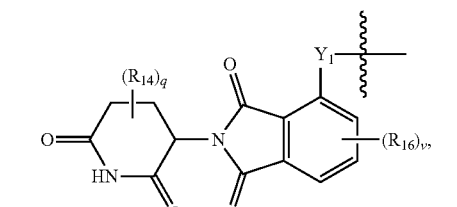
(D1a)

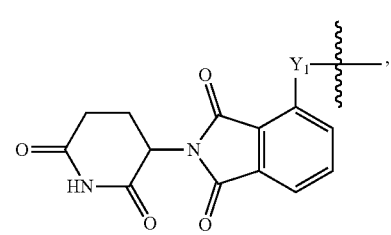
(D1b)

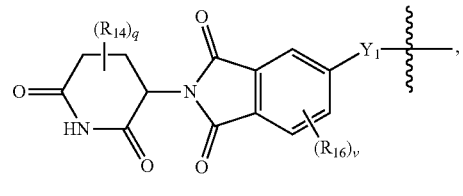
(D1c)

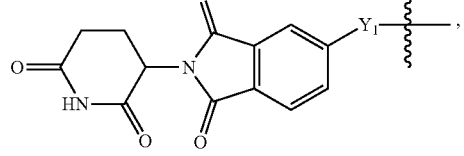
(D1d)

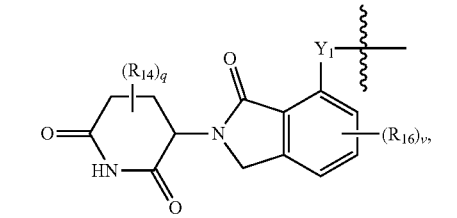
(D1e)

-continued

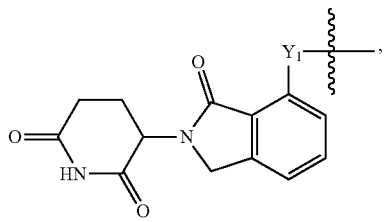
(D1f)

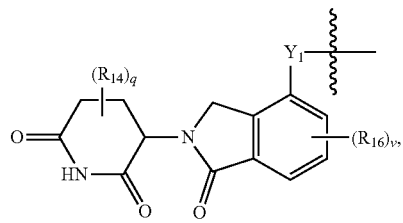
(D1g)

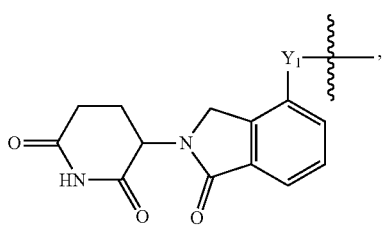
(D1h)

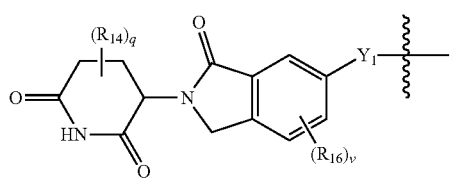
(D1i)

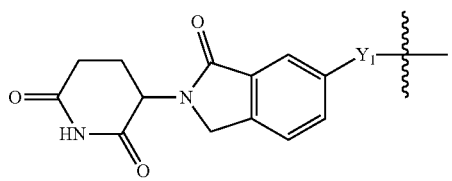
(D1j)

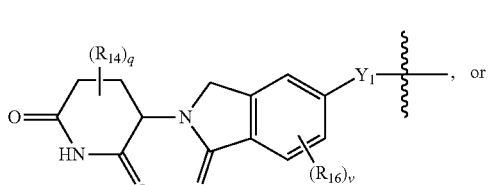
(D1k)

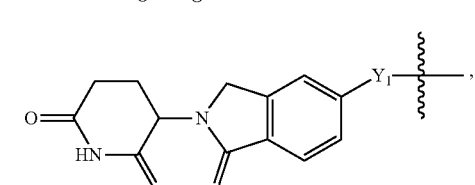
(D1l)

or an enantiomer, diastereomer, or stereoisomer thereof, wherein Y$_1$, R$_{14}$, R$_{16}$, q, and v are each as defined above in Formula D1, and can be selected from any moieties or combinations thereof described above.

In one embodiment, Y$_1$ is O or NH. In one embodiment, Y$_1$ is O. In one embodiment. Y$_1$ is NH. In one embodiment, Y$_1$ is NHC(O).

Linker

A Linker is a bond or a carbon chain that serves to link a Targeting Ligand with a Degron. In one embodiment, the carbon chain optionally comprises one, two, three, or more heteroatoms selected from N, O, and S. In one embodiment, the carbon chain comprises only saturated chain carbon atoms. In one embodiment, the carbon chain optionally comprises two or more unsaturated chain carbon atoms (e.g., C=C or C≡C). In one embodiment, one or more chain carbon atoms in the carbon chain are optionally substituted with one or more substituents (e.g., oxo, $C_1$-$C_6$ alkyl, $C_2$-$C_6$ alkenyl, $C_2$-$C_6$ alkynyl, $C_1$-$C_3$ alkoxy, OH, halogen, $NH_2$, $NH(C_1$-$C_3$ alkyl), $N(C_1$-$C_3$ alkyl)$_2$, CN, $C_3$-$C_8$ cycloalkyl, heterocyclyl, phenyl, and heteroaryl). In one embodiment, one or more chain carbon atoms in the carbon chain are optionally substituted with non-bulky substituents (e.g., oxo, $C_1$-$C_6$ alkyl, $C_2$-$C_6$ alkenyl, $C_2$-$C_6$ alkynyl, $C_1$-$C_3$ alkoxy, OH halogen, $NH_2$, $NH(C_1$-$C_3$ alkyl), $N(C_1$-$C_3$ alkyl)$_2$, and CN).

In one embodiment, the Linker comprises at least 5 chain atoms (e.g., C, O, N, and S). In one embodiment, the Linker comprises at least 10 chain atoms (e.g., C, O, N, and S). In one embodiment, the Linker comprises at least 15 chain atoms (e.g., C, O, N. and S). In one embodiment, the Linker comprises less than 20 chain atoms (e.g., C, O, N, and S). In one embodiment, the Linker comprises less than 25 chain atoms (e.g., C, O, N, and S). In one embodiment, the Linker comprises 4, 5, 6, 7, 8, 9, 10, 11, 12, 13, 14, 15, 16, 17, 18, 19, 20, 21, 22, 23, or 24 chain atoms (e.g., C, O, N. and S). In one embodiment, the Linker comprises 7, 8, 9, 10, 11, 12, 13, 14, 15, 16, 17, 18, 19, 20, 21, 22, 23, or 24 chain atoms (e.g., C, O, N, and S).

In one embodiment, the Linker is of Formula L0:

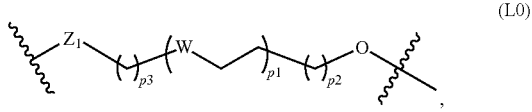

(L0)

or an enantiomer, diastereomer, or stereoisomer thereof, wherein
p1 is an integer selected from 0 to 12;
p2 is an integer selected from 0 to 12;
p3 is an integer selected from 1 to 6;
each W is independently absent, NHC(O), C(O)NH, $CH_2$, O, S, or NH;
$Z_1$ is absent, $OCH_2C(O)NH$, $CH_2C(O)NH$, OC(O)NH, C(O)NH, C(O), $CH_2$, O, or NH; and
Q is absent, $NHC(O)CH_2$, or $O(CH_2)_{0-2}$,
wherein the Linker is covalently bonded to a Degron via the ⸺ next to Q, and covalently bonded to a Targeting Ligand via the ⸺ next to $Z_1$.
wherein:
when Q is $NHC(O)CH_2$, Q can be bonded to a Degron via either the carbon atom or the nitrogen atom,
when Q is $O(CH_2)_{1-2}$, Q can be bonded to a Degron via either the carbon atom or the oxygen atom,
when $Z_1$ is $OCH_2C(O)NH$ or OC(O)NH, $Z_1$ can be bonded to a Targeting Ligand via either the oxygen atom or the nitrogen atom, and
when $Z_1$ is $CH_2C(O)NH$ or C(O)NH, $Z_1$ can be bonded to a Targeting Ligand via either the carbon atom or the nitrogen atom.

In one embodiment, the total number of chain atoms in the Linker is less than 30. In a further embodiment, the total number of chain atoms in the Linker is less than 20.

For a Linker of Formula L0:
(1) In one embodiment, p1 is an integer selected from 0 to 10.
(2) In one embodiment, p1 is an integer selected from 1 to 10.
(3) In one embodiment, p1 is an integer selected from 1 to 8.
(4) In one embodiment, p1 is an integer selected from 3 to 8.
(5) In one embodiment, p1 is selected from 1, 2, 3, 4, 5, 6, 7, and 8.
(6) In one embodiment, p1 is 1, 2, 3, or 4.
(7) In one embodiment, p1 is 3, 4, 5, 6, 7, or 8.
(8) In one embodiment, p1 is 1.
(9) In one embodiment, p1 is 3.
(10) In one embodiment, p1 is 4.
(11) In one embodiment, p1 is 5.
(12) In one embodiment, p1 is 8.
(13) In one embodiment, p2 is an integer selected from 0 to 10.
(14) In one embodiment, p2 is an integer selected from 0 to 6.
(15) In one embodiment, p2 is 0, 1, 2, 3, or 4.
(16) In one embodiment, p2 is 0.
(17) In one embodiment, p2 is 1, 2, or 3.
(18) In one embodiment, p2 is 1.
(19) In one embodiment, p2 is 2.
(20) In one embodiment, p2 is 3.
(21) In one embodiment, p3 is an integer selected from 1 to 6.
(22) In one embodiment, p3 is 1, 2, 3, or 4.
(23) In one embodiment, p3 is 1.
(24) In one embodiment, p3 is 2 or 3.
(25) In one embodiment, p3 is 2
(26) In one embodiment, p3 is 3.
(27) In one embodiment, p3 is 4.
(28) In one embodiment, each W is independently NHC(O), C(O)NH, $CH_2$, O, or NH.
(29) In one embodiment, at least one W is C(O)NH or NHC(O).
(30) In one embodiment, at least one W is $CH_2$.
(31) In one embodiment, at least one W is O.
(32) In one embodiment, at least one W is S.
(33) In one embodiment, at least one W is NH.
(34) In one embodiment, each W is O.
(35) In one embodiment, at least one W is NHC(O), and the remainder of W is/are O.
(36) In one embodiment, Q is absent or $NHC(O)CH_2$.
(37) In one embodiment, Q is absent.
(38) In one embodiment, Q is $NHC(O)CH_2$. In a further embodiment, Q is bonded to a Degron via the carbon atom.
(39) In one embodiment, Q is $O(CH_2)_0$ or $O(CH_2)_1$.
(40) In one embodiment, $Z_1$ is C(O)NH or C(O).
(41) In one embodiment, $Z_1$ is absent.
(42) In one embodiment, $Z_1$ is $OCH_2C(O)NH$.
(43) In one embodiment, $Z_1$ is $CH_2C(O)NH$.
(44) In one embodiment, $Z_1$ is OC(O)NH.
(45) In one embodiment, $Z_1$ is C(O)NH. In a further embodiment, $Z_1$ is bonded to a Targeting Ligand via the nitrogen atom.
(46) In one embodiment, $Z_1$ is C(O).
(47) In one embodiment, $Z_1$ is $CH_2$.

(48) In one embodiment, $Z_1$ is O.
(49) In one embodiment, $Z_1$ is NH.

Any of the groups described herein for any of $Z_1$, Q, W, p1, p2, and p3 can be combined with any of the groups described herein for one or more of the remainder of $Z_1$, Q, W, p1, p2, and p3, and may further be combined with any of the groups described herein for a Degron and a Targeting Ligand.

(50) In one embodiment, $Z_1$ is C(O)NH and Q is absent. In a further embodiment, $Z_1$ is bonded to a Targeting Ligand via the nitrogen atom.
(51) In one embodiment, $Z_1$ is C(O)NH and Q is NHC(O)CH$_2$. In a further embodiment, $Z_1$ is bonded to a Targeting Ligand via the nitrogen atom, and/or Q is bonded to a Degron via the carbon atom.
(52) In one embodiment, $Z_1$ is C(O)NH, Q is absent, p1 is 1, and W is NH. In a further embodiment, $Z_1$ is bonded to a Targeting Ligand via the nitrogen atom.
(53) In one embodiment, $Z_1$ is C(O)NH, Q is absent, p1 is 3, 4, 5, 6, 7, or 8, and each W is O. In a further embodiment, $Z_1$ is bonded to a Targeting Ligand via the nitrogen atom.
(54) In one embodiment, $Z_1$ is C(O)NH, Q is NHC(O)CH$_2$, p1 is 3, 4, 5, 6, 7, or 8, and each W is O. In a further embodiment, $Z_1$ is bonded to a Targeting Ligand via the nitrogen atom, and/or Q is bonded to a Degron via the carbon atom.
(55) In one embodiment, $Z_1$ is C(O)NH, Q is absent, p1 is 3, 4, 5, 6, 7, or 8, and one W is NHC(O) and the remainder of W are each O. In a further embodiment, $Z_1$ is bonded to a Targeting Ligand via the nitrogen atom.
(56) In one embodiment, $Z_1$, Q, p1, and W are each as defined, where applicable, in any of (1)-(12) and (28)-(55), and p2 is as defined in any of (13)-(20).
(57) In one embodiment, $Z_1$, Q, p1, and W are each as defined, where applicable, in any of (1)-(12) and (28)-(55), and p3 is as defined in any of (21)-(27).
(58) In one embodiment, $Z_1$, Q, p1, and W are each as defined, where applicable, in any of (50)-(52), and p2 is as defined in any of (17)-(20).
(59) In one embodiment, $Z_1$, Q, p1, and W are each as defined, where applicable, in any of (50), (51), (53), and (54), and p2 is as defined in any of (14)-(16). In a further embodiment, p2 is as defined in (16).
(60) In one embodiment, $Z_1$, Q, p1, and W are each as defined, where applicable, in any of (50)-(52), and p3 is as defined in any of (2)-(23). In a further embodiment p3 is as defined in (23).
(61) In one embodiment, $Z_1$, Q, p1, and W are each as defined, where applicable, in any of (50). (51), (53), and (54), and p3 is as defined in any of (24)-(26).

In one embodiment, the Linker of Formula L0 has the structure selected from Table L:

TABLE L

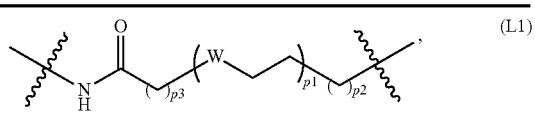
(L1)

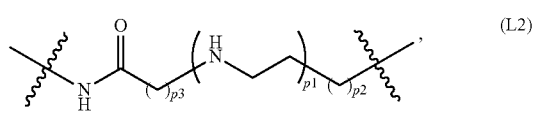
(L2)

TABLE L-continued

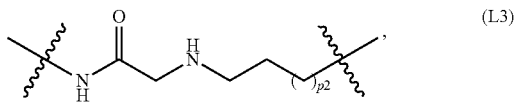
(L3)

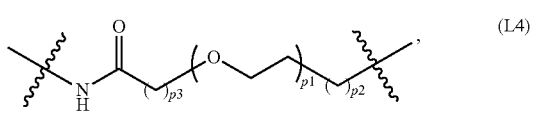
(L4)

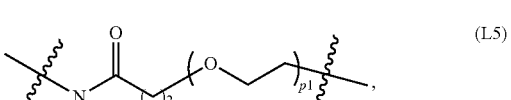
(L5)

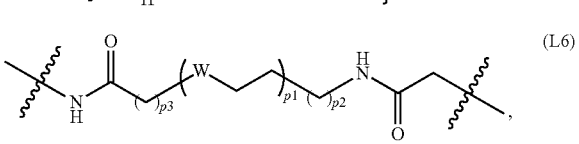
(L6)

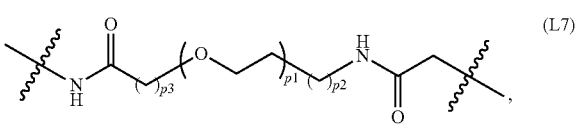
(L7)

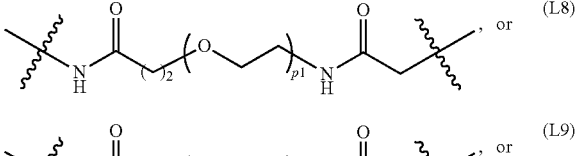
(L8)

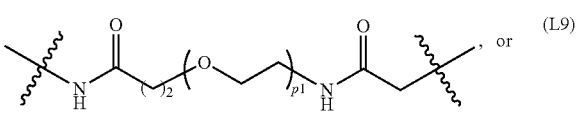
(L9)

wherein W, p1, p2, and p3 are each as described above.

Any of the Degrons described herein can be covalently bonded to any of the Linkers described herein. Any of the Targeting Ligands described herein can be covalently bonded to any of the Linkers described herein.

In one embodiment, the present application relates to a Degron-Linker (DL), wherein the Degron is of Formula D1, and the Linker is selected from L1-L9. In one embodiment, the Degron is of any of Formulae D1a-D1d, and the Linker is selected from L1-L9. In one embodiment, the Degron is of any of Formulae D1a and D1b, and the Linker is selected from L1-L9. In one embodiment, the Degron is of D1b, and the Linker is selected from L1-L9. In one embodiment, the Degron is of any of Formulae D1e-D1l, and the Linker is selected from L1-L9. In one embodiment, the Degron is of any of Formulae D1g, D1 h, D1k, and D1i, and the Linker is selected from L1-L9. In one embodiment, the Degron is of any of Formulae D1g and D1 h, and the Linker is selected from L1-L9. In one embodiment, the Degron is of Formula D1 h, and the Linker is selected from L1-L9.

In one embodiment, in any of the Degron-Linker described above, $Y_1$ is O or NH. In one embodiment, $Y_1$ is O. In one embodiment, $Y_1$ is NH. In one embodiment, $Y_1$ is NHC(O).

In one embodiment, $Y_1$ is NHC(O), and the Linker is selected from any of L1-L3.

In one embodiment, $Y_1$ is NH, and the Linker is selected from any of L4-L8.

In one embodiment, $Y_1$ is NH, and the Linker is L9.

In one embodiment, $Y_1$ is O, and the Linker is selected from any of L4-L8.

In one embodiment, $Y_1$ is O, and the Linker is L9.

In one embodiment, the Linker is designed and optimized based on SAR (structure-activity relationship) and X-ray crystallography of the Targeting Ligand with regard to the location of attachment for the Linker.

In one embodiment, the optimal Linker length and composition vary by the Targeting Ligand and can be estimated based upon X-ray structure of the Targeting Ligand bound to its target. Linker length and composition can be also modified to modulate metabolic stability and pharmacokinetic (PK) and pharmacodynamics (PD) parameters.

Non-limiting illustrative compounds of the application include:

| Compound ID | Structure |
|---|---|
| I-1 | (chemical structure) |
| I-2 | (chemical structure) |

| Compound ID | Structure |
|---|---|
| I-3 | 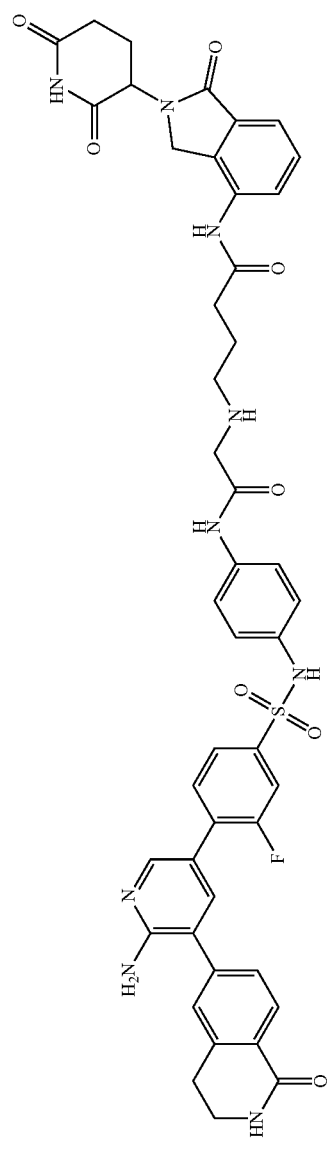 |
| I-4 | 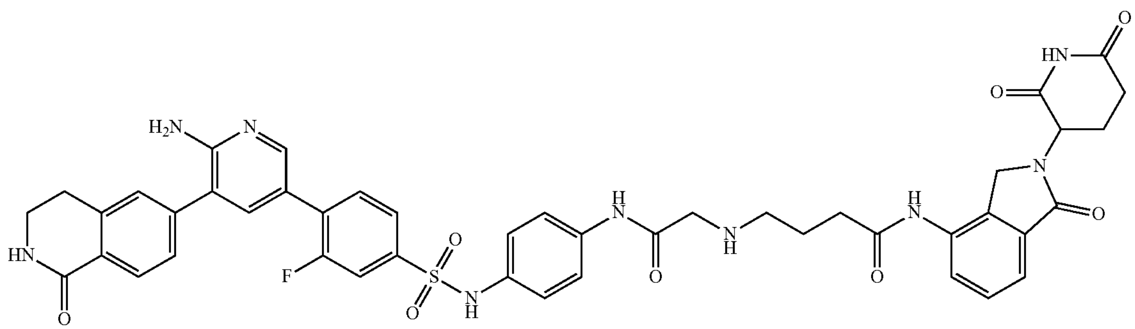 [SMILES: Nc1ncc(-c2ccc(S(=O)(=O)Nc3ccc(NC(=O)CNCCCC(=O)Nc4cccc5c4CN(C4CCC(=O)NC4=O)C5=O)cc3)cc2F)cc1-c1ccc2c(c1)CCNC2=O] |

-continued

| Compound ID | Structure |
|---|---|
| I-5 | (structure) |
| I-6 | (structure) |
| I-7 | (structure) |

-continued

| Compound ID | Structure |
|---|---|
| I-8 | 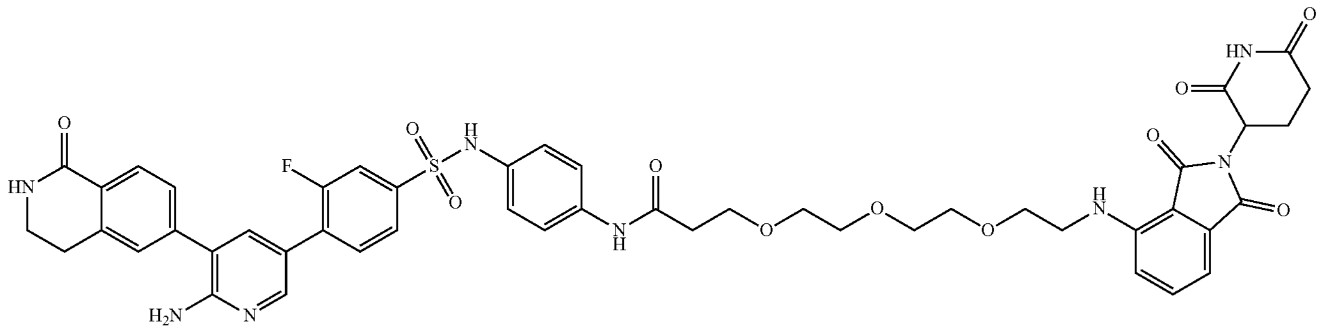 [SMILES: Nc1ncc(-c2ccc(S(=O)(=O)Nc3ccc(NC(=O)CCOCCOCCOCCNc4cccc5c4C(=O)N(C4CCC(=O)NC4=O)C5=O)cc3)cc2F)cc1-c1ccc2c(c1)CCNC2=O] |
| I-9 | 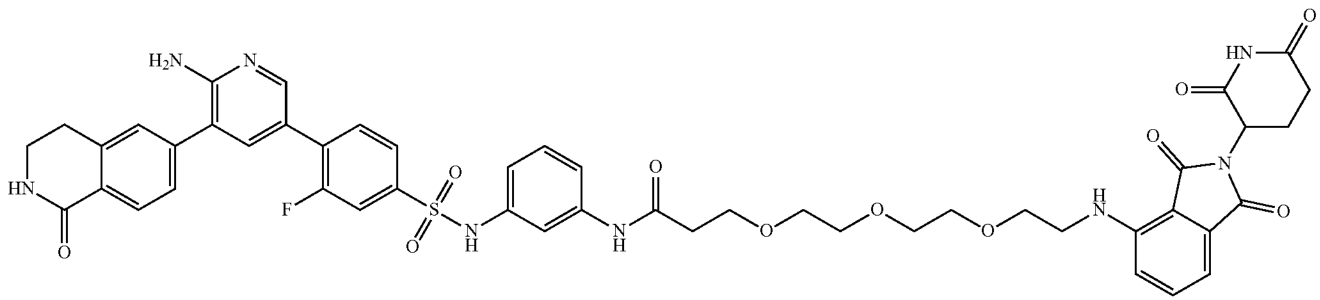 [SMILES: Nc1ncc(-c2ccc(S(=O)(=O)Nc3cccc(NC(=O)CCOCCOCCOCCNc4cccc5c4C(=O)N(C4CCC(=O)NC4=O)C5=O)c3)cc2F)cc1-c1ccc2c(c1)CCNC2=O] |
| I-10 | 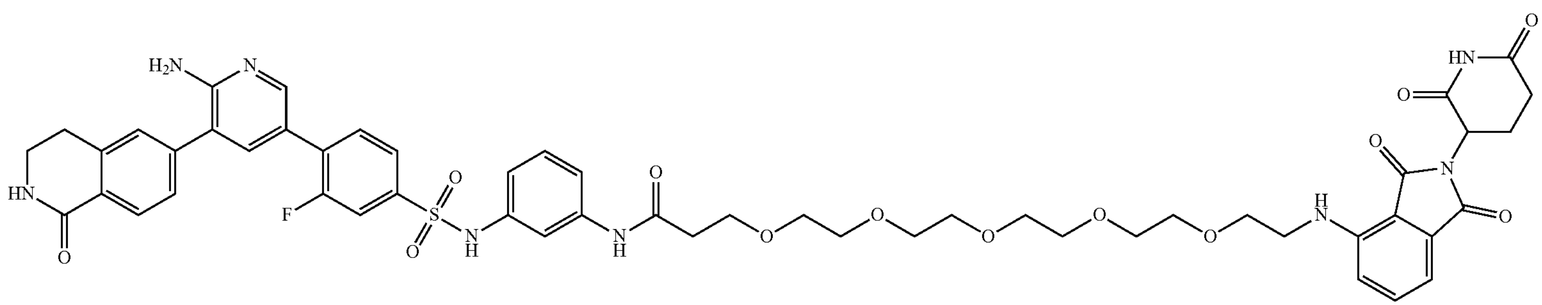 [SMILES: Nc1ncc(-c2ccc(S(=O)(=O)Nc3cccc(NC(=O)CCOCCOCCOCCOCCOCCNc4cccc5c4C(=O)N(C4CCC(=O)NC4=O)C5=O)c3)cc2F)cc1-c1ccc2c(c1)CCNC2=O] |

| Compound ID | Structure |
|---|---|
| I-11 | 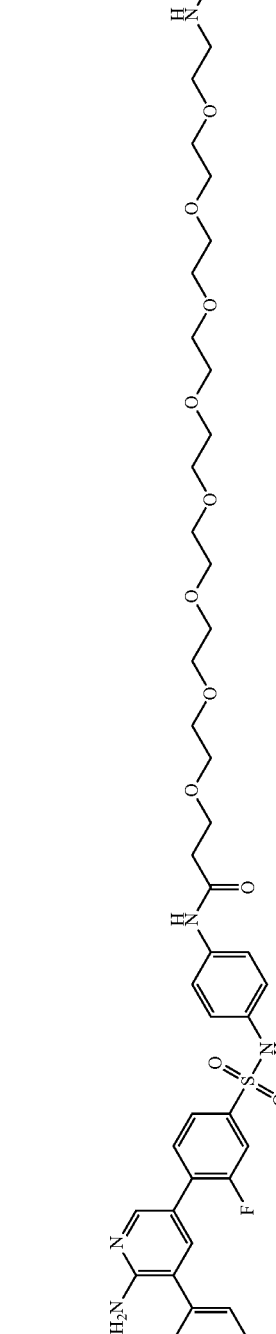 |
| I-12 | 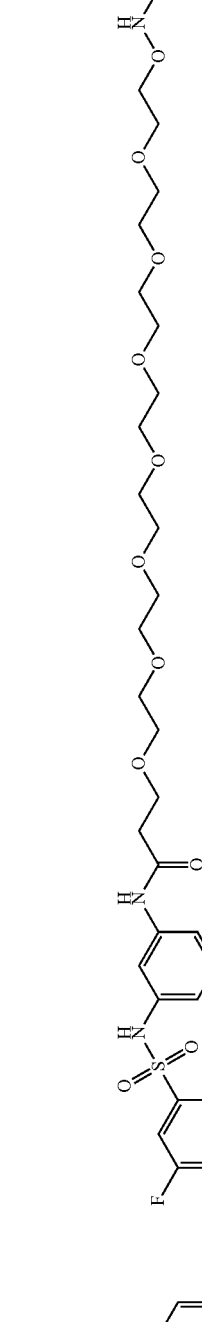 |

-continued

| Compound ID | Structure |
|---|---|
| I-13 | 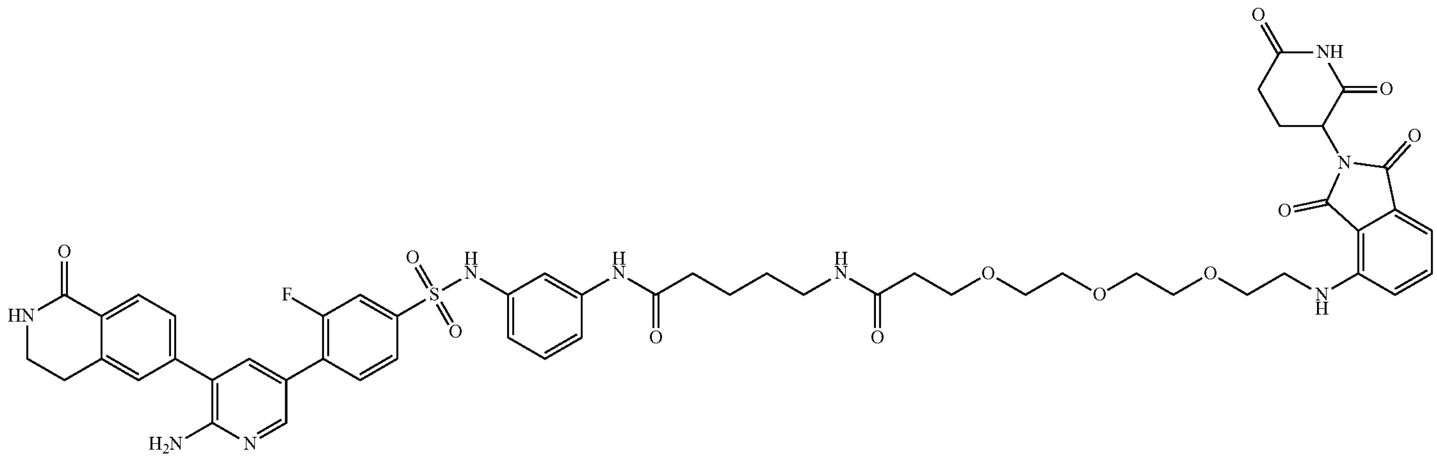 [SMILES: Nc1ncc(-c2ccc(S(=O)(=O)Nc3cccc(NC(=O)CCCCNC(=O)CCOCCOCCOCCNc4cccc5c4C(=O)N(C4CCC(=O)NC4=O)C5=O)c3)cc2F)cc1-c1ccc2c(c1)CCNC2=O] |
| I-14 | 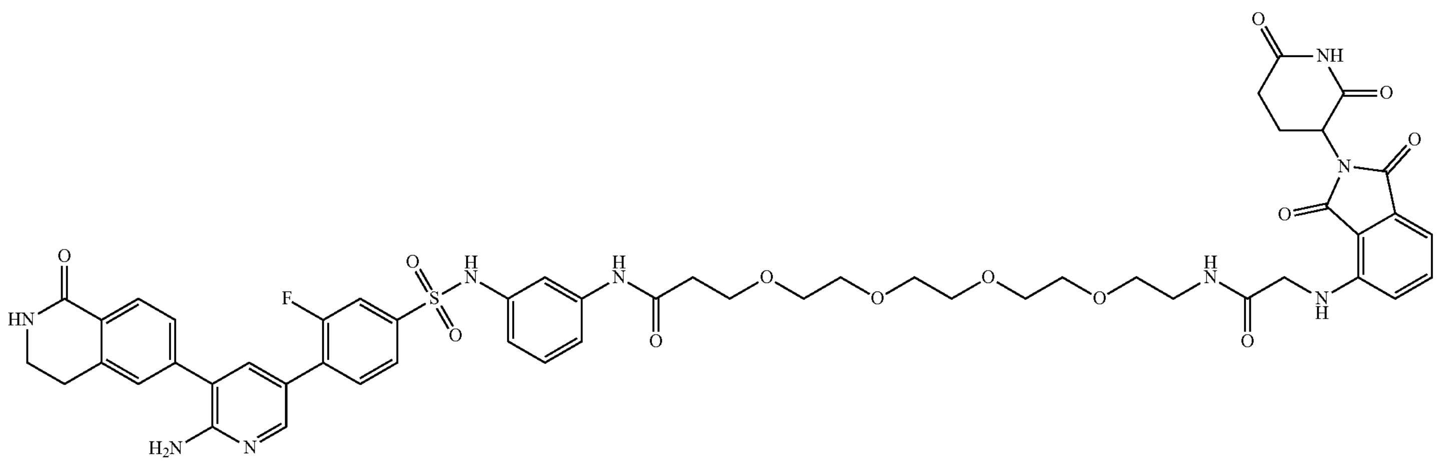 [SMILES: Nc1ncc(-c2ccc(S(=O)(=O)Nc3cccc(NC(=O)CCOCCOCCOCCOCCNC(=O)CNc4cccc5c4C(=O)N(C4CCC(=O)NC4=O)C5=O)c3)cc2F)cc1-c1ccc2c(c1)CCNC2=O] |

| Compound ID | Structure |
|---|---|
| I-15 | 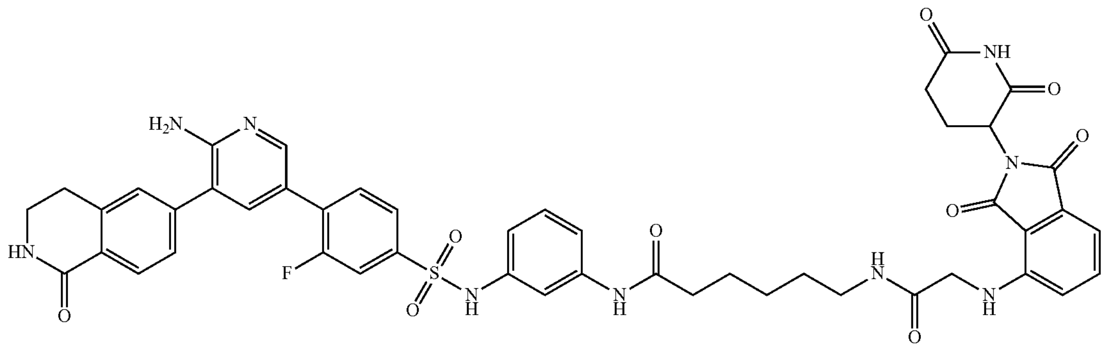 [SMILES: Nc1ncc(-c2ccc(S(=O)(=O)Nc3cccc(NC(=O)CCCCCNC(=O)CNc4cccc5c4C(=O)N(C4CCC(=O)NC4=O)C5=O)c3)cc2F)cc1-c1ccc2c(c1)CCNC2=O] |
| I-16 | 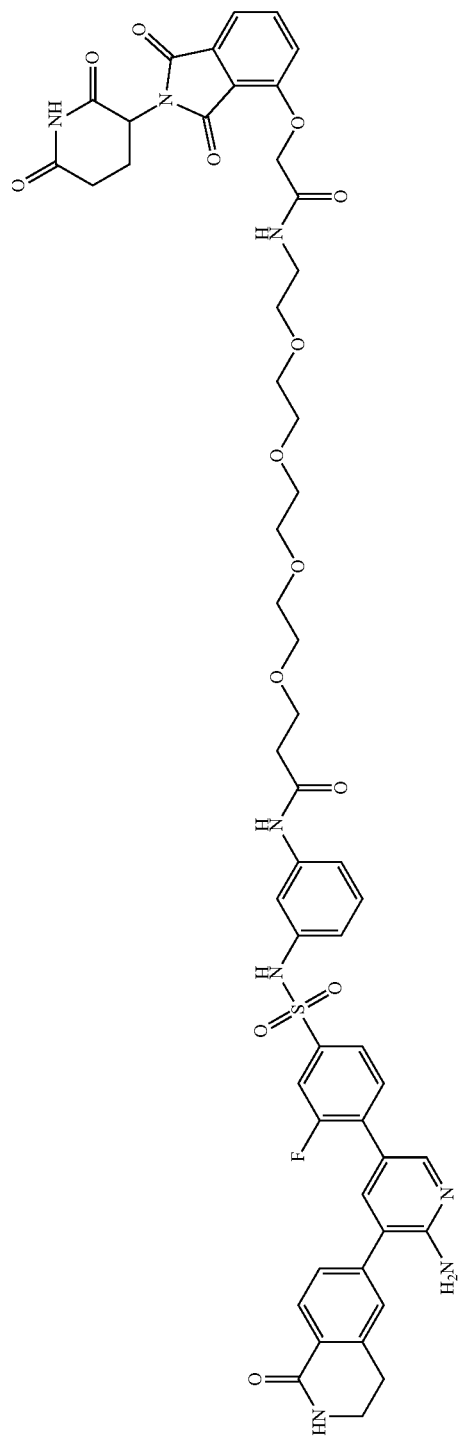 |

-continued

| Compound ID | Structure |
|---|---|
| I-17 | 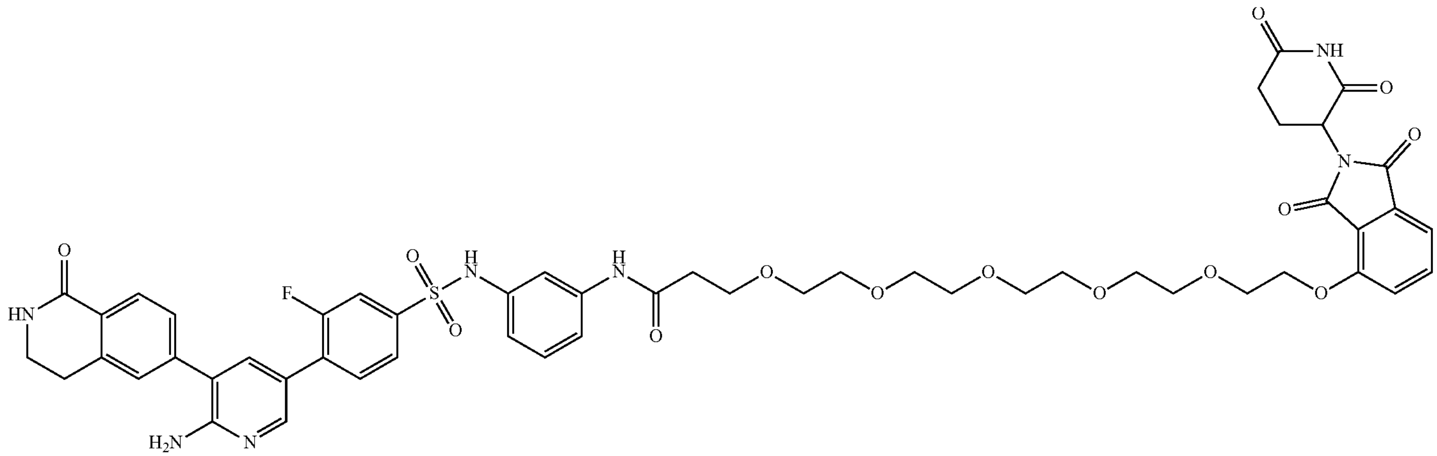 [SMILES: Nc1ncc(-c2ccc(S(=O)(=O)Nc3cccc(NC(=O)CCOCCOCCOCCOCCOCCOc4cccc5c4C(=O)N(C4CCC(=O)NC4=O)C5=O)c3)cc2F)cc1-c1ccc2c(c1)CCNC2=O] |
| I-18 | 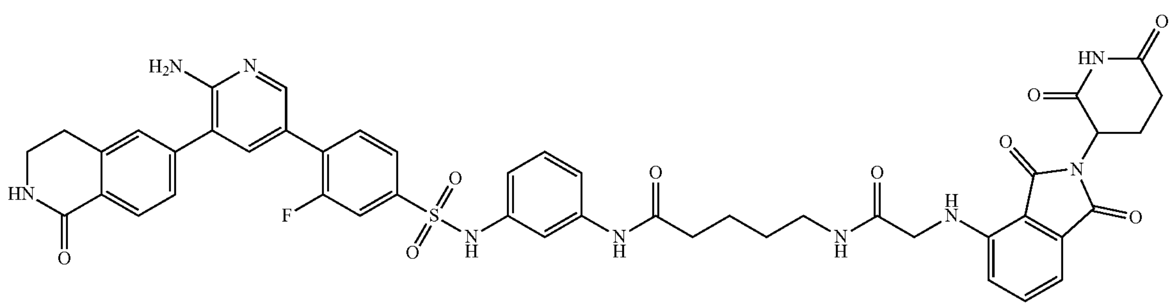 [SMILES: Nc1ncc(-c2ccc(S(=O)(=O)Nc3cccc(NC(=O)CCCCNC(=O)CNc4cccc5c4C(=O)N(C4CCC(=O)NC4=O)C5=O)c3)cc2F)cc1-c1ccc2c(c1)CCNC2=O] |

| Compound ID | Structure |
|---|---|
| I-19 | 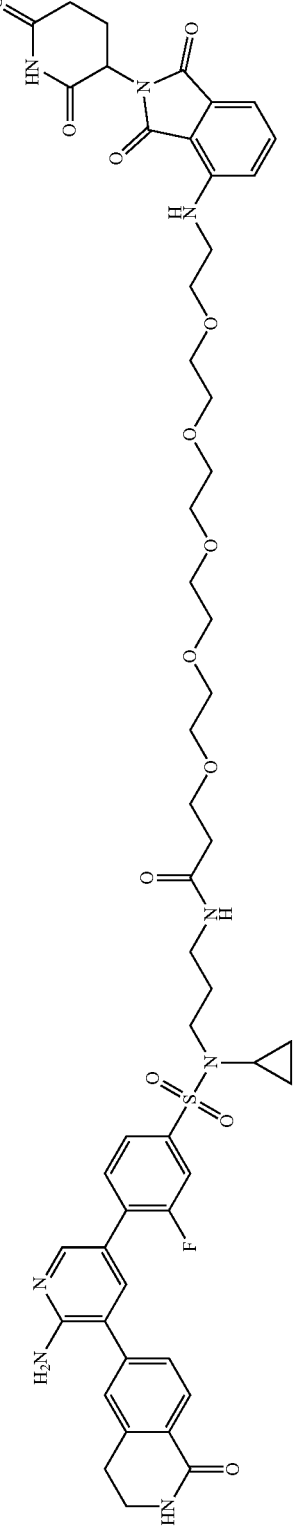 |
| I-20 | 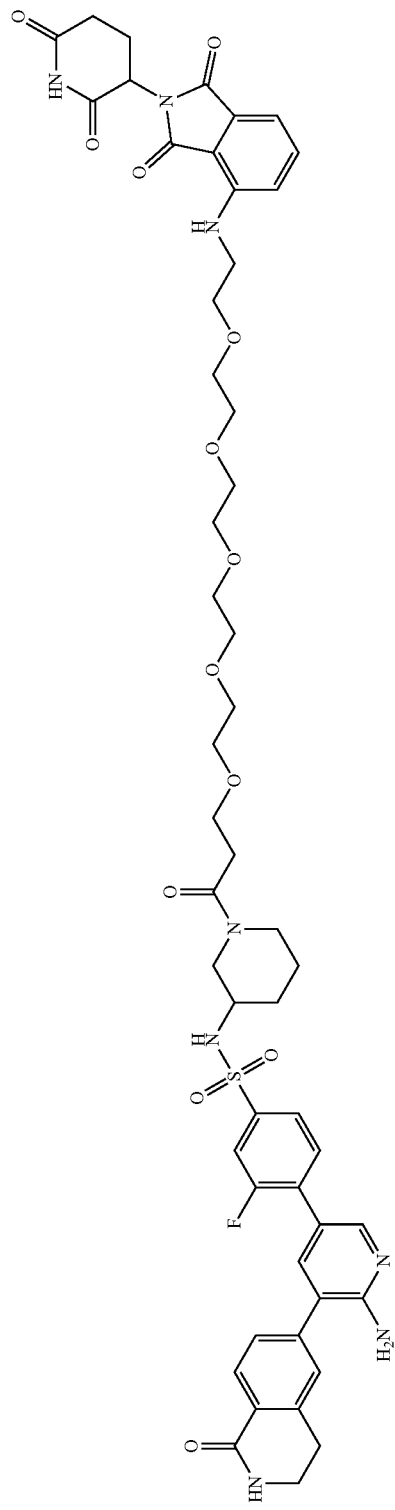 |

-continued
| Compound ID | Structure |
|---|---|
| I-20R | 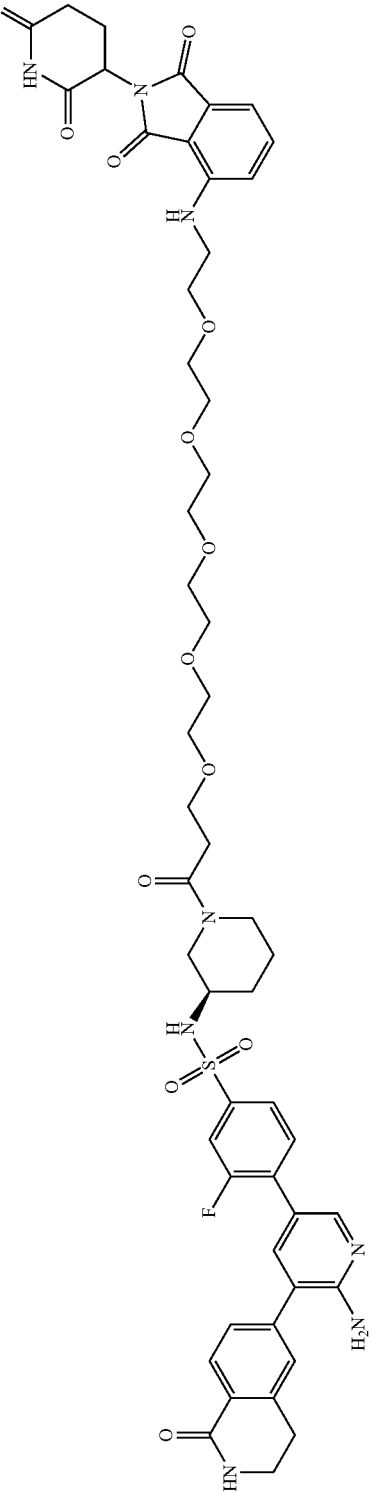 |
| I-21 | 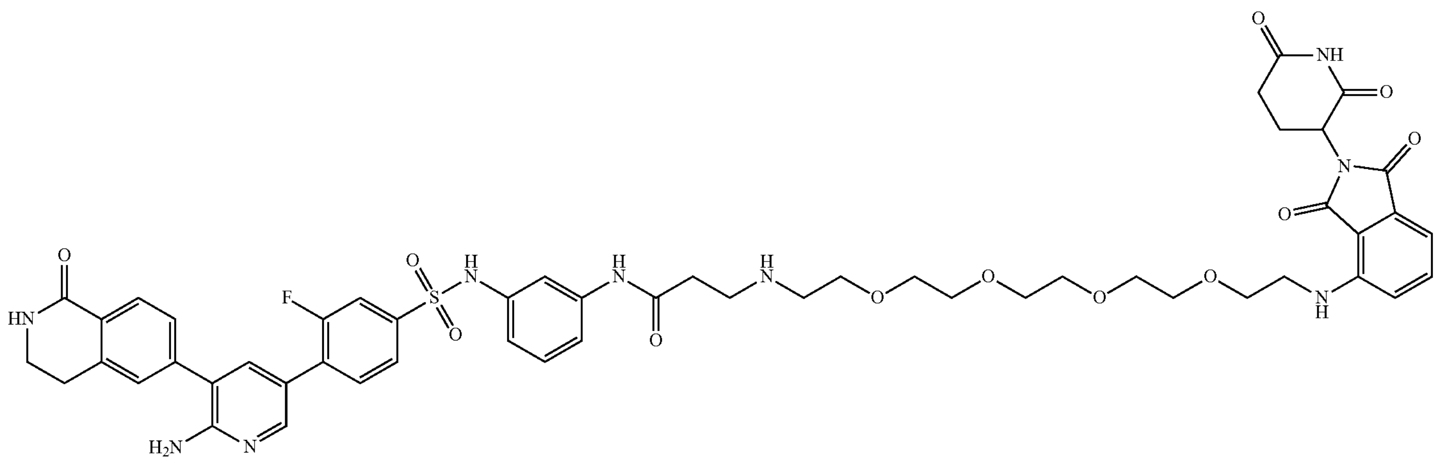 [SMILES: Nc1ncc(-c2ccc(S(=O)(=O)Nc3cccc(NC(=O)CCNCCOCCOCCOCCOCCNc4cccc5c4C(=O)N(C4CCC(=O)NC4=O)C5=O)c3)cc2F)cc1-c1ccc2c(c1)CCNC2=O] |

| Compound ID | Structure |
|---|---|
| I-22 | *(chemical structure)* |
| I-23 | *(chemical structure)* |

| Compound ID | Structure |
|---|---|
| I-24 | 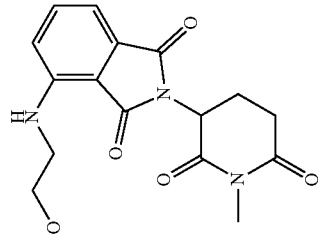 |

Some of the foregoing compounds can comprise one or more asymmetric centers, and thus can exist in various isomeric forms, e.g., stereoisomers and/or diastereomers. Accordingly, compounds of the application may be in the form of an individual enantiomer, diastereomer or geometric isomer, or may be in the form of a mixture of stereoisomers. In one embodiment, the compounds of the application are enantiopure compounds. In another embodiment, mixtures of stereoisomers or diastereomers are provided.

Furthermore, certain compounds, as described herein, may have one or more double bonds that can exist as either the Z or E isomer, unless otherwise indicated. The application additionally encompasses the compounds as individual Z/E isomers substantially free of other E/Z isomers and alternatively, as mixtures of various isomers.

In one embodiment, the present application relates to compounds that target STK4 for degradation, which have numerous advantages over inhibitors of STK4, and can a) overcome resistance in certain cases; b) prolong the kinetics of drug effect by destroying the protein, thus requiring resynthesis of the protein even after the compound has been metabolized; c) target all functions of a protein at once rather than a specific catalytic activity or binding event; d) expand the number of drug targets by including all proteins that a ligand can be developed for, rather than proteins whose activity (e.g., target protein or protein kinase activity) can be affected by a small molecule inhibitor, antagonist or agonist; and e) have increased potency compared to inhibitors due to the possibility of the small molecule acting catalytically.

Some embodiments of the present application relate to degradation or loss of 30% to 100% of STK4. Some embodiments relate to the loss of 50-100% of STK4. Other embodiments relate to the loss of 75-95% of STK4.

A compound of the present application (e.g., a compound of any of the formulae described herein, or selected from any compounds described herein) is capable of modulating (e.g., decreasing) the amount of STK4, or modulating (e.g., increasing) the amount of a protein regulated by STK4 (e.g., YAP1). A compound of the present application (e.g., a compound of any of the formulae described herein, or selected from any compounds described herein) is also capable of degrading STK4 through the UPP pathway. Accordingly, a compound of the present application (e.g., a compound of any of the formulae described herein, or selected from any compounds described herein) is capable of treating or preventing a disease or disorder in which STK4 plays a role. A compound of the present application (e.g., a compound of any of the formulae described herein, or selected from any compounds described herein) is also capable of treating or preventing a disease or disorder in which STK4, or a protein regulated by STK4 (e.g., YAP1), is deregulated.

Modulation of STK4 through UPP-mediated degradation by a compound of the application, such as those described herein, provides a novel approach to the treatment, prevention, or amelioration of diseases or disorders in which STK4 plays a role, including but not limited to, cancer and metastasis. Further, modulation of STK4 through UPP-mediated degradation by a compound of the application, such as those described herein, also provides a new paradigm for treating, preventing, or ameliorating diseases or disorders in which STK4, or a protein regulated by STK4 (e.g., YAP1), is deregulated.

In one embodiment, a compound of the present application (e.g., a compound of any of the formulae described herein, or selected from any compounds described herein) is more efficacious in treating a disease or condition (e.g., cancer) than, or is capable of treating a disease or condition resistant to, the Targeting Ligand and/or a known anti-proliferative reagent (e.g., pomalidomide or lenalidomide), when the Targeting Ligand or the known anti-proliferative reagent (e.g., pomalidomide or lenalidomide) is administered alone (i.e., when the Targeting Ligand is not bonded to a Linker and a Degron). In one embodiment, a compound of the present application (e.g., a compound of any of the formulae described herein, or selected from any compounds described herein) is capable of modulating (e.g., decreasing) the amount of STK4, or modulating (e.g., increasing) the amount of a protein regulated by STK4 (e.g., YAP1), and thus is useful in treating a disease or condition (e.g., cancer) in which STK4 plays a role.

In one embodiment, the compound of the present application that is more efficacious in treating a disease or condition than, or is capable of treating a disease or condition resistant to, the Targeting Ligand and/or a known anti-proliferative reagent (e.g., pomalidomide or lenalidomide), when the Targeting Ligand or a known anti-proliferative reagent (e.g., pomalidomide or lenalidomide) is administered alone (i.e., when the Targeting Ligand is not bonded to a Linker and a Degron), or is more potent in inhibiting the growth of cells (e.g., cancer cells) or decreasing the viability of cells (e.g., cancer cells), than the Targeting Ligand and/or a known anti-proliferative reagent (e.g., pomalidomide or lenalidomide), when the Targeting Ligand or a known anti-proliferative reagent (e.g., pomalidomide or lenalidomide) is administered alone (i.e., when the Targeting Ligand is not bonded to a Linker and a Degron). In one embodiment, the compound inhibits the growth of cells (e.g., cancer cells) or decreases the viability of cells (e.g., cancer cells) at an $IC_{50}$ that is lower than the $IC_{50}$ of the Targeting Ligand and/or a known anti-proliferative reagent (e.g., pomalidomide or lenalidomide), when the Targeting Ligand or a known anti-proliferative reagent (e.g., pomalidomide or lenalidomide) is administered alone (i.e., when the Targeting Ligand is not bonded to a Linker and a Degron) for inhibiting the growth or decreasing the viability of the cells. In one embodiment, the $IC_{50}$ of the compound is at most 90%, 80%, 70%, 60%, 50%, 40%, 30%, 20%, 10%, 8%, 5%, 4%, 3%, 2%, 1%, 0.8%, 0.5%.0.4%, 0.3%, 0.2%, or 0.1% of the $IC_{50}$ of the Targeting Ligand or a known anti-proliferative reagent (e.g., pomalidomide or lenalidomide). In one embodiment, the $IC_{50}$ of the compound is at most 50%, 40%, 30%, 20%, 10%, 8%, 5%, 4%, 3%, 2%, 1%, 0.8%, 0.5%, 0.4%, 0.3%, 0.2%, or 0.1% of the $IC_{50}$ of the Targeting Ligand or a known anti-proliferative reagent (e.g., pomalidomide or lenalidomide). In one embodiment, the $IC_{50}$ of the compound is at most 30%, 20%, 10%.8%, 5%, 4%, 3%, 2%, 1%, 0.8%, 0.5%, 0.4%, 0.3%, 0.2%, or 0.1% of the $IC_{50}$ of the Targeting Ligand or a known anti-proliferative reagent (e.g., pomalidomide or lenalidomide). In one embodiment, the $IC_{50}$ of the compound is at most 10%, 8%, 5%, 4%, 3%, 2%, 1%, 0.8%, 0.5%, 0.4%, 0.3%, 0.2%, or 0.1% of the $IC_{50}$ of the Targeting Ligand or a known anti-proliferative reagent (e.g., pomalidomide or lenalidomide). In one embodiment, the $IC_{50}$ of the compound is at most 5%, 4%, 3%, 2%, 1%, 0.8%, 0.5%.0.4%, 0.3%, 0.2%, or 0.1% of the $IC_{50}$ of the Targeting Ligand or a known anti-proliferative reagent (e.g., pomalidomide or lenalidomide). In one embodiment, the $IC_{50}$ of the compound is at most 2%, 1%, 0.8%, 0.5%, 0.4%, 0.3%, 0.2%, or 0.1% of the $IC_{50}$ of the Targeting Ligand or a known anti-proliferative reagent (e.g., pomalidomide or lenalidomide). In one embodiment, the $IC_{50}$ of the compound is at most 1%, 0.8%, 0.5%, 0.4%, 0.3%, 0.2%, or 0.1% of the IC$_{50}$ of the Targeting Ligand or a known anti-proliferative reagent (e.g., pomalidomide or lenalidomide).

In one embodiment, the compound inhibits the growth of cells (e.g., cancer cells) or decreases the viability of cells (e.g., cancer cells) at an E$_{max}$ that is lower than the E$_{max}$ of the Targeting Ligand and/or a known anti-proliferative reagent (e.g., pomalidomide or lenalidomide), when the Targeting Ligand or a known anti-proliferative reagent (e.g., pomalidomide or lenalidomide) is administered alone (i.e., when the Targeting Ligand is not bonded to a Linker and a Degron) for inhibiting the growth or decreasing the viability of the cells. In one embodiment, the E$_{max}$ of the compound is at most 90%, 80%, 70%, 60%, 50%, 40%, 30%, 20%, 10%, 8%, 5%, 4%, 3%, 2%, or 1% of the E$_{max}$ of the Targeting Ligand or a known anti-proliferative reagent (e.g., pomalidomide or lenalidomide). In one embodiment, the E$_{max}$ of the compound is at most 50%, 40%, 30%, 20%, 10%, 8%, 5%, 4%, 3%, 2%, or 1% of the E$_{max}$ of the Targeting Ligand or a known anti-proliferative reagent (e.g., pomalidomide or lenalidomide).

In one embodiment, the compounds of the present application prevent STK4 from reducing YAP1 levels.

In one embodiment, the compounds of the present application prevent or reduce phosphorylation activity of STK4.

In some embodiments, the inhibition of STK4 activity or STK4-dependent cell growth is measured by IC$_{50}$.

In some embodiments, the inhibition of STK4 activity or STK4-dependent cell growth is measured by EC$_{50}$.

Potency of a compound can be determined by IC$_{50}$ value. A compound with a lower IC$_{50}$ value, as determined under substantially similar conditions, is more potent relative to a compound with a higher IC$_{50}$ value. In some embodiments, the substantially similar conditions comprise determining a STK4-dependent cell growth.

In one embodiment, the compounds of the present application are useful as anticancer agents, and thus may be useful in the treatment of cancer, by effecting tumor cell death or inhibiting the growth of tumor cells. In certain exemplary embodiments, the disclosed anticancer agents are useful in the treatment of cancers and other proliferative disorders, including, but not limited to breast cancer, cervical cancer, colon and rectal cancer, leukemia, lung cancer (e.g., non-small cell lung cancer), melanoma, multiple myeloma, non-Hodgkin's lymphoma, ovarian cancer, pancreatic cancer, prostate cancer, gastric cancer, leukemias (e.g., myeloid, lymphocytic, myelocytic and lymphoblastic leukemias), malignant melanomas, and T-cell lymphoma.

Definitions

Listed below are definitions of various terms used to describe this application. These definitions apply to the terms as they are used throughout this specification and claims, unless otherwise limited in specific instances, either individually or as part of a larger group.

The term "alkyl," as used herein, refers to saturated, straight- or branched-chain hydrocarbon radicals containing, in one embodiment, between one and six, or one and eight carbon atoms, respectively. Examples of C$_1$-C$_6$ alkyl radicals include, but are not limited to, methyl, ethyl, propyl, isopropyl, n-butyl, tert-butyl, neopentyl, n-hexyl radicals; and examples of C$_1$-C$_8$ alkyl radicals include, but are not limited to, methyl, ethyl, propyl, isopropyl, n-butyl, tert-butyl, neopentyl, n-hexyl, heptyl, octyl radicals.

The term "alkenyl," as used herein, denotes a monovalent group derived from a hydrocarbon moiety containing, in one embodiment, from two to six, or two to eight carbon atoms having at least one carbon-carbon double bond. The double bond may or may not be the point of attachment to another group. Alkenyl groups include, but are not limited to, for example, ethenyl, propenyl, butenyl, 1-methyl-2-buten-1-yl, heptenyl, octenyl and the like.

The term "alkynyl," as used herein, denotes a monovalent group derived from a hydrocarbon moiety containing, in one embodiment, from two to six, or two to eight carbon atoms having at least one carbon-carbon triple bond. The alkynyl group may or may not be the point of attachment to another group. Representative alkynyl groups include, but are not limited to, for example, ethynyl, 1-propynyl, 1-butynyl, heptynyl, octynyl and the like.

The term "alkoxy" refers to an —O-alkyl radical.

The terms "hal," "halo," and "halogen," as used herein, refer to an atom selected from fluorine, chlorine, bromine and iodine.

The term "aryl," as used herein, refers to a mono- or poly-cyclic carbocyclic ring system having one or more aromatic rings, fused or non-fused, including, but not limited to, phenyl, naphthyl, tetrahydronaphthyl, indanyl, indenyl and the like.

The term "aralkyl," as used herein, refers to an alkyl residue attached to an aryl ring. Examples include, but are not limited to, benzyl, phenethyl and the like.

The term "cycloalkyl." as used herein, denotes a monovalent group derived from a monocyclic or polycyclic saturated or partially unsaturated carbocyclic ring compound. Examples of C$_3$-C$_8$-cycloalkyl include, but not limited to, cyclopropyl, cyclobutyl, cyclopentyl, cyclohexyl, cyclopentyl and cyclooctyl; and examples of C$_3$-C$_{12}$-cycloalkyl include, but not limited to, cyclopropyl, cyclobutyl, cyclopentyl, cyclohexyl, bicyclo [2.2.1]heptyl, and bicyclo [2.2.2] octyl. Also contemplated is a monovalent group derived from a monocyclic or polycyclic carbocyclic ring compound having at least one carbon-carbon double bond by the removal of a single hydrogen atom. Examples of such groups include, but are not limited to, cyclopropenyl, cyclobutenyl, cyclopentenyl, cyclohexenyl, cycloheptenyl, cyclooctenyl, and the like.

The term "heteroaryl," as used herein, refers to a mono- or poly-cyclic (e.g., bi-, or tri-cyclic or more) fused or non-fused, radical or ring system having at least one aromatic ring, having from five to ten ring atoms of which one ring atom is selected from S, O, and N; zero, one, or two ring atoms are additional heteroatoms independently selected from S, O, and N; and the remaining ring atoms are carbon. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

The term "heteroaralkyl," as used herein, refers to an alkyl residue attached to a heteroaryl ring. Examples include, but are not limited to, pyridinylmethyl, pyrimidinylethyl and the like.

The term "heterocyclyl," or "heterocycloalkyl," as used herein, refers to a non-aromatic 3-, 4-, 5-, 6- or 7-membered ring or a bi- or tri-cyclic group fused of non-fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, and (v) any of the above rings may be fused to a benzene ring. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "alkylamino" refers to a group having the structure —NH($C_1$-$C_{12}$ alkyl) where $C_1$-$C_{12}$ alkyl is as previously defined.

The term "dialkylamino" refers to a group having the structure —N($C_1$-$C_{12}$ alkyl)$_2$ where $C_1$-$C_{12}$ alkyl is as previously defined.

In accordance with the application, any of the aryls, substituted aryls, heteroaryls and substituted heteroaryls described herein, can be any aromatic group. Aromatic groups can be substituted or unsubstituted.

As described herein, compounds of the application may optionally be substituted with one or more substituents, such as are illustrated generally above, or as exemplified by particular classes, subclasses, and species of the application. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. The terms "optionally substituted". "optionally substituted alkyl," "optionally substituted "optionally substituted alkenyl," "optionally substituted alkynyl", "optionally substituted cycloalkyl," "optionally substituted cycloalkenyl," "optionally substituted aryl", "optionally substituted heteroaryl," "optionally substituted aralkyl", "optionally substituted heteroaralkyl," "optionally substituted heterocycloalkyl," and any other optionally substituted group as used herein, refer to groups that are substituted or unsubstituted by independent replacement of one, two, or three or more of the hydrogen atoms thereon with substituents including, but not limited to:
—F, —$C_1$, —Br, —I, —OH, protected hydroxy, —$NO_2$, —CN, —$NH_2$, protected amino, —NH—$C_1$-$C_{12}$-alkyl, —NH—$C_2$-$C_{12}$-alkenyl, —NH—$C_2$-$C_{12}$-alkenyl, —NH—$C_3$-$C_{12}$-cycloalkyl,
—NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_{12}$-alkenyl, —O—$C_2$-$C_{12}$-alkenyl, —O—$C3$-$C_{12}$-cycloalkyl, —O-aryl, —O-heteroaryl, —O-heterocycloalkyl, —C(O)—$C_1$-$C_{12}$-alkyl, —C(O)—$C_2$-$C_{12}$-alkenyl, —C(O)—$C_2$-$C_{12}$-alkenyl, —C(O)—$C_3$-$C_{12}$-cycloalkyl, —C(O)-aryl, —C(O)— heteroaryl,
—C(O)-heterocycloalkyl, —$CONH_2$, —CONH—$C_1$-$C_{12}$-alkyl, —CONH—$C_2$-$C_{12}$-alkenyl,
—CONH—$C_2$-$C_{12}$-alkenyl, —CONH—$C_3$-$C_{12}$-cycloalkyl, —CONH-aryl, —CONH-heteroaryl, —CONH-heterocycloalkyl,
—$OCO_2$—$C_1$-$C_{12}$-alkyl, —$OCO_2$—$C_2$-$C_{12}$-alkenyl, —$OCO_2$—$C_2$-$C_{12}$-alkenyl,
—$OCO_2$—$C_3$-$C_{12}$-cycloalkyl, —$OCO_2$-aryl, —$OCO_2$-heteroaryl, —$OCO_2$-heterocycloalkyl, —$OCONH_2$,
—OCONH—$C_1$-$C_{12}$-alkyl, —OCONH— $C_2$-$C_{12}$-alkenyl, —OCONH—$C_2$-$C_{12}$-alkenyl,
—OCONH—$C_3$-$C_{12}$-cycloalkyl, —OCONH-aryl, —OCONH-heteroaryl, —OCONH— heterocycloalkyl,
—NHC(O)—$C_1$-$C_{12}$-alkyl, —NHC(O)—$C_2$-$C_{12}$-alkenyl, —NHC(O)—$C_2$-$C_{12}$-alkenyl,
—NHC(O)—$C_3$-$C_{12}$-cycloalkyl, —NHC(O)-aryl, —NHC(O)-heteroaryl, —NHC(O)— heterocycloalkyl,
—$NHCO_2$—$C_1$-$C_{12}$-alkyl, —$NHCO_2$—$C_2$-$C_{12}$-alkenyl, —$NHCO_2$—$C_2$-$C_{12}$-alkenyl,
—$NHCO_2$—$C_3$-$C_{12}$-cycloalkyl, —$NHCO_2$-aryl, —$NHCO_2$-heteroaryl, —$NHCO_2$-heterocycloalkyl, NHC(O)$NH_2$, —NHC(O)NH—$C_1$-$C_{12}$-alkyl, —NHC(O)NH—$C_2$-$C_{12}$-alkenyl,
—NHC(O)NH—$C_2$-$C_{12}$-alkenyl, —NHC(O)NH—$C_3$-$C_{12}$-cycloalkyl, —NHC(O)NH-aryl,
—NHC(O)NH-heteroaryl, NHC(O)NH-heterocycloalkyl, NHC(S)$NH_2$, —NHC(S)NH—$C_1$-$C_{12}$-alkyl, —NHC(S) NH—$C_2$-$C_{12}$-alkenyl,
—NHC(S)NH—$C_2$-$C_{12}$-alkenyl, —NHC(S)NH—$C_3$-$C_{12}$-cycloalkyl, —NHC(S)NH-aryl,
—NHC(S)NH-heteroaryl, —NHC(S)NH-heterocycloalkyl, —NHC(NH)$NH_2$,
—NHC(NH)NH— $C_1$-$C_{12}$-alkyl, —NHC(NH)NH—$C_2$-$C_{12}$-alkenyl, —NHC(NH)NH—$C_2$-$C_{12}$-alkenyl,
—NHC(NH)NH—$C_3$-$C_{12}$-cycloalkyl, —NHC(NH)NH-aryl. —NHC(NH)NH-heteroaryl,
—NHC(NH)NHheterocycloalkyl, —NHC(NH)—$C_1$-$C_{12}$-alkyl, —NHC(NH)—$C_2$-$C_{12}$-alkenyl,
—NHC(NH)—$C_2$-$C_{12}$-alkenyl, —NHC(NH)—$C_3$-$C_{12}$-cycloalkyl, —NHC(NH)-aryl,
—NHC(NH)-heteroaryl, —NHC(NH)-heterocycloalkyl, —C(NH)NH—$C_1$-$C_{12}$-alkyl,
—C(NH)NH—$C_2$-$C_{12}$-alkenyl, —C(NH)NH—$C_2$-$C_{12}$-alkenyl, C(NH)NH—$C_3$-$C_{12}$-cycloalkyl,
—C(NH)NH-aryl, —C(NH)NH-heteroaryl, —C(NH) NHheterocycloalkyl,
—S(O)—$C_1$-$C_{12}$-alkyl, —S(O)—$C_2$-$C_{12}$-alkenyl, —S(O)—$C_2$-$C_{12}$-alkenyl,
—S(O)—$C_3$-$C_{12}$-cycloalkyl, —S(O)-aryl, —S(O)-heteroaryl, —S(O)-heterocycloalkyl —$SO_2NH_2$,
—$SO_2$NH—$C_1$-$C_{12}$-alkyl, —$SO_2$NH—$C_2$-$C_{12}$-alkenyl, —$SO_2$NH—$C_2$-$C_{12}$-alkenyl,
—$SO_2$NH—$C_3$-$C_{12}$-cycloalkyl, —$SO_2$NH-aryl, —$SO_2$NH-heteroaryl, —$SO_2$NH-heterocycloalkyl,
—$NHSO_2$—$C_1$-$C_{12}$-alkyl, —$NHSO_2$—$C_2$-$C_{12}$-alkenyl-$NHSO_2$—$C_2$-$C_{12}$-alkenyl,
—$NHSO_2$—$C_3$-$C_{12}$-cycloalkyl, —$NHSO_2$-aryl, —$NHSO_2$-heteroaryl, —$NHSO_2$-heterocycloalkyl,
—$CH_2NH_2$, —$CH_2SO_2CH_3$-aryl, -arylalkyl, -heteroaryl, -heteroarylalkyl, -heterocycloalkyl,
—$C_3$-$C_{12}$-cycloalkyl, polyalkoxyalkyl, polyalkoxy, -methoxymethoxy, -methoxyethoxy, —SH,
—S—$C_1$-$C_{12}$-alkyl, —S—$C_2$-$C_{12}$-alkenyl. —S—$C_2$-$C_{12}$-alkenyl. —S—$C_3$-$C_{12}$-cycloalkyl, —S-aryl,
—S-heteroaryl, —S-heterocycloalkyl, or methylthiomethyl.

It is understood that the aryls, heteroaryls, alkyls, and the like can be further substituted.

As defined herein. "Lenalidomide" is a compound having the following structure:

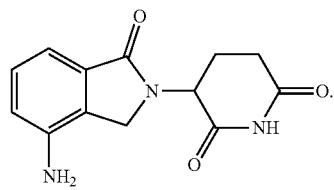 [SMILES: Nc1cccc2c1CN(C1CCC(=O)NC1=O)C2=O]

As defined herein, "Pomalidomide" is a compound having the following structure:

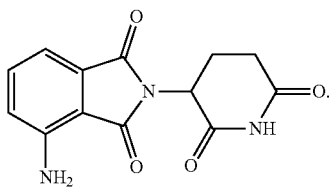 [SMILES: Nc1cccc2c1C(=O)N(C1CCC(=O)NC1=O)C2=O]

The term "cancer" includes, but is not limited to, the following cancers: epidermoid Oral: buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma, and teratoma; Lung: bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leionoma), colon, colon-rectum, colorectal, rectum; Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomvosarcoma), fallopian tubes (carcinoma), breast; Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma) hairy cell; lymphoid disorders; Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma; medullary thyroid carcinoma, undifferentiated thyroid cancer, multiple endocrine neoplasia type 2A, multiple endocrine neoplasia type 2B, familial medullary thyroid cancer, pheochromocytoma, paraganglioma; and Adrenal glands: neuroblastoma. Thus, the term "cancerous cell" as provided herein, includes a cell afflicted by any one of the above-identified conditions.

The term "hematopoietic disorder" as used herein refers to any type of disorder that affects hematopoietic cells. These include but are not limited to hematopoietic cancers. Non limiting examples of hematopoietic cancers include multiple myeloma, leukaemias and lymphomas. A non-limiting list of further hematopoietic disorders include, but are not limited to, aplastic anemia, myelodysplasia, and related bone marrow failure syndromes, polycythemia vera and other myeloproliferative diseases, acute and chronic myeloid leukemia, malignancies of lymphoid cells, less common hematologic malignancies, and plasma cell disorders.

The term "hematopoietic cells" as used herein includes all the blood cell types including those from the myeloid lineage (monocytes and macrophages, neutrophils, basophils, eosinophils, erythrocytes, megakaryocytes/platelets, dendritic cells), and lymphoid lineages (T-cells, B-cells, NK-cells).

Multiple myeloma is a malignant neoplasm of plasma cells in the bone marrow associated with an overproduction of monoclonal (M)-protein often causing characteristic osteolytic lesions, anemia, renal failure, and hypercalcemia. (Kyle, R. A., et al., Multiple myeloma., N. Engl. J. Med. 2004; 351(18):1860-1873) Monoclonal gammopathy of unknown significance (MGUS) is an asymptomatic plasma cell dyscrasia that is present in more than 3% of the general white population older than age 50 and has an average multiple myeloma progression risk of 1% per year. (Kyle, R. A., et al., Prevalence of monoclonal gammopathy of undetermined significance, N. Engl. J. Med. 2006; 354(13):1362-1369). Smoldering multiple myeloma (SMM) is another asymptomatic plasma cell disorder but carries a higher risk of progression to frank multiple myeloma (10% per year the first 5 years) compared with MGUS. (Kyle, R. A., et al., Clinical course and prognosis of smoldering (asymptomatic) multiple myeloma, N. Engl. J. Med. 2007; 356(25):2582-2590). It will be appreciated that the present application is useful for MGUS and SMM as well as multiple myeloma.

Leukaemias are described as lymphoid or myeloid leukaemias, depending on which type of hematopoietic cell the abnormal leukemia cells develop from. Leukaemias start in the bone marrow and the abnormal cells can spread from there into the bloodstream and to other parts of the body. Non limiting examples of leukemia include acute lymphoblastic leukemia (ALL), adult T cell leukemia (AIL), acute myeloblastic leukemia (AML), chronic lymphocytic leukemia (CLL) and chronic myeloid leukemia (CML).

Lymphomas start in lymphocytes. Abnormal lymphocytes can build up in lymph nodes, bone marrow and/or the spleen. Non limiting examples of lymphomas include non-Hodgkin's lymphomas such as Waldestrom Macroglobulinemia, Burkitt lymphoma, Mantle cell lymphoma, diffuse large B cell lymphoma and follicular lymphoma.

The term "YAP1 level" as used herein preferably refers to YAP1 level in hematopoietic cells.

The term "reduced level" or "reduced YAP1 level" as used herein refers to reduced level of YAP 1 relative to that of a non-diseased cell, preferably a non-diseased hematopoietic cell, or relative to YAP1 levels of a group of reference patients. The reference patients may be presenting with "high" levels for YAP1, and reduced level is relative to such high levels. The non-diseased cell may be from the same subject to be treated.

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient.

"Treat", "treating" and "treatment" refer to a method of alleviating or abating a disease and/or its attendant symptoms.

As used herein, "preventing" or "prevent" describes reducing or eliminating the onset of the symptoms or complications of the disease, condition or disorder.

The terms "disease(s)", "disorder(s)", and "condition(s)" are used interchangeably, unless the context clearly dictates otherwise.

As used herein, the term "pharmaceutically acceptable salt" refers to those salts of the compounds formed by the process of the present application which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in *J. Pharmaceutical Sciences*, 66: 1-19 (1977). The salts can be prepared in situ during the final isolation and purification of the compounds of the application, or separately by reacting the free base function with a suitable organic acid. Examples of pharmaceutically acceptable include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters of the compounds formed by the process of the present application which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds formed by the process of the present application which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present application. "Prodrug", as used herein means a compound which is convertible in vivo by metabolic means (e.g., by hydrolysis) to afford any compound delineated by the formulae of the instant application. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., Journal of Drug Deliver Reviews, 8:1-38(1992); Bundgaard, *J. of Pharmaceutical Sciences*, 77:285 et seq. (1988); Higuchi and Stella (eds.) Prodrugs as Novel Drug Delivery Systems. American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

This application also encompasses pharmaceutical compositions containing, and methods of treating disorders through administering, pharmaceutically acceptable prodrugs of compounds of the application. For example, compounds of the application having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the application. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxy carbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med Chem.* 1996, 39, 10. Free amines can also be derivatized as amides, sulfonamides or phosphonamides. All of these prodrug moieties may incorporate groups including but not limited to ether, amine and carboxylic acid functionalities Combinations of substituents and variables envisioned by this application are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The term "therapeutically effective amount" or "effective amount" of a compound or pharmaceutical composition of the application, as used herein, means a sufficient amount of the compound or pharmaceutical composition so as to decrease the symptoms of a disorder in a subject. As is well understood in the medical arts a therapeutically effective amount of a compound or pharmaceutical composition of this application will be at a reasonable benefit/risk ratio applicable to any medical treatment. It will be understood, however, that the total daily usage of the compounds and compositions of the present application will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The application also provides for a pharmaceutical composition comprising a compound of the present application, or a pharmaceutically acceptable ester, salt, or prodrug thereof, together with a pharmaceutically acceptable carrier.

In another aspect, the application provides a kit comprising a compound capable of modulating the amount of STK4 selected from one or more compounds of the present application, or a pharmaceutically acceptable salt, hydrate, solvate, prodrug, stereoisomer, or tautomer thereof, and instructions for use in treating cancer.

In another aspect, the application provides a method of synthesizing a compound of the present application.

The synthesis of the compounds of the application can be found herein and in the Examples below.

Another embodiment is a method of making a compound of any of the formulae herein using any one, or combination of, reactions delineated herein. The method can include the use of one or more intermediates or chemical reagents delineated herein.

Another aspect is an isotopically labeled compound of any of the formulae delineated herein. Such compounds have one or more isotope atoms which may or may not be radioactive (e.g., $^3H$, $^2H$, $^{14}C$, $^{13}C$, $^{18}F$, $^{35}S$, $^{32}P$, $^{125}I$, and $^{131}I$) introduced into the compound. Such compounds are useful for drug metabolism studies and diagnostics, as well as therapeutic applications.

A compound of the application can be prepared as a pharmaceutically acceptable acid addition salt by reacting the free base form of the compound with a pharmaceutically acceptable inorganic or organic acid. Alternatively, a pharmaceutically acceptable base addition salt of a compound of the application can be prepared by reacting the free acid form of the compound with a pharmaceutically acceptable inorganic or organic base.

Alternatively, the salt forms of the compounds of the application can be prepared using salts of the starting materials or intermediates.

The free acid or free base forms of the compounds of the application can be prepared from the corresponding base addition salt or acid addition salt from, respectively. For example a compound of the application in an acid addition salt form can be converted to the corresponding free base by treating with a suitable base (e.g., ammonium hydroxide solution, sodium hydroxide, and the like). A compound of the application in a base addition salt form can be converted to the corresponding free acid by treating with a suitable acid (e.g., hydrochloric acid, etc.).

Prodrug derivatives of the compounds of the application can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the application with a suitable carbamylating agent (e.g., 1,1-acyloxyalkylcarbanochloridate, para-nitrophenyl carbonate, or the like).

Protected derivatives of the compounds of the application can be made by means known to those of ordinary skill in the art. A detailed description of techniques applicable to the creation of protecting groups and their removal can be found in T. W. Greene, "Protecting Groups in Organic Chemistry", 3rd edition, John Wiley and Sons, Inc., 1999.

Compounds of the present application can be conveniently prepared, or formed during the process of the application, as solvates (e.g., hydrates). Hydrates of compounds of the present application can be conveniently prepared by recrystallization from an aqueous/organic solvent mixture, using organic solvents such as dioxin, tetrahydrofuran or methanol.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium trillate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

In addition, some of the compounds of this application have one or more double bonds, or one or more asymmetric centers. Such compounds can occur as racemates, racemic mixtures, single enantiomers, individual diastereomers, diastereomeric mixtures, and cis- or trans- or E- or Z-double isomeric forms, and other stereoisomeric forms that may be defined, in terms of absolute stereochemistry, as (R)- or (S)-, or as (D)- or (L)- for amino acids. When the compounds described herein contain olefinic double bonds or other centers of geometric asymmetry, and unless specified otherwise, it is intended that the compounds include both E and Z geometric isomers. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion. All such isomeric forms of these compounds are expressly included in the present application.

Optical isomers may be prepared from their respective optically active precursors by the procedures described herein, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., Enantiomers, Racemates, and Resolutions (John Wiley & Sons, 1981).

"Isomerism" means compounds that have identical molecular formulae but differ in the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images of each other are termed "enantiomers" or sometimes optical isomers. A mixture containing equal amounts of individual enantiomeric forms of opposite chirality is termed a "racemic mixture".

A carbon atom bonded to four non-identical substituents is termed a "chiral center".

"Chiral isomer" means a compound with at least one chiral center. Compounds with more than one chiral center may exist either as an individual diastereomer or as a mixture of diastereomers, termed "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the *Sequence Rule* of Cahn, Ingold and Prelog. (Cahn et al., *Angew. Chem. Inter. Edit.* 196, 5, 385; errata 511; Cahn et al., *Angew. Chem.* 1966, 78, 413; Cahn and Ingold, *J. Chem. Soc.* 1951 (London). 612; Cahn et al., *Experientia* 1956, 12, 81; Cahn, *J. Chem. Educ.* 1964, 41, 116).

"Geometric isomer" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Furthermore, the structures and other compounds discussed in this application include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques; it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solid form, usually one tautomer predominates. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose. Common tautomeric pairs are: ketone-enol, amide-nitrile, lactam-lactim, amide-imidic acid tautomerism in heterocyclic rings (e.g., in nucleobases such as guanine, thymine and cytosine), amine-enamine and enamine-enamine. The compounds of this application may also be represented in multiple tautomeric forms, in such instances, the application expressly includes all tautomeric forms of the compounds described herein (e.g., alkylation of a ring system may result in alkylation at multiple sites, the application expressly includes all such reaction products).

In the present specification, the structural formula of the compound represents a certain isomer for convenience in some cases, but the present application includes all isomers, such as geometrical isomers, optical isomers based on an asymmetrical carbon, stereoisomers, tautomers, and the like.

Additionally, the compounds of the present application, for example, the salts of the compounds, can exist in either hydrated or unhydrated (the anhydrous) form or as solvates with other solvent molecules. Non-limiting examples of hydrates include monohydrates, dihydrates, etc. Nonlimiting examples of solvates include ethanol solvates, acetone solvates, etc.

"Solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

The present application is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

It is to be understood that the compounds of the present application may be depicted as different tautomers. It should also be understood that when compounds have tautomeric forms, all tautomeric forms are intended to be included in the scope of the present application, and the naming of the compounds does not exclude any tautomer form.

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired bridged macrocyclic products of the present application. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts. Protective Groups in Organic Synthesis, 2d. Ed., John Wiley and Sons (1991), L. Fieser and M. Fieser, Fieser and Fieser's Reagents for Organic Synthesis, John Wiley and Sons (1994); and L. Paquette, ed., Encyclopedia of Reagents for Organic Synthesis. John Wiley and Sons (1995), and subsequent editions thereof.

The compounds of this application may be modified by appending various functionalities via any synthetic means delineated herein to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The compounds of the application are defined herein by their chemical structures and/or chemical names. Where a compound is referred to by both a chemical structure and a chemical name, and the chemical structure and chemical name conflict, the chemical structure is determinative of the compound's identity.

The recitation of a listing of chemical groups in any definition of a variable herein includes definitions of that variable as any single group or combination of listed groups. The recitation of an embodiment for a variable herein includes that embodiment as any single embodiment or in combination with any another embodiment or portions thereof.

Methods of Synthesizing the Compounds

The compounds of the present application may be made by a variety of methods, including standard chemistry. The synthetic processes of the application can tolerate a wide variety of functional groups, therefore various substituted starting materials can be used. The processes generally provide the desired final compound at or near the end of the overall process, although it may be desirable in certain instances to further convert the compound to a pharmaceutically acceptable salt, ester or prodrug thereof. Suitable synthetic routes are depicted in the Scheme I below.

Compounds of the present application can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure,* 5$^{th}$ edition, John Wiley & Sons: New York, 2001; and Greene, T. W., Wuts, P. G. M., *Protective Groups in Organic Synthesis,* 3$^{rd}$ edition. John Wiley & Sons: New York, 1999, incorporated by reference herein, are useful and recognized reference textbooks of organic synthesis known to those in the art. The following descriptions of synthetic methods are designed to illustrate, but not to limit, general procedures for the preparation of compounds of the present application.

The compounds of the present application may be prepared by methods known in the art of organic synthesis as set forth in part by the following synthetic schemes. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of the present application.

Those skilled in the art will recognize if a stereocenter exists in the compounds of the present application. Accordingly, the present application includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

The compounds described herein may be made from commercially available starting materials or synthesized using known organic, inorganic, and/or enzymatic processes.

All the abbreviations used in this application are found in "Protective Groups in Organic Synthesis" by John Wiley & Sons, Inc, or the MERCK INDEX by MERCK & Co., Inc, or other chemistry books or chemicals catalogs by chemicals vendor such as Aldrich, or according to usage know in the art.

General Scheme 1

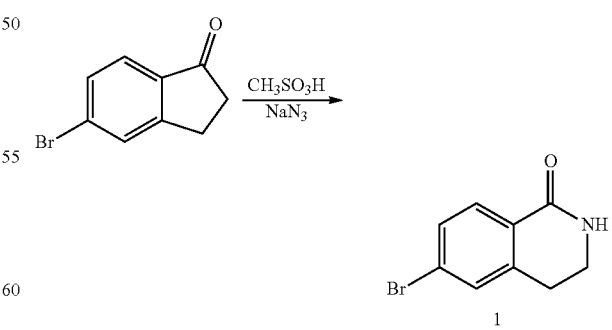

Under inert atmosphere, 5-bromo-2,3-dihydro-1H-inden-1-one and methanesulfonic acid are mixed in an appropriate solution (e.g., DCM), to which NaN$_3$ is slowly added to produce 1.

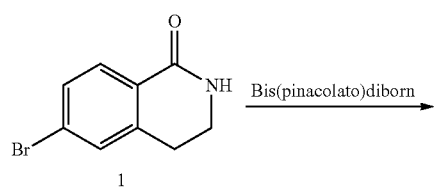

1

Bis(pinacolato)diborn →

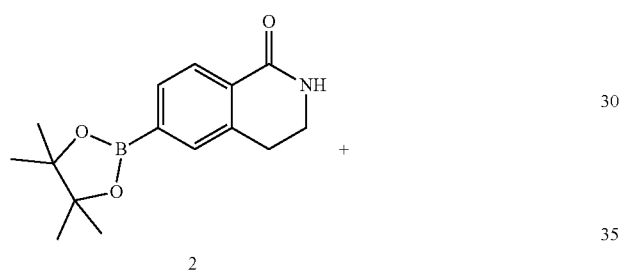

2

Under inert atmosphere, 1 and bis(pinacolato)diborn are reacted under appropriate conditions (e.g., in the presence of potassium acetate and Pd(dppf)Cl$_2$) to generate 2.

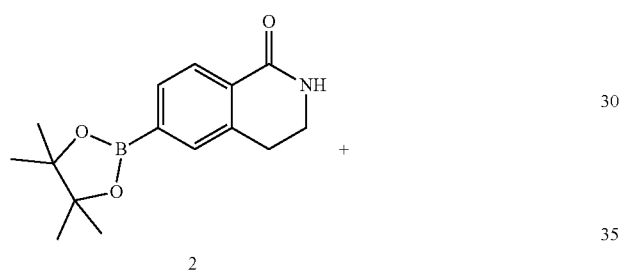

2

+

3

Under inert atmosphere, 2 and 5-bromo-3-iodopyridin-2-amine are reacted under appropriate conditions (e.g., in the presence of sodium carbonate and Pd(PPh$_3$)$_4$) to produce 3.

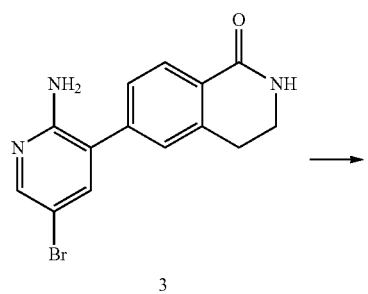

3

→

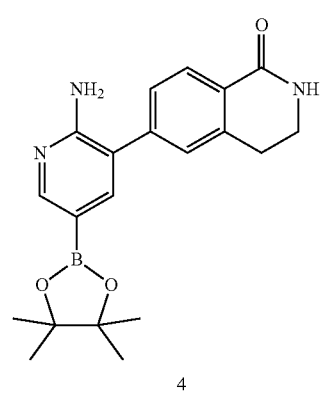

4

Under inert atmosphere, 3 and bis(pinacolato)diboron are mixed and reacted under appropriate conditions (e.g., in the presence of potassium acetate and Pd(dppf)Cl$_2$) to afford 4

General Scheme 2

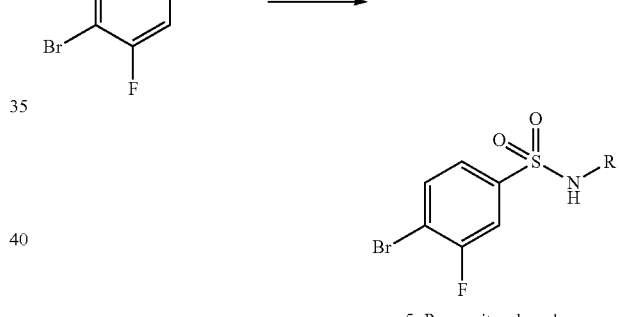

R—NH$_2$ →

5. R = p-nitrophenyl
6. R = m-nitrophenyl
7. R = 1-Boc-piperidine
8. R = cyclopropyl Method A for 5 and 6: 3-nitroaniline and 4-bromo-3-fluorobenzenesulfonyl chloride are mixed in an appropriate solvent (e.g., pyridine) and reacted to produce 5 or 6.

Method B for 7 and 8: 4-bromo-3-fluorobenzenesulfonyl chloride in an appropriate solvent (e.g., DCM) is added dropwise to a stirring solution of cyclopropanamine for a reaction to afford 7 or 8.

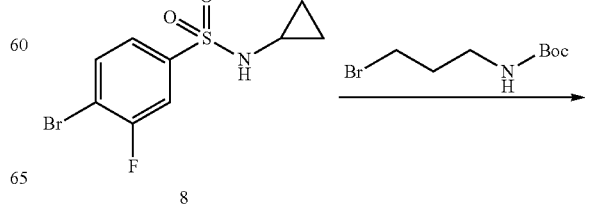

8

-continued

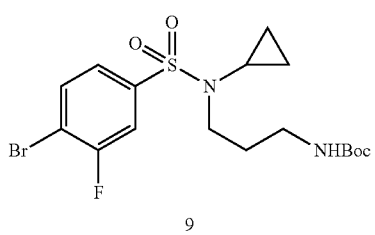

9

Under inert atmosphere, a solution of tert-butyl (3-bromopropyl)carbamate is added to a solution of 8 (607 mg, 2.55 mmol). The mixture is heated and reacted under appropriate conditions (e.g., in the presence of NaH and THF) to produce 9.

General Scheme 3

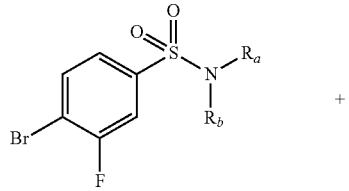

5. $R_a$ = p-nitrophenyl, $R_b$ = H
6. $R_a$ = m-nitrophenyl, $R_b$ = H
7. $R_a$ = 1-Boc-piperidine, $R_b$ = H
9. $R_a$ = cyclopropyl, $R_b$ = N-Boc-propan-1-amine

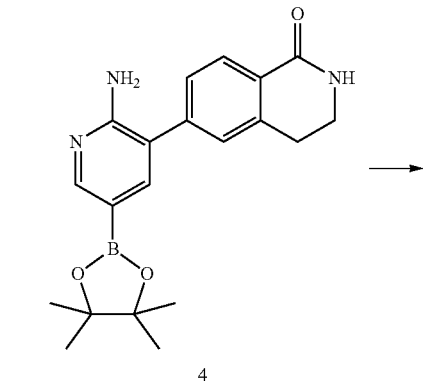

4

10. $R_a$ = p-nitrophenyl, $R_b$ = H
11. $R_a$ = m-nitrophenyl, $R_b$ = H
12. $R_a$ = 1-Boc-piperidine, $R_b$ = H
13. $R_a$ = cyclopropyl, $R_b$ = N-Boc-propan-1-amine General Procedure of Suzuki Coupling:

10, 11, 12, or 13 are prepared by Suzuki coupling between 4 and 5, 6, 7, or 8, respectively.

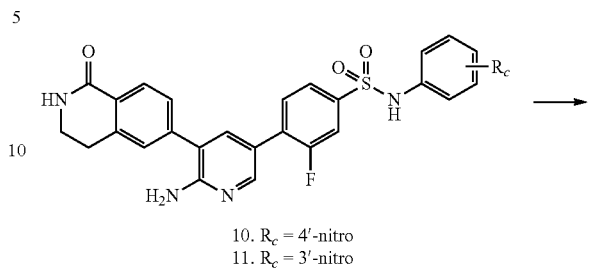

10. $R_c$ = 4'-nitro
11. $R_c$ = 3'-nitro

14. $R_c$ = 4'-amine
15. $R_c$ = 3'-amine

General Procedure of Reduction:

10 or 11 is reduced through hydrogenation to afford 14 or 15, respectively.

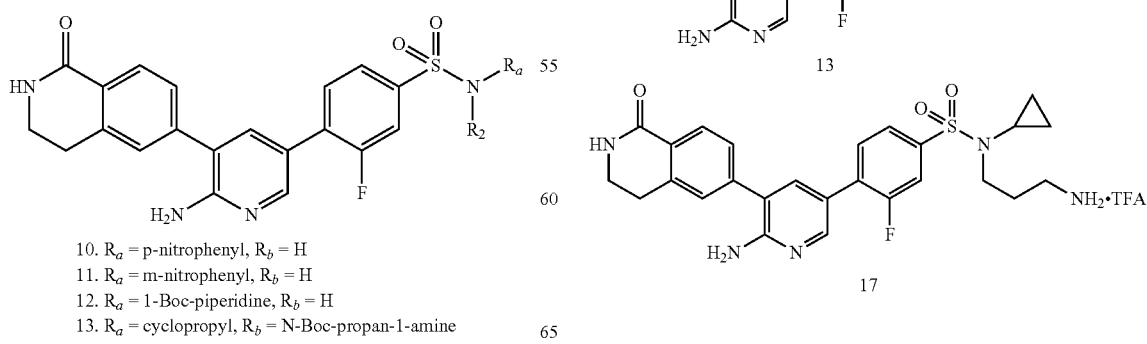

16 and 17 are generated from 12 and 13 under appropriated conditions (in the presence of DCM and TFA).

General Scheme 4

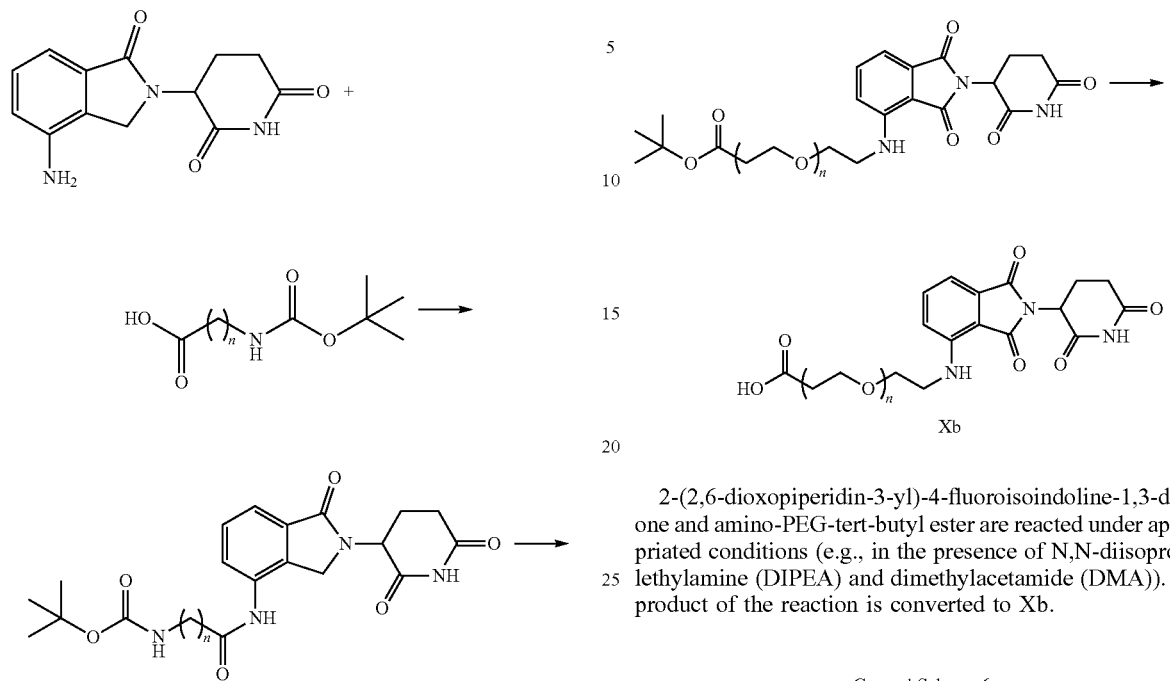

N-Boc amino acids is dissolved in an appropriate solvent (e.g., DMF) and reacted with lenalidomide under appropriate conditions (e.g., in the presence of HATU and Et₃N), the product of which is convened to Xa.

General Scheme 5

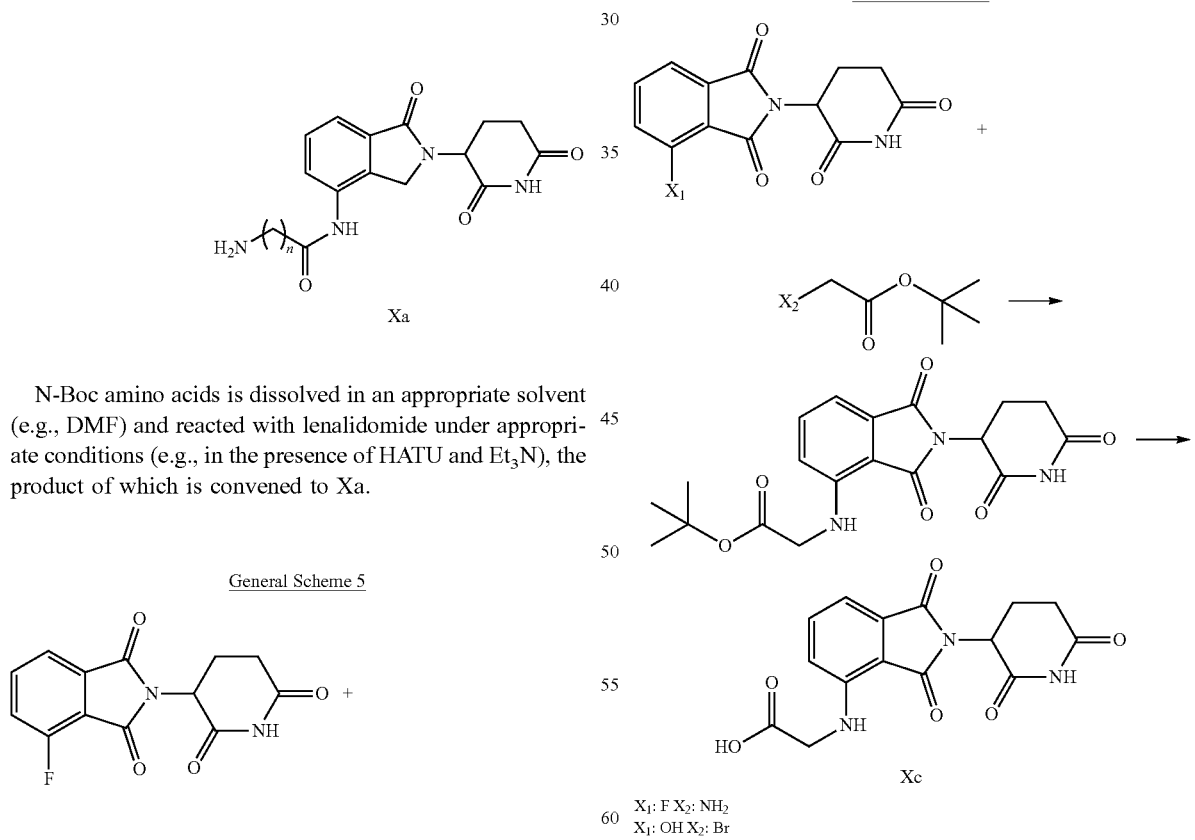

2-(2,6-dioxopiperidin-3-yl)-4-fluoroisoindoline-1,3-dione and amino-PEG-tert-butyl ester are reacted under appropriated conditions (e.g., in the presence of N,N-diisopropylethylamine (DIPEA) and dimethylacetamide (DMA)). The product of the reaction is converted to Xb.

General Scheme 6

$X_1$: F $X_2$: $NH_2$
$X_1$: OH $X_2$: Br

The starting materials are reacted under appropriated conditions (e.g., in the presence of N,N-diisopropylethylamine (DIPEA) and dimethylacetamide (DMA) or DMF and potassium carbonate). The product of the reaction is converted to Xc.

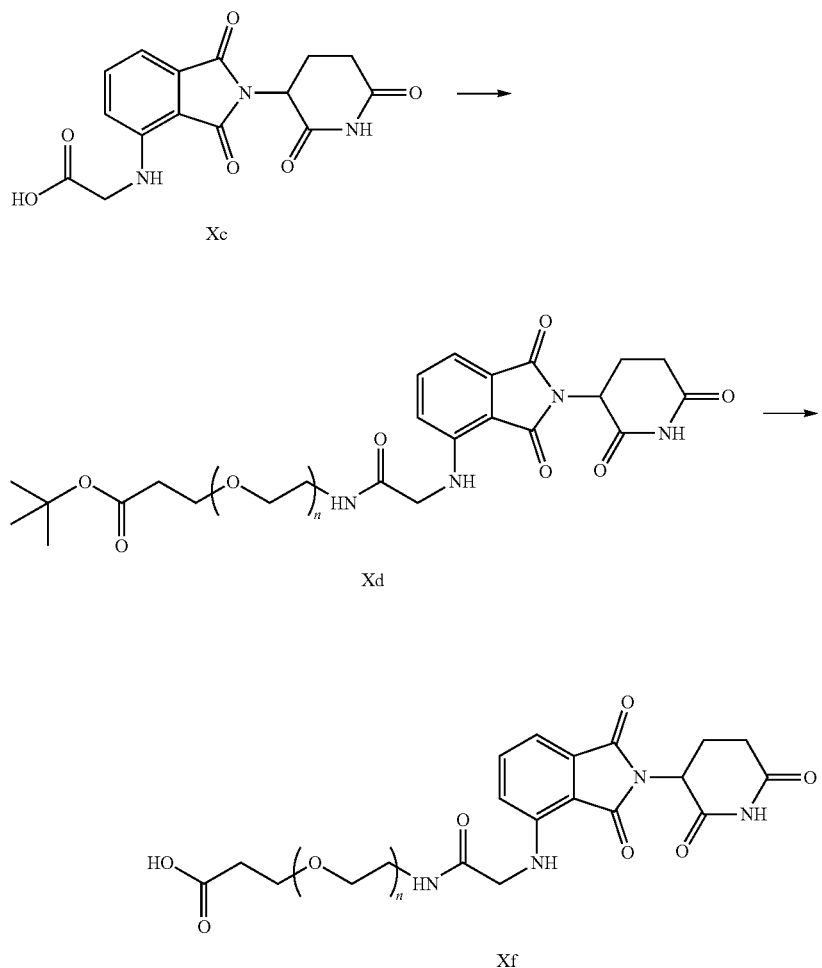

Xc is reacted with amino-PEG4-butyl ester to afford Xd, which is converted to Xr under appropriate conditions (e.g., in the presence of HCl in dioxane/water).

General Scheme 7

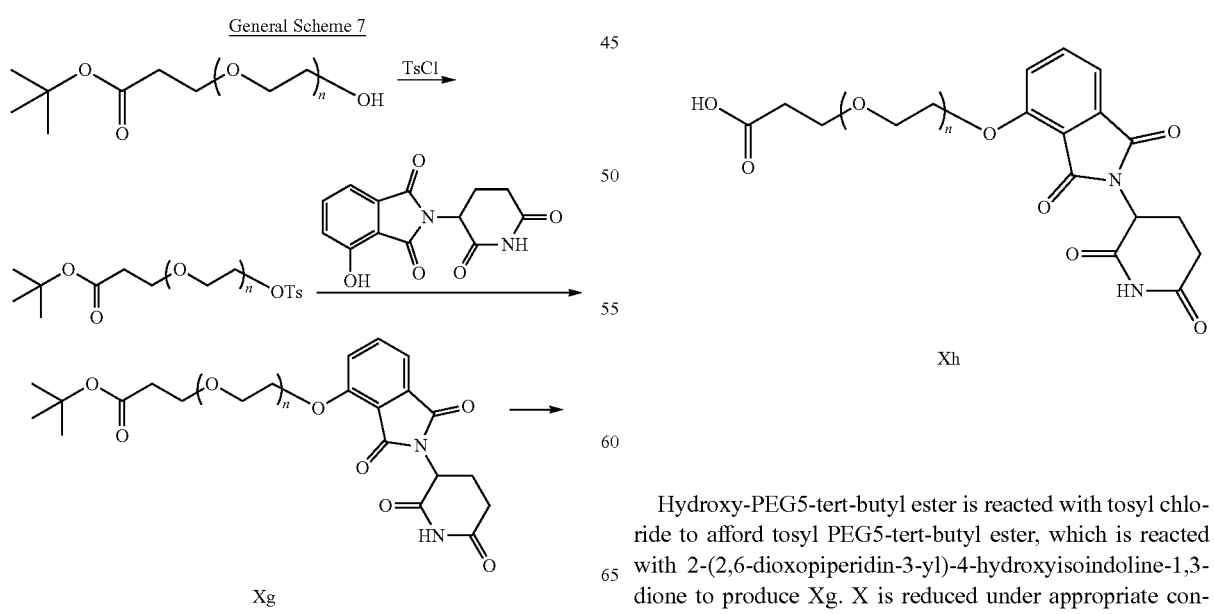

Hydroxy-PEG5-tert-butyl ester is reacted with tosyl chloride to afford tosyl PEG5-tert-butyl ester, which is reacted with 2-(2,6-dioxopiperidin-3-yl)-4-hydroxyisoindoline-1,3-dione to produce Xg. X is reduced under appropriate conditions to afford Xh.

General Scheme 8
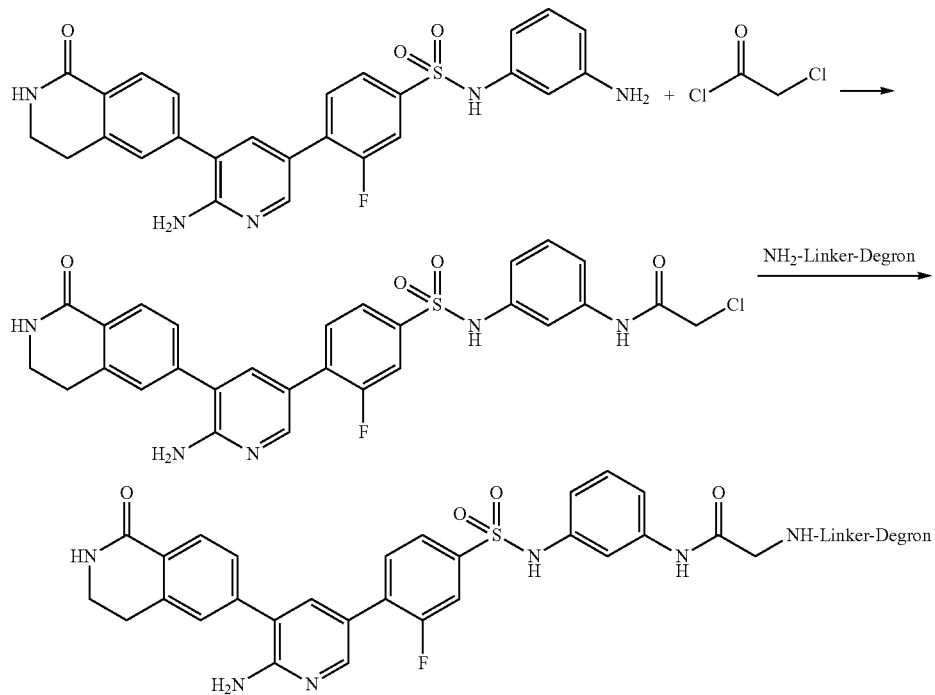
15 is mixed with chloroacetyl chloride, and the reaction is conducted under appropriate conditions (e.g., in the presence of THF and Et$_3$N) to afford the desired intermediate compound, which is reacted with NH$_2$-Linker-Degron to produce a compound of the application.
General Scheme 9
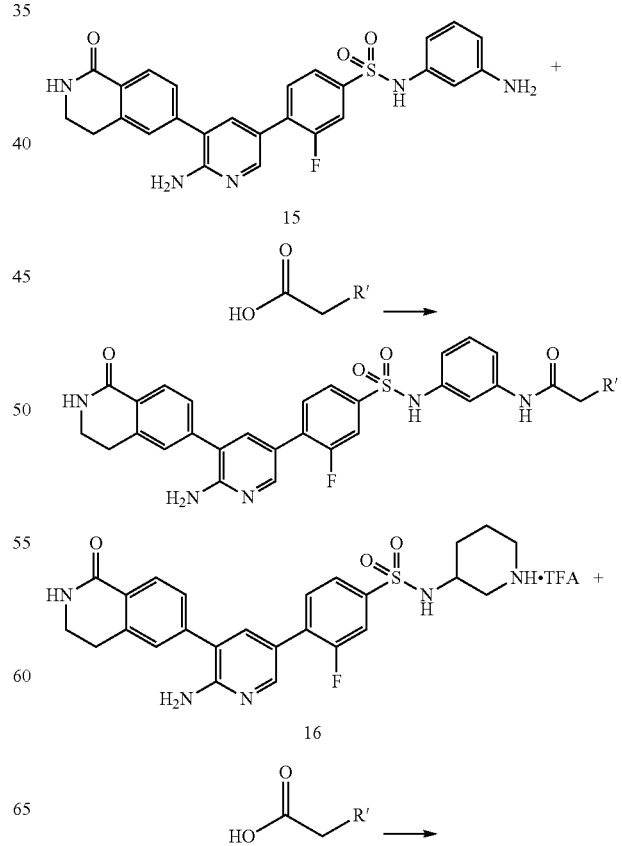

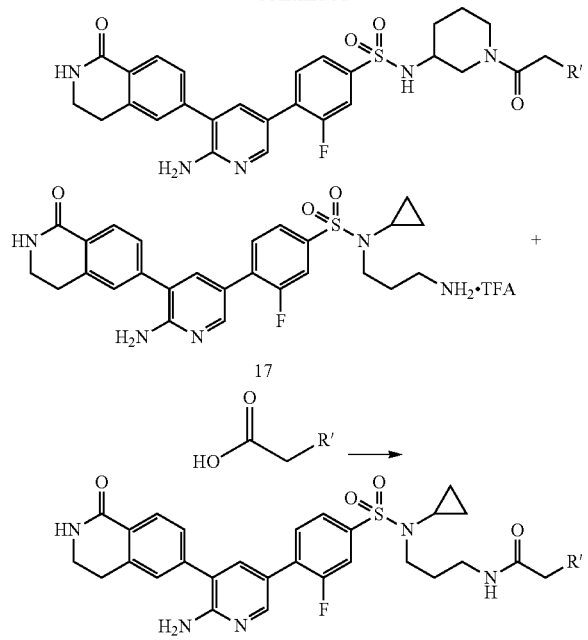

General Procedure of Peptidic Coupling.

A Targeting Ligand is added to a solution of PEG carboxylic acids. The reaction is carried out under appropriate conditions (e.g., in the presence of HATU in DMSO, amine, and TEA to afford a compound of the application.

Biological Assays

The biological activities of the compounds of the present application can be measured by various biochemical or cellular assays known to one of ordinary skill in the art. Non-limiting examples of biochemical and cellular assays are listed herein below.

Cell Proliferation Assays and Growth Assays

MM.1S, KMS20 and H929 MM cells are counted and diluted to a final concentration. The cell are plated and mixed with an equal volume of culture media containing DMSO or increasing concentration of a compound of the present application diluted in DMSO. Cells with increasing drug concentration and DMSO are then harvested at different time points. Viability is assessed by a cell proliferation assay.

Western Blotting

MM.1S, KMS20 and H929 cells are counted, diluted and plated. Cells are then harvested with DMSO or different concentration of a compound of the present application for 6 hrs, 24 hrs or 48 hrs. MM cells are then collected and centrifuged at RT and the pellets are re-suspended in lysis buffer. Cell lysates are subjected to sodium dodecyl sulfate-polyacrylamide gel electrophoresis SDS-PAGE, transferred to nitrocellulose membranes, and immunoblotted with different antibodies.

Apoptosis Assays

Apoptosis is quantified using Annexin-V-FITC-PI (propidium iodide) staining. In particular, cells are washed twice, resuspended in buffer, and stained with specific antibodies for 20 minutes. After adding additional binding buffer, samples are acquired and analyzed. The percentage of cells treated with a compound of the present application undergoing apoptosis is defined as the sum of early apoptotic and late apoptotic cells.

Methods of Use

Another aspect of the application provides a method of treating or preventing a disease or disorder, comprising administering to a subject in need thereof an effective amount of a compound of the present application, or a pharmaceutically acceptable salt, hydrate, solvate, prodrug, stereoisomer, or tautomer thereof. In one embodiment, the disease or disorder is mediated by STK4 (e.g., STK4 plays a role in the initiation or development of the disease or disorder). In one embodiment, the disease or disorder is cancer or a proliferation disease. In another embodiment, the disease or disorder is an autoimmune disease. In another embodiment, the disease or disorder is a metabolic disease. In one embodiment, the application provides a method of treating a disease or disorder. In one embodiment, the application provides a method of preventing a disease or disorder. In one embodiment, the disease or disorder is characterized by a reduced level of YAP1, as compared to the level of YAP1 in a control (e.g., a subject without the disease or disorder).

In another aspect, the application provides a method of treating or preventing a disease or disorder associated with the modulation of STK4, comprising administering to a subject in need thereof an effective amount of a compound of the present application, or a pharmaceutically acceptable salt, hydrate, solvate, prodrug, stereoisomer, or tautomer thereof. In one embodiment, the disease or disorder is cancer or a proliferation disease. In another embodiment, the disease or disorder is an autoimmune disease. In another embodiment, the disease or disorder is a metabolic disease. In one embodiment, the disease or disorder is characterized by a reduced level of YAP1, as compared to the level of YAP1 in a control (e.g., a subject without the disease or disorder).

In a further embodiment, the disease or disorder is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, or solid tumors. In a further embodiment, the cancer is multiple myeloma, leukemia, or lymphoma.

In another aspect, the application provides a method of treating or preventing cancer mediated by STK4 (e.g., STK4 plays a role in the initiation or development of the cancer), comprising administering to a subject in need thereof an effective amount of a compound of the present application, or a pharmaceutically acceptable salt, hydrate, solvate, prodrug, stereoisomer, or tautomer thereof. In one embodiment, the application provides a method of treating cancer. In one embodiment, the application provides a method of preventing cancer. In one embodiment, the cancer is characterized by a reduced level of YAP1, as compared to the level of YAP1 in a control (e.g., a subject without the cancer).

In a further embodiment, the cancer is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, or solid tumors. In a further embodiment, the cancer is multiple myeloma, leukemia, or lymphoma.

Another aspect of the application provides a method of treating or preventing a hematopoietic disorder, the method comprising administering, to a subject in need thereof an effective amount of a compound of the present application, or a pharmaceutically acceptable salt, hydrate, solvate, prodrug, stereoisomer, or tautomer thereof. In one embodiment, the application provides a method of treating a hematopoietic disorder. In one embodiment, the application provides a method of preventing a hematopoietic disorder. In one embodiment, the hematopoietic disorder is characterized by a reduced level of YAP1, as compared to the level of YAP1 in a control (e.g., a subject without the hematopoietic disorder).

In one embodiment, the hematopoietic disorder is myeloma, leukaemias including acute lymphoblastic leukemia (ALL), adult T cell leukemia (AIL), acute myeloblastic leukemia (AML), chronic lymphocytic leukemia (CLL) and chronic myeloid leukemia (CML), lymphomas including non-Hodgkin's lymphomas such as Waldestrom Macroglobulinemia, Burkitt lymphoma, Mantle cell lymphoma, diffuse large B cell lymphoma and follicular lymphoma, aplastic Anemia, myelodysplasia and related bone marrow failure syndromes, polycythemia vera, acute and chronic myeloid leukemia, malignancies of lymphoid cells, less common hematologic malignancies, or plasma cell disorders.

In one embodiment, the hematopoietic disorder is selected from the group consisting of multiple myeloma, leukemia, or lymphoma. In another embodiment, the hematopoietic disorder is multiple myeloma. In another embodiment, the hematopoietic disorder is leukemia. In another embodiment, the hematopoietic disorder is lymphoma.

Another aspect of the application provides a method of modulating (e.g., decreasing) the amount of STK4, comprising administering to a subject in need thereof an effective amount of a compound of the present application, or a pharmaceutically acceptable salt, hydrate, solvate, prodrug, stereoisomer, or tautomer thereof.

Another aspect of the application provides a method of modulating (e.g., increasing) the amount of YAP1, comprising administering to a subject in need thereof an effective amount of a compound of the present application, or a pharmaceutically acceptable salt, hydrate, solvate, prodrug, stereoisomer, or tautomer thereof.

Another aspect of the application relates to a compound of the present application, or a pharmaceutically acceptable salt, hydrate, solvate, prodrug, stereoisomer, or tautomer thereof, for treating or preventing a disease or disorder, such as cancer mediated by STK4 (e.g., STK4 plays a role in the initiation or development of the cancer).

Another aspect of the application relates to use of a compound of the present application, or a pharmaceutically acceptable salt, hydrate, solvate, prodrug, stereoisomer, or tautomer thereof, in the treatment or prevention of a disease or disorder, such as cancer mediated by STK4 (e.g., STK4 plays a role in the initiation or development of the cancer).

Another aspect of the application relates to use of a compound of the present application, or a pharmaceutically acceptable salt, hydrate, solvate, prodrug, stereoisomer, or tautomer thereof, in the manufacture of a medicament for the treatment or prevention of a disease or disorder, such as cancer mediated by STK4 (e.g., STK4 plays a role in the initiation or development of the cancer).

Another aspect of the application relates to a compound of the present application, or a pharmaceutically acceptable salt, hydrate, solvate, prodrug, stereoisomer, or tautomer thereof, for use in the treatment or prevention of a disease or disorder, such as cancer mediated by STK4 (e.g., STK4 plays a role in the initiation or development of the cancer).

Another aspect of the application relates to a compound of the present application, or a pharmaceutically acceptable salt, hydrate, solvate, prodrug, stereoisomer, or tautomer thereof, for use in the manufacture of a medicament for the treatment or prevention of a disease or disorder, such as cancer mediated by STK4 (e.g., STK4 plays a role in the initiation or development of the cancer).

In one embodiment, the application relates to treating or treatment. In one embodiment, the application relates to preventing or prevention.

In one embodiment, the disease or disorder is mediated by STK4 (e.g., STK4 plays a role in the initiation or development of the disease or disorder). In one embodiment, the disease or disorder is cancer or a proliferation disease. In another embodiment, the disease or disorder is an autoimmune disease. In another embodiment, the disease or disorder is a metabolic disease. In one embodiment, the disease or disorder is characterized by a reduced level of YAP1, as compared to the level of YAP1 in a control (e.g., a subject without the disease or disorder). In one embodiment, the disease or disorder is associated with modulation of STK4.

In a further embodiment, the disease or disorder is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, or solid tumors. In a further embodiment, the cancer is multiple myeloma, leukemia, or lymphoma.

Another aspect of the application relates to a compound of the present application, or a pharmaceutically acceptable salt, hydrate, solvate, prodrug, stereoisomer, or tautomer thereof, for treating or preventing a hematopoietic disorder.

Another aspect of the application relates to use of a compound of the present application, or a pharmaceutically acceptable salt, hydrate, solvate, prodrug, stereoisomer, or tautomer thereof, in the treatment or prevention of a hematopoietic disorder.

Another aspect of the application relates to use of a compound of the present application, or a pharmaceutically acceptable salt, hydrate, solvate, prodrug, stereoisomer, or tautomer thereof, in the manufacture of a medicament for the treatment or prevention of a hematopoietic disorder.

Another aspect of the application relates to a compound of the present application, or a pharmaceutically acceptable salt, hydrate, solvate, prodrug, stereoisomer, or tautomer thereof, for use in the treatment or prevention of a hematopoietic disorder.

Another aspect of the application relates to a compound of the present application, or a pharmaceutically acceptable salt, hydrate, solvate, prodrug, stereoisomer, or tautomer thereof, for use in the manufacture of a medicament for the treatment or prevention of a hematopoietic disorder.

In one embodiment, the application relates to treating or treatment. In one embodiment, the application relates to preventing or prevention.

In one embodiment, the hematopoietic disorder is myeloma, leukaemias including acute lymphoblastic leukemia (ALL), adult T cell leukemia (AIL), acute myeloblastic leukemia (AML), chronic lymphocytic leukemia (CLL) and chronic myeloid leukemia (CML), lymphomas including non-Hodgkin's lymphomas such as Waldestrom Macroglobulinemia, Burkitt lymphoma, Mantle cell lymphoma, diffuse large B cell lymphoma and follicular lymphoma, aplastic Anemia, myelodysplasia and related bone marrow failure syndromes, polycythemia vera, acute and chronic myeloid leukemia, malignancies of lymphoid cells, less common hematologic malignancies, or plasma cell disorders.

In one embodiment, the hematopoietic disorder is selected from the group consisting of multiple myeloma, leukemia, or lymphoma. In another embodiment, the hematopoietic disorder is multiple myeloma. In another embodiment, the hematopoietic disorder is leukemia. In another embodiment, the hematopoietic disorder is lymphoma.

Another aspect of the application relates to a compound of the present application, or a pharmaceutically acceptable salt, hydrate, solvate, prodrug, stereoisomer, or tautomer thereof, for modulating (e.g., decreasing) the amount of STK4 and/or modulating (e.g., increasing) the amount of YAP1.

Another aspect of the application relates to use of a compound of the present application, or a pharmaceutically acceptable salt, hydrate, solvate, prodrug, stereoisomer, or tautomer thereof, in the modulation (e.g., decrease) of the amount of STK4 and/or modulation (e.g., increase) of the amount of YAP1.

Another aspect of the application relates to use of a compound of the present application, or a pharmaceutically acceptable salt, hydrate, solvate, prodrug, stereoisomer, or tautomer thereof, in the manufacture of a medicament for the modulation (e.g., decrease) of the amount of STK4 and/or modulation (e.g., increase) of the amount of YAP1.

Another aspect of the application relates to a compound of the present application, or a pharmaceutically acceptable salt, hydrate, solvate, prodrug, stereoisomer, or tautomer thereof, for use in the modulation (e.g., decrease) of the amount of STK4 and/or modulation (e.g., increase) of the amount of YAP1.

Another aspect of the application relates to a compound of the present application, or a pharmaceutically acceptable salt, hydrate, solvate, prodrug, stereoisomer, or tautomer thereof, for use in the manufacture of a medicament for the modulation (e.g., decrease) of the amount of STK4 and/or modulation (e.g., increase) of the amount of YAP1.

One aspect of this application provides compounds that are useful for the treatment of diseases, disorders, and conditions characterized by excessive or abnormal cell proliferation. Such diseases include, but are not limited to, a proliferative or hyperproliferative disease. Examples of proliferative and hyperproliferative diseases include, without limitation, cancer. The term "cancer" includes, but is not limited to, the following cancers: breast; ovary; cervix; prostate; testis, genitourinary tract; esophagus; larynx, glioblastoma; neuroblastoma; stomach; skin, keratoacanthoma; lung, epidermoid carcinoma, large cell carcinoma, small cell carcinoma, lung adenocarcinoma; bone; colon; colorectal; adenoma; pancreas, adenocarcinoma; thyroid, follicular carcinoma, undifferentiated carcinoma, papillary carcinoma; seminoma; melanoma; sarcoma; bladder carcinoma; liver carcinoma and biliary passages; kidney carcinoma myeloid disorders; lymphoid disorders, Hodgkin's, hairy cells; buccal cavity and pharynx (oral), lip, tongue, mouth, pharynx; small intestine; colorectal, large intestine, rectum, brain and central nervous system; chronic myeloid leukemia (CML), and leukemia. The term "cancer" includes, but is not limited to, the following cancers: myeloma, lymphoma, or a cancer selected from gastric, renal, or and the following cancers: head and neck, oropharangeal, non-small cell lung cancer (NSCLC), endometrial, hepatocarcinoma, Non-Hodgkins lymphoma, and pulmonary.

The term "cancer" refers to any cancer caused by the proliferation of malignant neoplastic cells, such as tumors, neoplasms, carcinomas, sarcomas, leukemias, lymphomas and the like. For example, cancers include, but are not limited to, mesothelioma, leukemias and lymphomas such as cutaneous T-cell lymphomas (CTCL), noncutaneous peripheral T-cell lymphomas, lymphomas associated with human T-cell lymphotrophic virus (HTLV) such as adult T-cell leukemia-lymphoma (ATLL), B-cell lymphoma, acute non-lymphocytic leukemias, chronic lymphocytic leukemia, chronic myelogenous leukemia, acute myelogenous leukemia, lymphomas, and multiple myeloma, non-Hodgkin lymphoma, acute lymphatic leukemia (ALL), chronic lymphatic leukemia (CLL), Hodgkin's lymphoma, Burkitt lymphoma, adult T-cell leukemia lymphoma, acute-myeloid leukemia (AML), chronic myeloid leukemia (CML), or hepatocellular carcinoma. Further examples include myelodisplastic syndrome, childhood solid tumors such as brain tumors, neuroblastoma, retinoblastoma, Wilms' tumor, bone tumors, and soft-tissue sarcomas, common solid tumors of adults such as head and neck cancers (e.g., oral, laryngeal, nasopharyngeal and esophageal), genitourinary cancers (e.g., prostate, bladder, renal, uterine, ovarian, testicular), lung cancer (e.g., small-cell and non-small cell), breast cancer, pancreatic cancer, melanoma and other skin cancers, stomach cancer, brain tumors, tumors related to Gorlin's syndrome (e.g., medulloblastoma, meningioma, etc.), and liver cancer. Additional exemplary forms of cancer which may be treated by the subject compounds include, but are not limited to, cancer of skeletal or smooth muscle, stomach cancer, cancer of the small intestine, rectum carcinoma, cancer of the salivary gland, endometrial cancer, adrenal cancer, anal cancer, rectal cancer, parathyroid cancer, and pituitary cancer.

Additional cancers that the compounds described herein may be useful in preventing, treating and studying are, for example, colon carcinoma, familiary adenomatous polyposis carcinoma and hereditary non-polyposis colorectal cancer, or melanoma. Further, cancers include, but are not limited to, labial carcinoma, larynx carcinoma, hypopharynx carcinoma, tongue carcinoma, salivary gland carcinoma, gastric carcinoma, adenocarcinoma, thyroid cancer (medullary and papillary thyroid carcinoma), renal carcinoma, kidney parenchyma carcinoma, cervix carcinoma, uterine corpus carcinoma, endometrium carcinoma, chorion carcinoma, testis carcinoma, urinary carcinoma, melanoma, brain tumors such as glioblastoma, astrocytoma, meningioma, medulloblastoma and peripheral neuroectodermal tumors, gall bladder carcinoma, bronchial carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing sarcoma, and plasmocytoma. In one aspect of the application, the present application provides for the use of one or more compounds of the application in the manufacture of a medicament for the treatment of cancer, including without limitation the various types of cancer disclosed herein.

In one embodiment, the compounds of this application are useful for treating cancer, such as colorectal, thyroid, breast, and lung cancer; and myeloproliferative disorders, such as polycythemia vera, thrombocythemia, myeloid metaplasia with myelofibrosis, chronic myelogenous leukemia, chronic myelomonocytic leukemia, hypereosinophilic syndrome, juvenile myelomonocytic leukemia, and systemic mast cell disease. In one embodiment, the compounds of this application are useful for treating hematopoietic disorders, in particular, acute-myelogenous leukemia (AML), chronic-myelogenous leukemia (CML), acute-promyelocytic leukemia, and acute lymphocytic leukemia (ALL).

This application further embraces the treatment or prevention of cell proliferative disorders such as hyperplasias, dysplasias and pre-cancerous lesions. Dysplasia is the earliest form of pre-cancerous lesion recognizable in a biopsy by a pathologist. The subject compounds may be administered for the purpose of preventing said hyperplasias, dysplasias or pre-cancerous lesions from continuing to expand or from becoming cancerous. Examples of pre-cancerous lesions may occur in skin, esophageal tissue, breast and cervical intraepithelial tissue.

For any of the above methods and uses, the required dosage will vary depending on the mode of administration, the particular condition to be treated, and the effect desired.

Compounds of the application can be administered in therapeutically effective amounts in a combinational therapy with one or more therapeutic agents (pharmaceutical combinations) or modalities, e.g., non-drug therapies. For example, synergistic effects can occur with other anti-proliferative, anti-cancer, immunomodulatory or anti-inflammatory substances. Where the compounds of the application are administered in conjunction with other therapies, dosages of the co-administered compounds will of course vary depending on the type of co-drug employed, on the specific drug employed, on the condition being treated and so forth.

Combination therapy includes the administration of the subject compounds in further combination with other biologically active ingredients (such as, but not limited to, a second and different antineoplastic agent) and non-drug therapies (such as, but not limited to, surgery or radiation treatment). For instance, the compounds of the application can be used in combination with other pharmaceutically active compounds, preferably compounds that are able to enhance the effect of the compounds of the application. The compounds of the application can be administered simultaneously (as a single preparation or separate preparation) or sequentially to the other drug therapy or treatment modality. In general, a combination therapy envisions administration of two or more drugs during a single cycle or course of therapy.

In one aspect of the application, the compounds of the application may be administered in combination with one or more separate agents that modulate protein kinases involved in various disease states. In another aspect of the application, the subject compounds may be administered in combination with one or more agents that modulate non-kinase biological targets or processes.

In one aspect of the application, the compounds of the application are administered in combination with a chemotherapeutic agent. In certain embodiments, the compounds of the application are administered in combination with a chemoprotective agent.

In one aspect of the application, the subject compounds are administered in combination with radiation therapy. In one aspect of the application, the subject compounds are administered in combination with an immunotherapeutic agent.

It will be appreciated that the compounds of the application may advantageously be used in conjunction with one or more adjunctive therapeutic agents. Examples of suitable agents for adjunctive therapy include a $5HT_1$ agonist, such as a triptan (e.g., sumatriptan or naratriptan); an adenosine A1 agonist; an EP ligand; an NMDA modulator, such as a glycine antagonist; a sodium channel blocker (e.g., lamotrigine); a substance P antagonist (e.g., an $NK_1$ antagonist); a cannabinoid; acetaminophen or phenacetin; a 5-lipoxygenase inhibitor; a leukotriene receptor antagonist; a DMARD (e.g., methotrexate); gabapentin and related compounds; a tricyclic antidepressant (e.g., amitryptilline); a neuron stabilizing antiepileptic drug; a mono-aminergic uptake inhibitor (e.g., venlafaxine); a matrix metalloproteinase inhibitor; a nitric oxide synthase (NOS) inhibitor, such as an iNOS or an nNOS inhibitor; an inhibitor of the release, or action, of tumor necrosis factor α; an antibody therapy, such as a monoclonal antibody therapy; an antiviral agent, such as a nucleoside inhibitor (e.g., lamivudine) or an immune system modulator (e.g., interferon); an opioid analgesic; a local anesthetic; a stimulant, including caffeine; an H2-antagonist (e.g., ranitidine); a proton pump inhibitor (e.g., omeprazole); an antacid (e.g., aluminum or magnesium hydroxide; an antiflatulent (e.g., simethicone); a decongestant (e.g., phenylephrine, phenylpropanolamine, pseudoephedrine, oxymetazoline, epinephrine, naphazoline, xylometazoline, propylhexedrine, or levo-desoxyephedrine); an antitussive (e.g., codeine, hydrocodone, carmiphen, carbetapentane, or dextramethorphan); a diuretic; or a sedating or non-sedating antihistamine.

In general, compounds of the application will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g., humans, is in the range from about 0.5 mg to about 100 mg, conveniently administered, e.g., in divided doses up to four times a day or in retard form. Suitable unit dosage forms for oral administration comprise from ca. 1 to 50 mg active ingredient.

In one embodiment, a therapeutic amount or dose of the compounds of the present application may range from about 0.1 mg/Kg to about 500 mg/Kg, alternatively from about 1 to about 50 mg/Kg. In general, treatment regimens according to the present application comprise administration to a patient in need of such treatment from about 10 mg to about 1000 mg of the compound(s) of this application per day in single or multiple doses. Therapeutic amounts or doses will also vary depending on route of administration, as well as the possibility of co-usage with other agents.

Upon improvement of a subject's condition, a maintenance dose of a compound, composition or combination of this application may be administered, if necessary. Subsequently, the dosage or frequency of administration, or both, may be reduced, as a function of the symptoms, to a level at which the improved condition is retained when the symptoms have been alleviated to the desired level, treatment should cease. The subject may, however, require intermittent treatment on a long-term basis upon any recurrence of disease symptoms.

It will be understood, however, that the total daily usage of the compounds and compositions of the present application will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g., a compound of the application and a co-agent, are both administered to a patient simultaneously in the form of a single entity or dosage. The term "non-fixed combination" means that the active ingredients, e.g., a compound of the application and a co-agent, are both administered to a patient as separate entities either simultaneously, concurrently or sequentially with no specific time limits, wherein such administration provides therapeutically effective levels of the two compounds in the body of the patient. The latter also applies to cocktail therapy, e.g., the administration of three or more active ingredients.

Pharmaceutical Compositions

In another aspect, the application provides a pharmaceutical composition comprising a compound of the present application, or a pharmaceutically acceptable ester, salt, or prodrug thereof, together with a pharmaceutically acceptable carrier.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylenepolyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes, oils such as peanut oil, cottonseed oil; safflower oil; sesame oil; olive oil; corn oil and soybean oil; glycols; such a propylene glycol or polyethylene glycol; esters such as ethyl oleate and ethyl laurate, agar; buffering agents such as magnesium hydroxide and aluminum hydroxide; alginic acid; pyrogen-free water, isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The compounds or pharmaceutical salts thereof may be formulated into pharmaceutical compositions for administration to animals or humans. These pharmaceutical compositions, which comprise an amount of the inhibitor effective to treat or prevent a kinase-mediated condition and a pharmaceutically acceptable carrier, are another embodiment of the present application.

Compounds of the application can be administered as pharmaceutical compositions by any conventional route, in particular enterally, e.g., orally. e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a compound of the present application in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present application with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application. e.g., to the skin and eyes, are preferably aqueous solutions, ointments, creams or gels well-known in the art. Such may contain solubilizers, stabilizers, tonicity enhancing agents, buffers and preservatives.

The pharmaceutical compositions of the present application comprise a therapeutically effective amount of a compound of the present application formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. The pharmaceutical compositions of this application can be administered to humans and other animals orally, rectally, parenterally, intracistemally, intravaginally, intraperitoneally, topically (as by powders, ointments, or drops), buccally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

In order to prolong the effect of a drug, it is often desirable to slow the absorption of the drug from subcutaneous or intramuscular injection, his may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are preferably suppositories which can be prepared by mixing the compounds of this application with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid compositions of a similar type may also be employed as fillers in soft and hard filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

Dosage forms for topical or transdermal administration of a compound of this application include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this application.

The ointments, pastes, creams and gels may contain, in addition to an active compound of this application, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this application, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The application also provides for a pharmaceutical combinations, e.g., a kit, comprising a) a first agent which is a compound of the application as disclosed herein, in free form or in pharmaceutically acceptable salt form, and b) at least one co-agent. The kit can comprise instructions for its administration.

The application is further illustrated by the following examples and synthesis schemes, which are not to be construed as limiting this application in scope or spirit to the specific procedures herein described. It is to be understood that the examples are provided to illustrate one embodiment and that no limitation to the scope of the application is intended thereby. It is to be further understood that resort may be had to various another embodiment, modifications, and equivalents thereof which may suggest themselves to those skilled in the art without departing from the spirit of the present application and/or scope of the appended claims.

EXAMPLES

Analytical Methods, Materials, and Instrumentation

All commercially available starting materials were purchased from Sigma Aldrich, Fisher Scientific, Oakwood Chemical and Combi Block. All reagents were used as received without further purification. Known compounds were synthesized according to published literature procedures and any modifications are noted. Anhydrous solvents, such as tetrahydrofuran (THF), diethyl ether, dichloromethane (DCM), dimethyl formamide (DMF), dimethylsulfoxide (DMSO), 1,4-dioxane, and toluene (PhMe) were purchased from Fisher Scientific, and used as received. If necessary, air or moisture sensitive reactions were carried out under an inert atmosphere of nitrogen.

Removal of solvents was accomplished on a Büchi R-300 rotary evaporator and further concentration was done under a Welch 1400B-01 vacuum line, and Labconco FreeZone 6 plus system. Purification of compounds was performed by normal phase column chromatography using Teledyne CombiFlash chromatography system, and/or reversed phase chromatography on Waters Micromass ZQ preparative system with SunFire® Prep C18 OBD™ 5 µM column. The purity was analyzed on Waters Acquity UPLC system. Analytical thin layer chromatography (TLC) plates were purchased from Fisher Scientific (EMD Millipore TLC Silica Gel60 F254). Visualization was accomplished by irradiation under UV light (254 nm).

All $^1$H-NMR spectra were recorded at 298K on a Bruker ARX 500 (500 MHz) spectrometer. $^{13}$C-NMR spectra were recorded on a Bruker ARX 500 (125 MHz) spectrometer. Samples were dissolved in CDCl3 or DMSO-d6. The spectra were referenced to the residual solvent peak (chlorofrom-d: 7.26 ppm for $^1$H-NMR and 77.16 ppm for C-NMR; DMSO-d6: 2.50 ppm for $^1$H-NMR and 39.52 ppm for $^{13}$C-NMR CD$_3$OD: 3.31 ppm for $^1$H NMR and 49.00 ppm for $^{13}$C NMR or tetramethylsilane (TMS) as the internal standard. Chemical shift, multiplicity (s=singlet, d=doublet, t=triplet, q=quartet, m=multiplet, br=broad peak), coupling constants (Hz), and number of protons. Mass spectrometry data were obtained on Waters Acquity UPLC system in positive ESI mode.

Abbreviations used in the following examples and elsewhere herein are:

- atm atmosphere
- br broad
- (BPin)$_2$ Bis(pinacolato)diboron
- DIPEA N,N-diisopropylethylamine
- dppf 1,1'-bis(diphenylphosphino)ferrocene
- DCM dichloromethane
- DMA N,N-dimethylacetamide
- DMF N,N-dimethylformamide
- EDCI N-(3-Dimethylaminopropyl)-N-ethylcarbodiimide hydrochloride
- ESI electrospray ionization
- h hour(s)
- HOB$_t$ hydroxybenzotriazole
- HPLC high-performance liquid chromatography
- KOAc Potassium Acetate
- LCMS liquid chromatography-mass spectrometry
- m multiplet
- MeI methyl iodide
- MHz megahertz
- min minutes
- NBS N-bromosuccinimide
- NIS N-iodosuccinimide
- NMR nuclear magnetic resonance
- ppm parts per million
- Py pyridine
- TEA triethylamine
- TFAA trifluoroacetic anhydride
- TLC thin layer chromatography Example 1: General Procedures

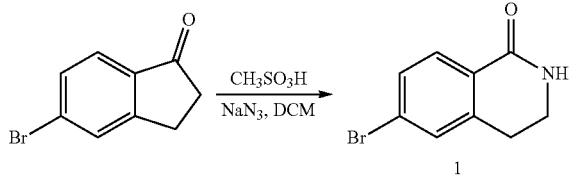

I-1. 6-bromo-3,4-dihydroisoquinolin-1(2H)-one

Under N$_2$ atmosphere, to a solution of 5-bromo-2,3-dihydro-1H-inden-1-one (10 g, 47.39 mmol) and methanesulfonic acid (45.5 g, 473.93 mmol) in DCM (75 mL) was added NaN$_3$ (6.2 g, 94.79 mmol) slowly in portions at −5~0° C. with stirring. After the addition was completed, the mixture was kept at 0° C. for 3 hours. The reaction mixture was adjusted to pH=10 with 20% NaOH aqueous solution and extracted with DCM. The combined organic layers were washed with water three times and then with brine, dried over MgSO$_4$, filtered and concentrated. The residue was purified by flash column chromatography (0% to 70% EtOAc in hexanes) to afford 6.9 g product in 66% yield. LCMS (ESI) m/z 226.08 [(M+H)$^+$; calcd for C$_9$H$_8$BrNO$^+$; 226.07].

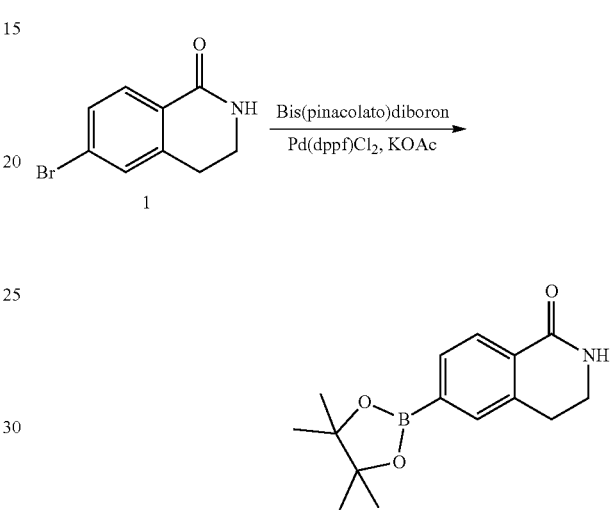

I-2. 6-(4,4,5,5-tetramethyl-1,3,2-dioxaborolan-2-yl)-3,4-dihydroisoquinolin-1(2H)-one Under N$_2$ atmosphere, a mixture of 1 (3.4 g, 15.0 mmol), bis(pinacolato)diboron (5.73 g, 22.5 mmol), potassium acetate (2.95 g, 30.0 mmol) and Pd(dppf)Cl$_2$ (1.1 g, 1.5 mmol) in dioxane (75 mL) was heated at 85° C. for 20 hours. The mixture was concentrated and the residue was purified by flash column chromatography (0% to 80% EtOAc in hexanes) to afford 3.4 g product in 83% yield. LCMS (ESI) m/z 274.28 [(M+H)$^+$; calcd for C$_{15}$H$_{21}$BNO$_3^+$: 274.16].

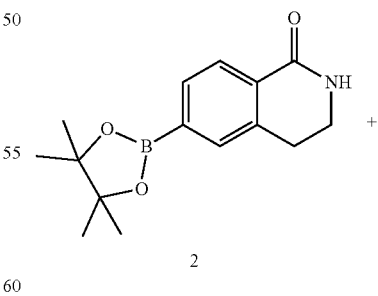

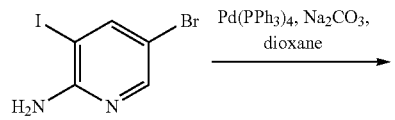

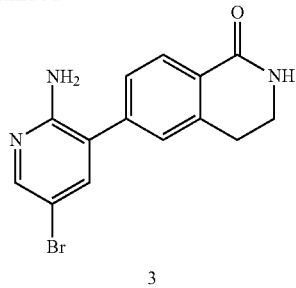

3

I-3. 6-(2-amino-5-bromopyridin-3-yl)-3,4-dihydroisoquinolin-1(2H)-one

Under $N_2$ atmosphere, a mixture of 2 (3.4 g, 12.45 mmol), 5-bromo-3-iodopyridin-2-amine (4.5 g, 14.95 mmol), sodium carbonate (2.64 g, 24.9 mmol) and Pd(PPh$_3$)$_4$ (1.44 g, 1.25 mmol) in dioxane (80 mL) and water (10 mL) was heated at 70° C. for 64 hours. The mixture was concentrated and the residue was purified by flash column chromatography (0% to 25% MeOH in DCM) to afford 2.1 g product in 53% yield. LCMS (ESI) m/z 318.18 [(M+H)$^+$; calcd for C$_{14}$H$_{12}$BrN$_3$O$^+$: 318.17].

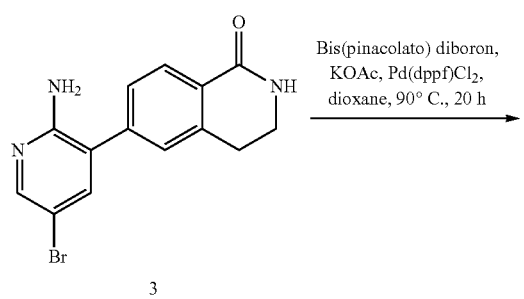

I-4. 6-(2-amino-5-(4,4,5,5-tetramethyl-1,3,2-dioxaborolan-2-yl)pyridin-3-yl)-3,4-dihydroisoquinolin-1(2H)-one Under $N_2$ atmosphere, a mixture of 3 (1 g, 3.14 mmol), bis(pinacolato)diboron (1.2 g, 4.72 mmol), potassium acetate (616 mg, 6.29 mmol) and Pd(dppf)Cl$_2$ (230 mg, 0.31 mmol) in dioxane (30 mL) was heated at 90° C. for 20 hours. The mixture was concentrated. The residue was dissolved in DCM and washed with water two times and then with brine, dried over MgSO$_4$, filtered and concentrated to afford 2 g crude product, which was used in next step without further purification.

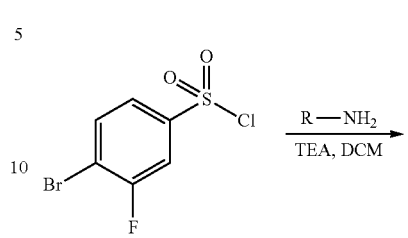

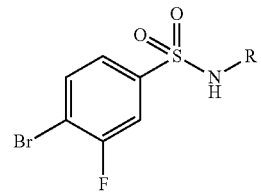

5. R = p-nitrophenyl
6. R = m-nitrophenyl
7. R = 1-Boc-piperidine
8. R = cyclopropyl

II-1. Intermediates 5, 6, 7, and 8

Method A for 5 and 6:

A solution of 3-nitroaniline (708 mg, 5.13 mmol) and 4-bromo-3-fluorobenzenesulfonyl chloride (1.68 g, 6.16 mmol) in pyridine (6 mL) was heated at 70° C. for 5 hours. The mixture was cooled to room temperature. The mixture was poured into ice-water and extracted with EtOAc three times. The combined organic layers were sequentially washed with 15% citric acid aqueous solution, water and brine, then dried over MgSO$_4$, filtered and concentrated. The residue was triturated with diethyl ether and filtered. The filtrate was concentrated and triturated with hexanes and then filtered. The filtered cake was washed with hexanes and dried in vacuo to afford 1.4 g product in 88% yield.

Method B for 7 and 8:

A solution of 4-bromo-3-fluorobenzenesulfonyl chloride (547 mg, 2.0 mmol) in DCM (5 mL) was added dropwise to a stirring solution of cyclopropanamine (148 mg, 2.6 mmol) and TEA (0.834 mL, 6.0 mmol) in DCM (15 mL) at 5-10° C. After the addition was completed, the mixture was warmed up to room temperature and stirred for 1 hour. The mixture was concentrated and the residue was purified by flash column chromatography (0% to 30% EtOAc in hexanes) to afford 540 mg product in 92% yield 7: LCMS (ESI) m/z 336.98 [(M-100)$^+$; calcd for C$_{16}$H$_{22}$BrFN$_2$O$_4$S$^+$: 437.32] or 8: LCMS (ESI) m/z 293.98 [(M+H)$^+$; calcd for C$_9$H$_9$BrFNO$_2$S$^+$: 294.14].

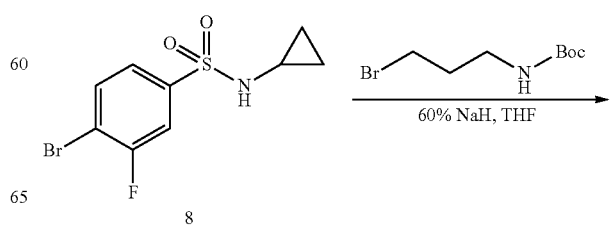

8

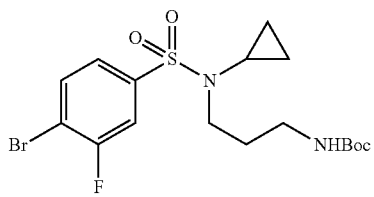

9

II-2. tert-butyl (3-((4-bromo-N-cyclopropyl-3-fluorophenyl)sulfonamido)propyl) carbamate Under $N_2$ atmosphere, to a stirring suspension of 60% NaH in dry THF (2 mL) was added dropwisely a solution of 8 (500 mg, 1.7 mmol) in dry THF (5 mL) at 5-10° C. After the addition was completed, the mixture was warmed up to room temperature and stirred for 20 min. A solution of tert-butyl (3-bromopropyl)carbamate (607 mg, 2.55 mmol) in dry THF was added to above mixture. Then the mixture was heated at 55° C. overnight. The mixture was quenched with saturated $NH_4Cl$ aqueous solution and extracted with EtOAc. The combined organic layers were washed with water and brine, dried over $MgSO_4$, filtered and concentrated. The residue was purified by flash column chromatography (0% to 30% EtOAc in hexanes) to afford 440 mg product in 58% yield. LCMS (ESI) m/z 351.07 [(M−100)$^+$; calcd for $C_{17}H_{24}BrFN_2O_4S^+$: 451.35].

III-1. Intermediates 10, 11, 12, and 13

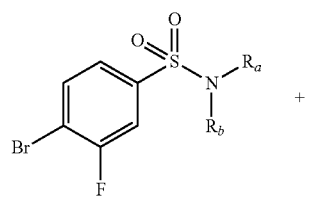

5. $R_a$ = p-nitrophenyl, $R_b$ = H
6. $R_a$ = m-nitrophenyl, $R_b$ = H
7. $R_a$ = 1-Boc-piperidine, $R_b$ = H
9. $R_a$ = cyclopropyl,
$R_b$ = N-Boc-propan-1-amine

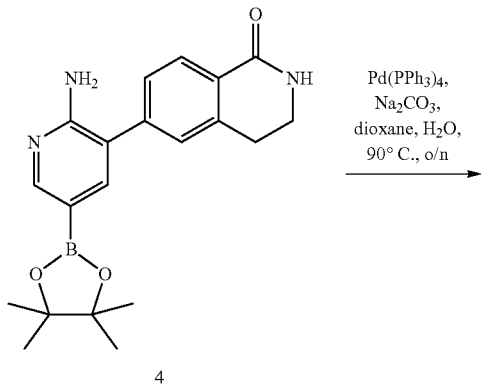

4

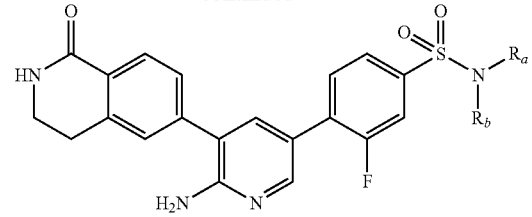

10. $R_a$ = p-nitrophenyl, $R_b$ = H
11. $R_a$ = m-nitrophenyl, $R_b$ = H
12. $R_a$ = 1-Boc-piperidine, $R_b$ = H
13. $R_a$ = cyclopropyl, $R_b$ = N-Boc-propan-1-amine General Procedure of Suzuki Coupling:

Under $N_2$ atmosphere, a mixture of 4 (1 g*58%, crude, 1.58 mmol), 5, 6, 7, 9 (1.1 eq), sodium carbonate (2.0 eq) and $Pd(PPh_3)_4$ (0.1 eq) in dioxane (20 mL) and water (4 mL) was heated at 90° C. overnight. The mixture was concentrated and the residue was purified by flash column chromatography to afford product: 10: LCMS (EST) m/z 534.21 [(M+H)$^+$; calcd for $C_{26}H_{20}FN_5O_8S^+$: 533.53], 11: LCMS (ESI) m/z 534.21 [(M+H)$^+$; calcd for $C_{26}H_{20}FN_8O_5S^+$: 533.53], 12: LCMS (ESI) m/z 617.23 [(M+Na)$^+$; calcd for $C_{30}H_{34}FN_5O_5S^+$: 595.69], or 13: LCMS (ESI) m/z 609.89 [(M+H)$^+$; calcd for $C_{31}H_{36}FN_5O_5S^+$: 609.72].

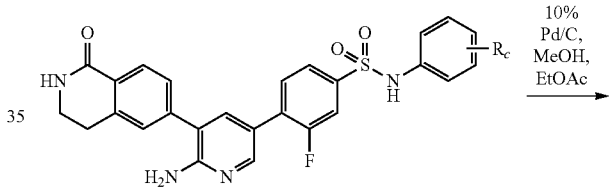

10. $R_c$ = 4'-nitro
11. $R_c$ = 3'-nitro

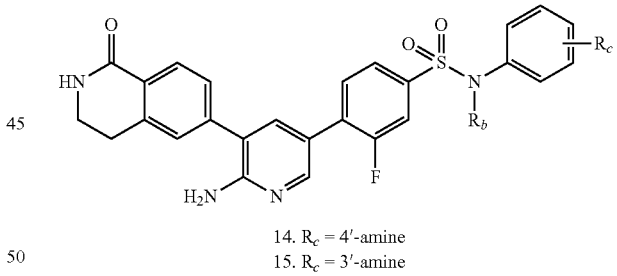

14. $R_c$ = 4'-amine
15. $R_c$ = 3'-amine

III-2. Intermediates 14 and 15

General Procedure of Reduction:

A mixture of 11 (580 mg, 1.09 mmol) and 10% palladium on activated carbon (290 mg) in MeOH (30 mL) and EtOAc (30 mL) was hydrogenated with a hydrogen balloon at 40° C. for 3 hours. The reaction mixture was cooled to room temperature and filtered. The filtrate was concentrated to afford 14 or 15 (490 mg in 90% yield), which was used in next step without further purification: 14: LCMS (EST) m/z 504.31 [(M+H)$^+$; calcd for $C_{26}H_{22}FN_5O_3S^+$: 503.55], and 15: LCMS (ESI) m/z 504.31 [(M+H)$^+$; calcd for $C_{26}H_{22}FN_5O_3S^+$: 503.55].

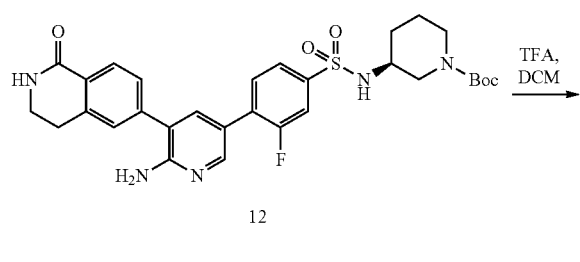

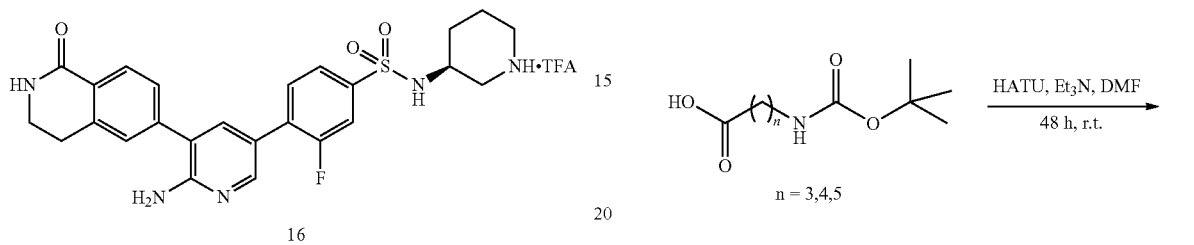

IV-1

III-3. Intermediate 16

To a solution of 12 (35 mg, 0.0588 mmol) in DCM (2 mL) was added TFA (1 mL). The mixture was stirred at room temperature for 1 hour. The mixture was concentrated and dried in vacuo to afford 16 (40 mg product), which was used in next step directly. LCMS (ESI) m/z 496.38 [(M+H)$^+$; calcd for $C_{25}H_{26}FN_5O_3S^+$: 495.57].

III-4. Intermediate 17

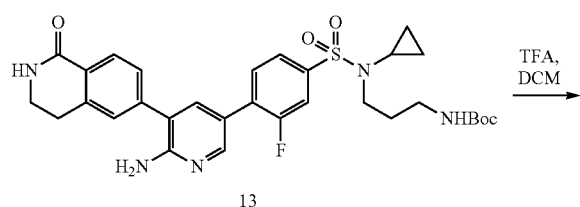

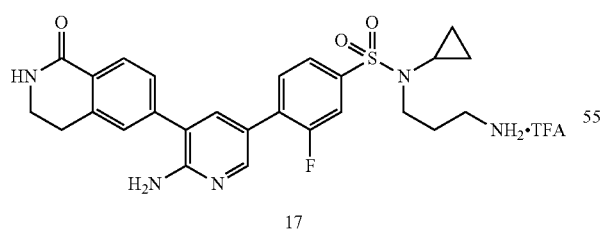

To a solution of 13 (18 mg, 0.0296 mmol) in DCM (1 mL) was added TFA (0.5 mL). The mixture was stirred at room temperature for 30 min. The mixture was concentrated and dried in vacuo to afford 17 (21 mg product), which was used in next step directly. LCMS (ESI) m/z 510.28 [(M+H)$^+$; calcd for $C_{26}H_{28}FN_5O_3S^+$: 509.60].

N-Boc amino acids (1 mmol) was dissolved in 3 mL dimethylformamide (DMF). HATU (0.57g, 1.5 mmol) and Et$_3$N (0.28 mL, 2.0 mmol) were added into the solution. The solution was stirred for 10 min at r.t. before lenalidomide (0.26g, 1.0 mmol) was introduced. The reaction was stirred at r.t. for 48 hours. Then it was diluted with EtOAc, washed with brine twice. The aqueous solution was extracted with EtOAc. The combined organic layer was dried over MgSO$_4$, filtered, and evaporated under reduced pressure. The crude materials were then subjected to normal phase chromatography using CombiFlash Rf+ system (10% to 50% MeOH in EtOAc), then reverse phase HPLC (MeCN/H$_2$O w/0.5‰ TFA) to afford purified products as off-white solid (n=3, 78%; n=4, 80%; n=5, 69%).

LCMS (ESI) m/z 345.28 (shown as free amine (—NH$_2$) instead of —NHBoc) [(M+H)$^+$; calcd for $C_{22}H_{29}N_4O_6^+$: 445.21]

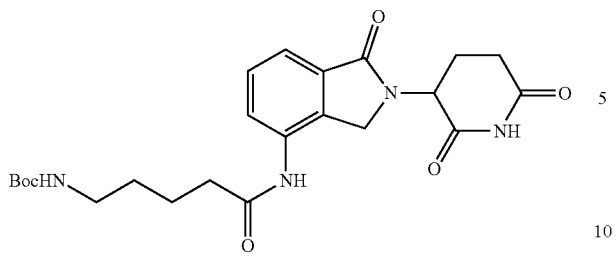

LCMS (ESI) m/z 359.28 (shown as free amine (—NH$_2$) instead of —NHBoc) [(M+H)$^+$; calcd for C$_{23}$H$_{31}$N$_4$O$_6^+$: 459.22]

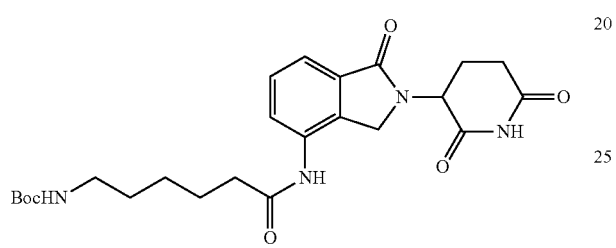

LCMS (ESI) m/z 373.28 (shown as free amine (—NH$_2$) instead of —NHBoc) [(M+H)$^+$; calcd for C$_{24}$H$_{33}$N$_4$O$_6^+$: 473.24]

IV-2

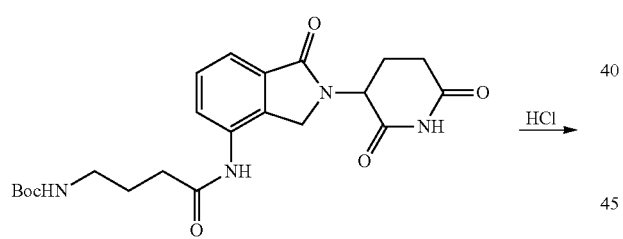

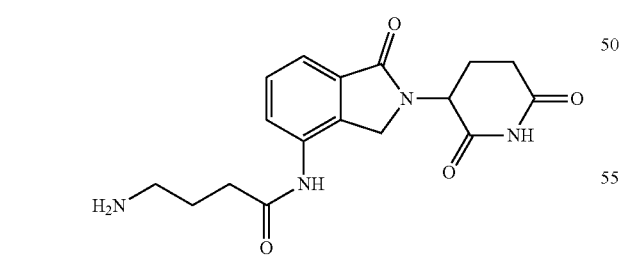

tert-butyl (4-((2-(2,6-dioxopiperidin-3-yl)-1-oxoisoindolin-4-yl)amino)-4-oxobutyl)carbamate (0.15g, 0.33 mmol) was dissolved in 2 mL 4M HCl dioxane/H$_2$O solution, stirred at room temperature for 2 hours. Then the mixture was concentrated under reduced pressure to afford off-white solid, which was used directly in following steps without further purification. LCMS (ESI) m/z 359.28 [(M+H)$^+$; calcd for C$_{18}$H$_{23}$N$_4$O$_4^+$: 359.17]

V-1

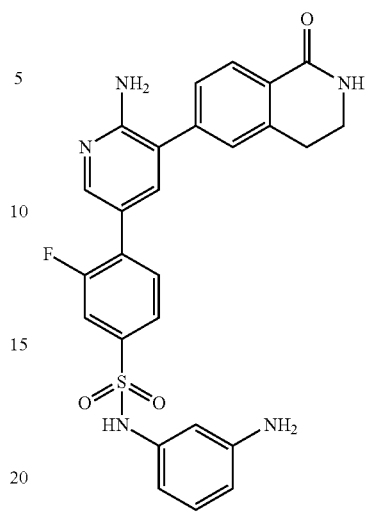

4-(6-amino-5-(1-oxo-1,2,3,4-tetrahydroisoquinolin-6-yl) pyridin-3-yl)-N-(3-aminophenyl)-3-fluorobenzenesulfonamide (15) (0.1 g, 0.2 mmol) was dissolved in 4 mL THF and Et$_3$N (56 uL, 0.4 mmol) was added. The reaction was stirred at −20° C. when chloroacetyl chloride (16 uL, 0.2 mmol) in 2 mL THF was added dropwisely. The mixture was stirred at −20° C. for 1 hour. Then the reaction was diluted with EtOAc, washed with brine (10 mL×2). Combined aqueous layer was extracted with EtOAc. Combined EtOAc was dried over MgSO$_4$, filtered, and concentrated under reduced pressure. Crude material was purified by flash column chromatography (5% to 30% MeOH in EtOAc) to afford 91 mg product (79%). LCMS (ESI) m/z 580.22 [(M+H)$^+$; calcd for C$_{28}$H$_{24}$ClFN$_5$O$_4$S$^+$: 580.12]

Example 2: 4-((2-((3-((4-(6-amino-5-(1-oxo-1,2,3,4-tetrahydroisoquinolin-6-yl)pyridin-3-yl)-3-fluorophenyl)sulfonamido)phenyl)amino)-2-oxoethyl)amino)-N-(2-(2,6-dioxopiperidin-3-yl)-1-oxoisoindolin-4-yl)butanamide (I-1)

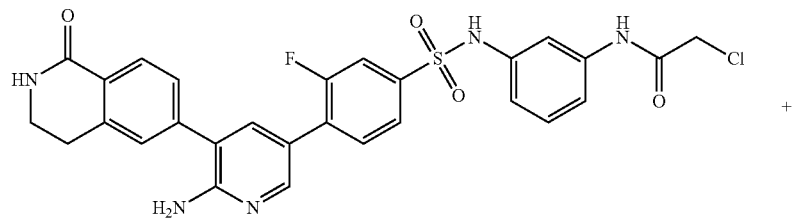

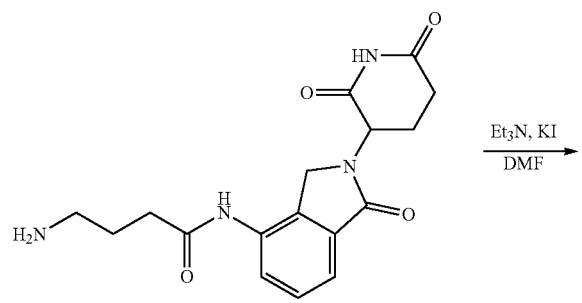

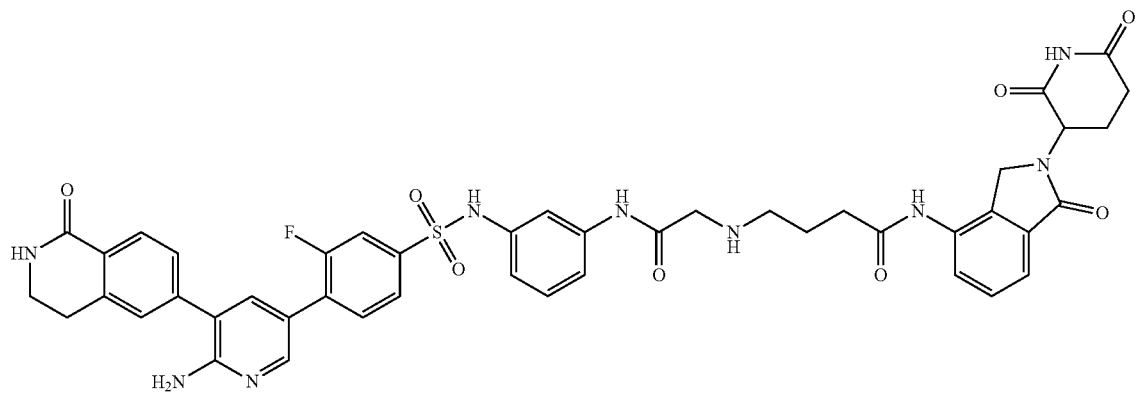

N-(3-((4-(6-amino-5-(1-oxo-1,2,3,4-tetrahydroisoquinolin-6-yl)pyridin-3-yl)-3-fluorophenyl)sulfonamido)phenyl)-2-chloroacetamide (0.045g, 0.078 mmol), 4-amino-N-(2-(2,6-dioxopiperidin-3-yl)-1-oxoisoindolin-4-yl)butanamide (0.03g, 0.078 mmol) and KI (1.3 mg, 0.008 mmol) were added into 3 mL DMF. Then Et₃N (22 uL, 0.16 mL) was added into the mixture, which was stirred at 50° C. overnight, then 90° C. for 1 hour. The mixture was then cooled to room temperature. The mixture was purified firstly by preparative HPLC, followed by flash chromatography (20% to 60% MeOH in EtOAc) to afford 11 mg product (16%). LCMS (ESI) m/z 888.30 [(M+H)$^+$; calcd for $C_{45}H_{43}FN_9O_8S^+$: 888.29]

Example 3: 4-((2-((4-((4-(6-amino-5-(1-oxo-1,2,3,4-tetrahydroisoquinolin-6-yl)pyridin-3-yl)-3-fluoro-phenyl)sulfonamido)phenyl)amino)-2-oxoethyl)amino)-N-(2-(2,6-dioxopiperidin-3-yl)-1-oxoisoindolin-4-yl)butanamide (I-4)

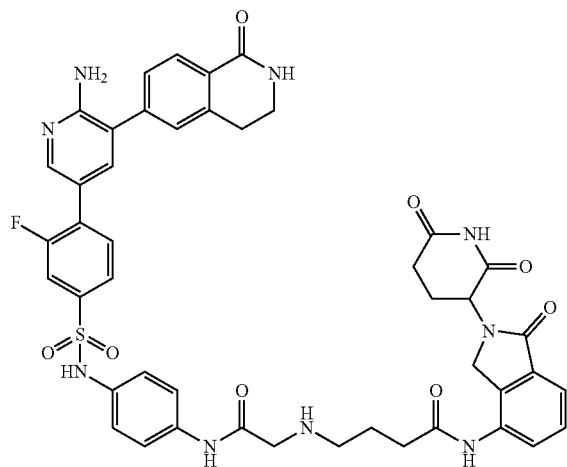 [SMILES: Nc1ncc(-c2ccc(S(=O)(=O)Nc3ccc(NC(=O)CNCCCC(=O)Nc4cccc5c4CN(C4CCC(=O)NC4=O)C5=O)cc3)cc2F)cc1-c1ccc2c(c1)CCNC2=O]

The title compound was synthesized according to the general procedures in Examples 1 and 2. 5 mg (7.3%); LCMS (ESI) m/z 888.30 [(M+H)+; calcd for $C_{45}H_{43}FN_9O_8S^+$: 888.29]

Example 4: 5-((2-((4-((4-(6-amino-5-(1-oxo-1,2,3,4-tetrahydroisoquinolin-6-yl)pyridin-3-yl)-3-fluoro-phenyl)sulfonamido)phenyl)amino)-2-oxoethyl)amino)-N-(2-(2,6-dioxopiperidin-3-yl)-1-oxoisoindolin-4-yl)pentanamide (I-5)

The title compound was synthesized according to the general procedures in Examples 1 and 2. 6 mg (8.6%); LCMS (ESI) m/z 902.20 [(M+H)+; calcd for $C_{46}H_{45}FN_9O_8S^+$: 902.31])

Example 5: 6-((2-((4-((4-(6-amino-5-(1-oxo-1,2,3,4-tetrahydroisoquinolin-6-yl)pyridin-3-yl)-3-fluoro-phenyl)sulfonamido)phenyl)amino)-2-oxoethyl)amino)-N-(2-(2,6-dioxopiperidin-3-yl)-1-oxoisoindolin-4-yl)hexanamide (I-6)

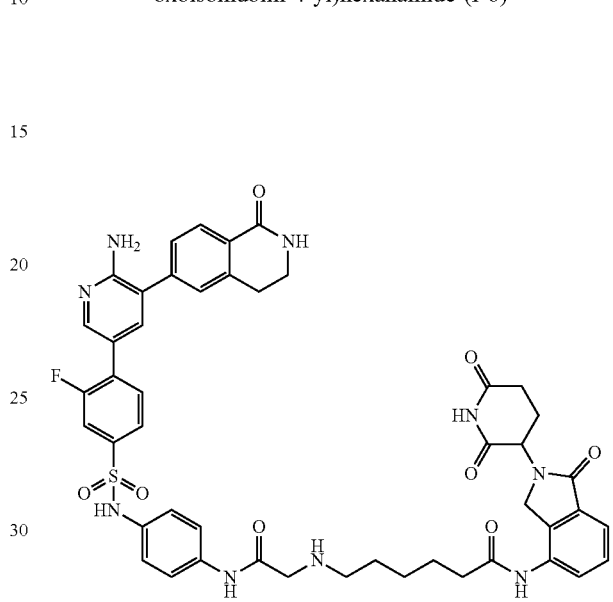

The title compound was synthesized according to the general procedures in Examples 1 and 2. 1 mg (1.5%); LCMS (ESI) m/z 916.40 [(M+H)+; calcd for $C_{47}H_{47}FN_9O_8S^+$: 916.32]

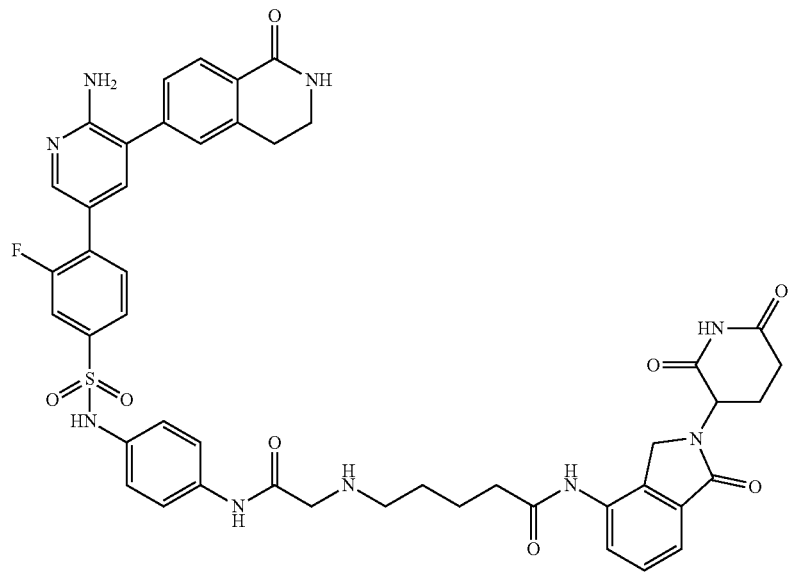 [SMILES: Nc1ncc(-c2ccc(S(=O)(=O)Nc3ccc(NC(=O)CNCCCCC(=O)Nc4cccc5c4CN(C4CCC(=O)NC4=O)C5=O)cc3)cc2F)cc1-c1ccc2c(c1)CCNC2=O]

Example 6: 5-((2-((3-((4-(6-amino-5-(1-oxo-1,2,3,4-tetrahydroisoquinolin-6-yl)pyridin-3-yl)-3-fluorophenyl)sulfonamido)phenyl)amino)-2-oxoethyl)amino)-N-(2-(2,6-dioxopiperidin-3-yl)-1-oxoisoindolin-4-yl)pentanamide (I-2)

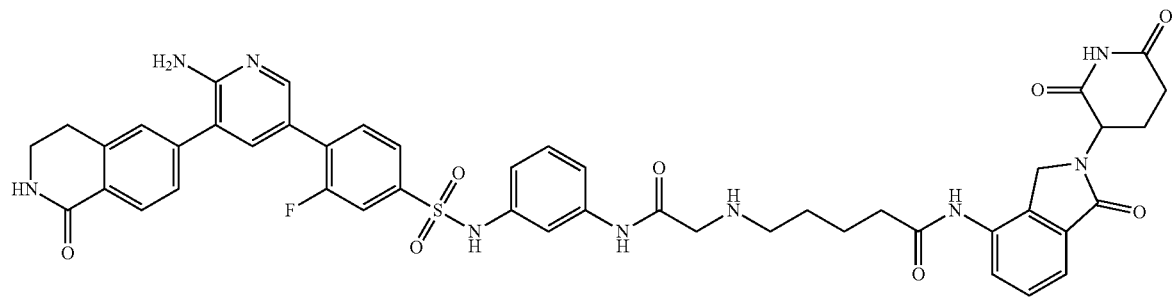 [SMILES: Nc1ncc(-c2ccc(S(=O)(=O)Nc3cccc(NC(=O)CNCCCCC(=O)Nc4cccc5c4CN(C4CCC(=O)NC4=O)C5=O)c3)cc2F)cc1-c1ccc2c(c1)CCNC2=O]

The title compound was synthesized according to the general procedures in Examples 1 and 2. 9 mg (13%); LCMS (ESI) m/z 902.30 [(M+H)$^+$; calcd for $C_{46}H_{45}FN_9O_8S^+$: 902.31]

Example 7: 6-((2-((3-((4-(6-amino-5-(1-oxo-1,2,3,4-tetrahydroisoquinolin-6-yl)pyridin-3-yl)-3-fluorophenyl)sulfonamido)phenyl)amino)-2-oxoethyl)amino)-N-(2-(2,6-dioxopiperidin-3-yl)-1-oxoisoindolin-4-yl)hexanamide (I-3)

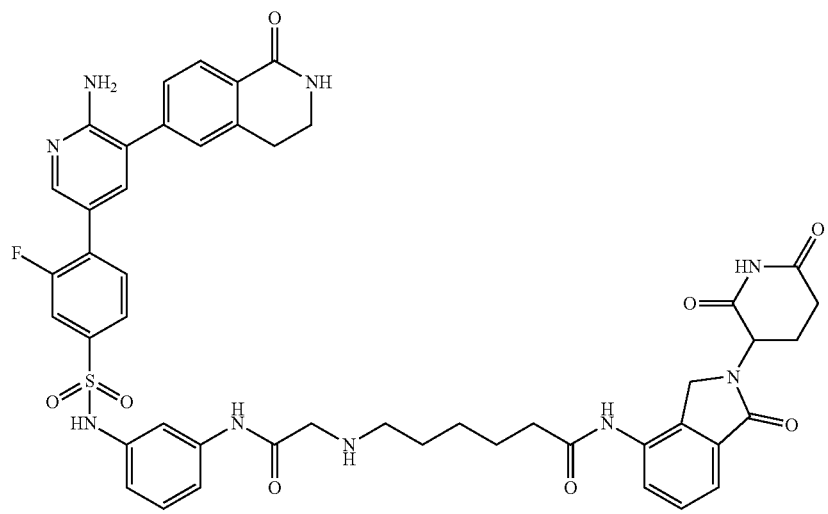 [SMILES: Nc1ncc(-c2ccc(S(=O)(=O)Nc3cccc(NC(=O)CNCCCCCC(=O)Nc4cccc5c4CN(C4CCC(=O)NC4=O)C5=O)c3)cc2F)cc1-c1ccc2c(c1)CCNC2=O]

The title compound was synthesized according to the general procedures in Examples 1 and 2. 3.7 mg (6%); LCMS (ESI) m/z 916.50 [(M+H)$^+$; calcd for $C_{47}H_{47}FN_9O_8S^+$: 916.32]

Example 8: Synthesis of Linker-Attached Cereblon Ligands

Step 1

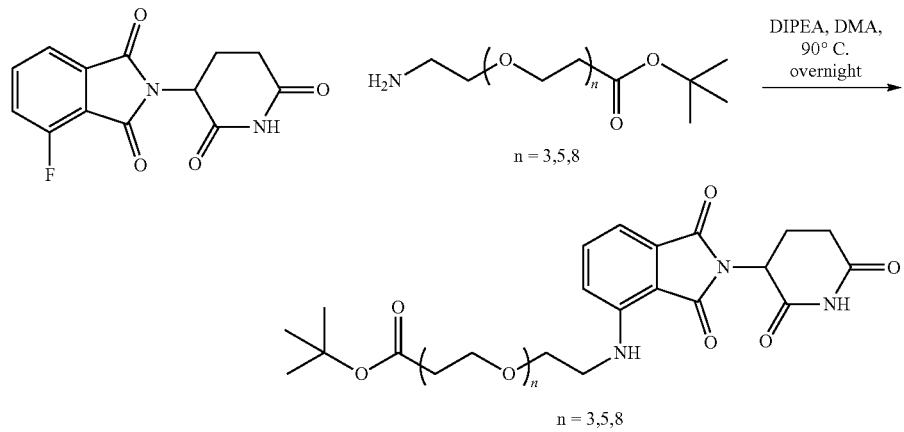

2-(2,6-dioxopiperidin-3-yl)-4-fluoroisoindoline-1,3-dione (0.28g, 1 mmol), amino-PEG-tert-butyl ester [0.28g (PEG3); 0.36g (PEG5); 0.49g (PEG8), 1 mmol], and N,N-diisopropylethylamine (DIPEA) (0.24 mL, 1.5 mmol) were mixed in 3 mL dimethylacetamide (DMA). The reaction mixture was heated at 90° C. in sealed reaction tube overnight. Then the reaction was cooled to room temperature. The crude was directly subjected to HPLC purification (MeCN/H$_2$O w/0.5‰ TFA). Isolated products was then purified again using normal phase CombiFlash Rf+ system (80%-10% EtOAc in hexanes). Final products were collected as condensed yellow oil (62% for PEG3; 44% for PEG5; 45% for PEG8).

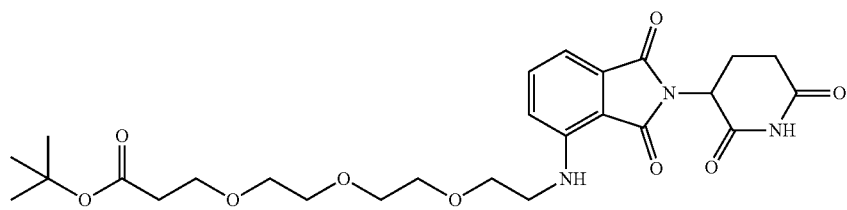 [SMILES: CC(C)(C)OC(=O)CCOCCOCCOCCNc1cccc2c1C(=O)N(C1CCC(=O)NC1=O)C2=O]

LCMS (ESI) m/z 534.31 [(M+H)$^+$; calcd for $C_{26}H_{36}N_3O_9^+$: 534.24]

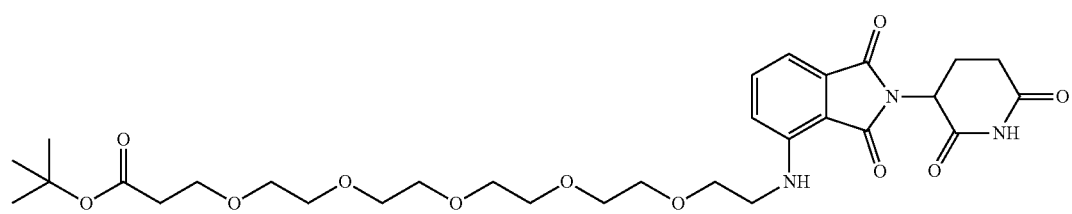 [SMILES: CC(C)(C)OC(=O)CCOCCOCCOCCOCCOCCNc1cccc2c1C(=O)N(C1CCC(=O)NC1=O)C2=O]

LCMS (ESI) m/z 622.23 [(M+H)$^+$; calcd for $C_{30}H_{44}N_3O_{14}^+$: 622.30]

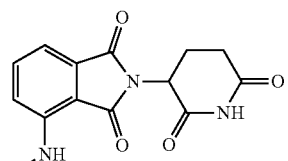

LCMS (ESI) m/z 754.46 [(M+H)⁺; calcd for $C_{36}H_{56}N_3O_{14}^+$: 754.38]

Step 2.

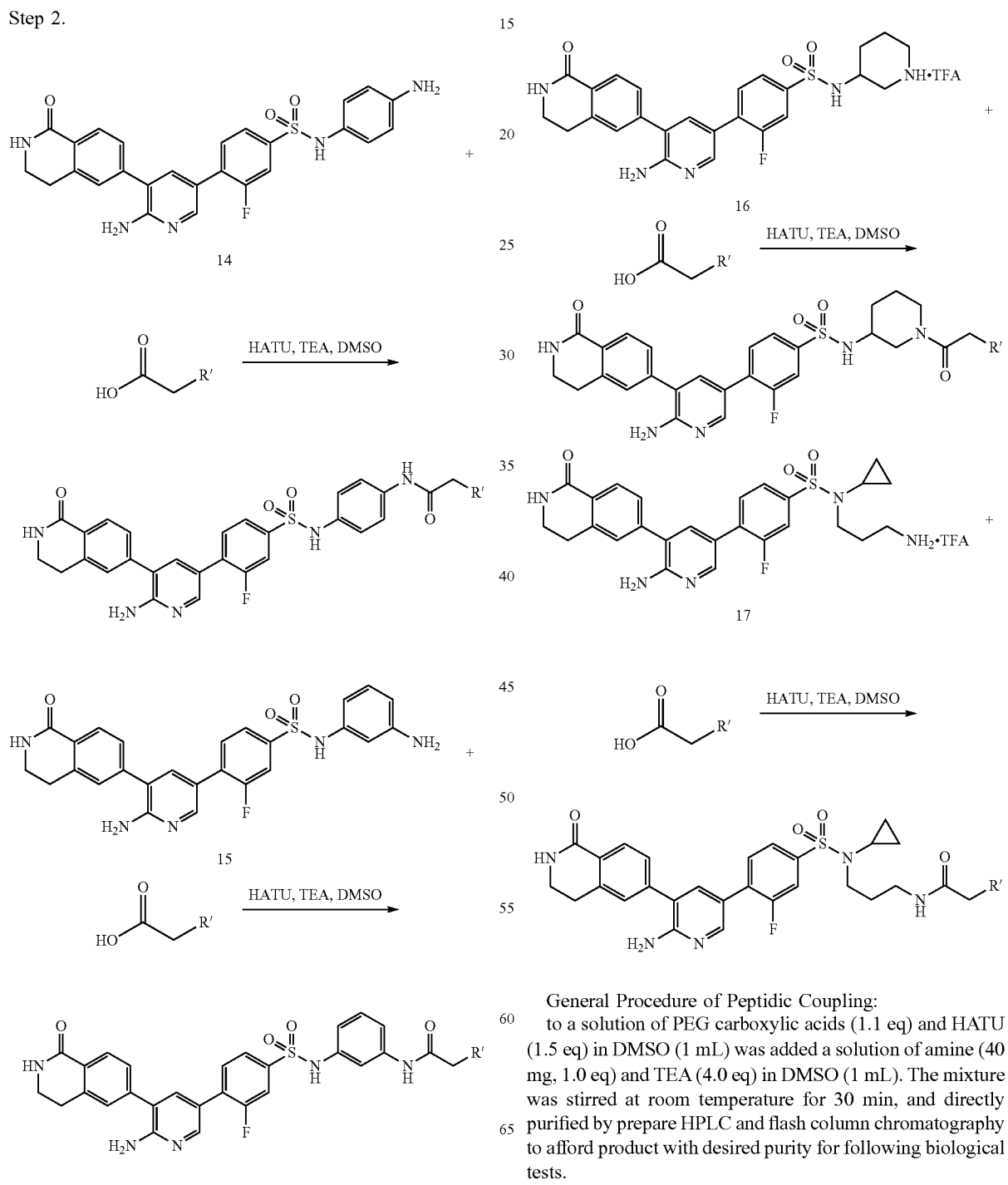

General Procedure of Peptidic Coupling:
to a solution of PEG carboxylic acids (1.1 eq) and HATU (1.5 eq) in DMSO (1 mL) was added a solution of amine (40 mg, 1.0 eq) and TEA (4.0 eq) in DMSO (1 mL). The mixture was stirred at room temperature for 30 min, and directly purified by prepare HPLC and flash column chromatography to afford product with desired purity for following biological tests.

Example 9: N-(4-((4-(6-amino-5-(1-oxo-1,2,3,4-tetrahydroisoquinolin-6-yl)pyridin-3-yl)-3-fluorophenyl)sulfonamido)phenyl)-1-((2-(2,6-dioxopiperidin-3-yl)-1,3-dioxoisoindolin-4-yl)amino)-3,6,9,12,15-pentaoxaoctadecan-18-amide (I-7)

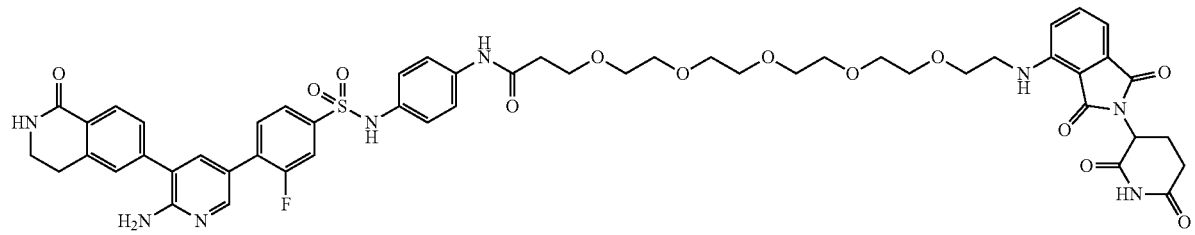

I-7

The title compound was synthesized according to Example 8. LCMS (ESI) m/z 1051.45 [(M+H)$^+$; calcd for $C_{52}H_{55}FN_8O_{13}S^+$: 1051.11].

Example 10: N-(4-((4-(6-amino-5-(1-oxo-1,2,3,4-tetrahydroisoquinolin-6-yl)pyridin-3-yl)-3-fluorophenyl)sulfonamido)phenyl)-3-(2-(2-(2-((2-(2,6-dioxopiperidin-3-yl)-1,3-dioxoisoindolin-4-yl)amino)ethoxy)ethoxy)ethoxy)propanamide (I-8)

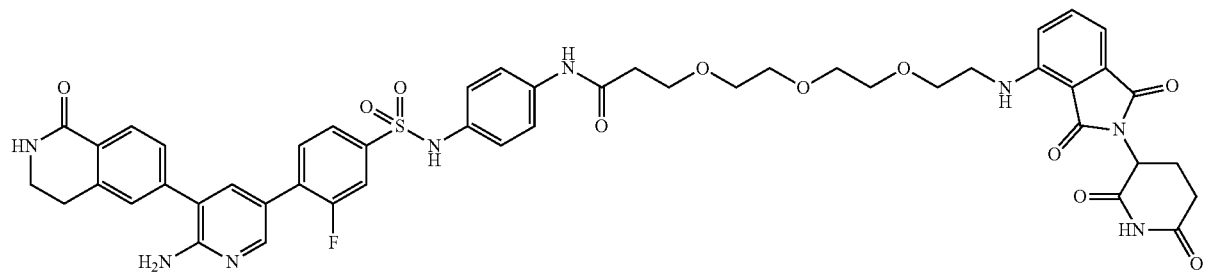

I-8

The title compound was synthesized according to Example 8. LCMS (ESI) m/z 963.32 [(M+H)$^+$; calcd for $C_{45}H_{47}FN_8O_{11}S^+$: 963.01].

Example 11: N-(3-((4-(6-amino-5-(1-oxo-1,2,3,4-tetrahydroisoquinolin-6-yl)pyridin-3-yl)-3-fluorophenyl)sulfonamido)phenyl)-3-(2-(2-(2-((2-(2,6-dioxopiperidin-3-yl)-1,3-dioxoisoindolin-4-yl)amino)ethoxy)ethoxy)ethoxy)propanamide (I-9)

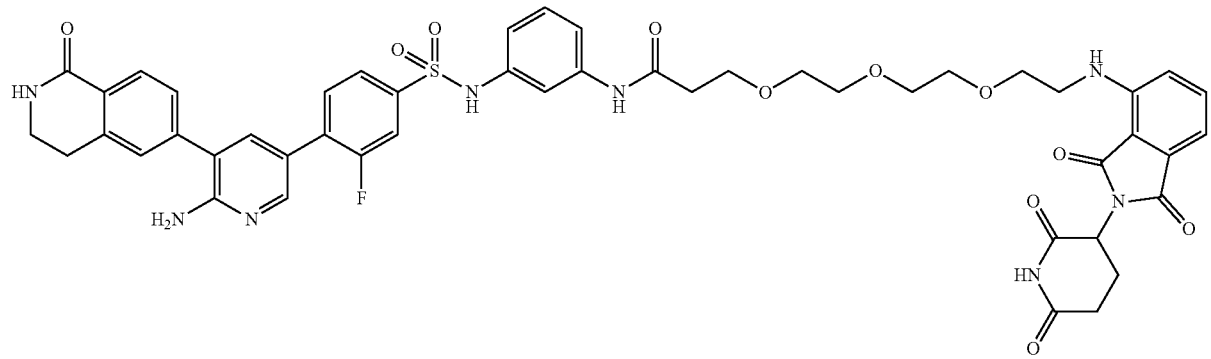

I-9

The title compound was synthesized according to Example 8. LCMS (ESI) m/z 963.42 [(M+H)+; calcd for $C_{48}H_{47}FN_8O_{11}S^+$: 963.01.]

Example 12: N-(3-((4-(6-amino-5-(1-oxo-1,2,3,4-tetrahydroisoquinolin-1-yl)pyridin-3-yl)-3-fluorophenyl)sulfonamido)phenyl)-1-((2-(2,6-dioxopiperidin-3-yl)-1,3-dioxoisoindolin-4-yl)amino)-3,6,9,12,15-pentaoxaoctadecan-18-amide (I-10)

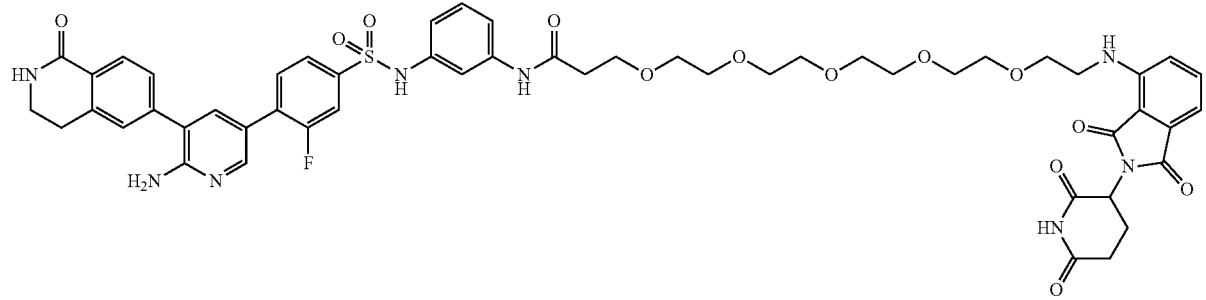

I-10

The title compound was synthesized according to Example 8. $^1$H NMR (500 MHz, DMSO) δ 11.11 (s, 1H), 9.90 (s, 1H), 8.23 (t, J=1.8 Hz, 1H), 8.00-7.88 (m, 2H), 7.74 (t, J=7.9 Hz, 1H), 7.65-7.54 (m, 4H), 7.51-7.40 (m, 3H), 7.24 (d, J=8.0 Hz, 1H), 7.17-7.06 (m, 2H), 7.03 (d, J=7.0 Hz, 1H), 6.76 (d, J=7.9 Hz, 1H), 6.60 (t, J=5.7 Hz, 1H), 6.13 (s, 2H), 5.06 (dd, J=12.7, 5.4 Hz, 1H), 3.72-3.56 (m, 5H), 3.57-3.34 (m, 22H), 3.00-2.81 (m, 3H), 2.65-2.52 (m, 2H), 2.08-1.97 (m, 1H). $^{13}$C NMR (126 MHz, DMSO) δ 173.29, 170.55, 169.64, 169.40, 167.76, 164.76, 159.75, 157.76, 156.94, 148.03, 146.87, 141.28, 140.41, 140.29, 138.07, 136.68, 132.55, 130.89, 129.56, 128.93, 128.13, 127.28, 123.58, 119.73, 118.98, 117.90, 115.36, 115.02, 114.82, 111.14, 109.70, 70.27, 70.21, 70.10, 69.33, 67.10, 49.03, 42.16, 37.60, 31.45, 28.27, 22.62. LCMS (ESI) m/z 1051.35 [(M+H); calcd for $C_{52}H_{55}FN_8O_{13}S^+$: 1051.11.]

Example 13: N-(4-((4-(6-amino-5-(1-oxo-1,2,3,4-tetrahydroisoquinolin-6-yl)pyridin-3-yl)-3-fluorophenyl)sulfonamido)phenyl)-1-((2-(2,6-dioxopiperidin-3-yl)-1,3-dioxoisoindolin-4-yl)amino)-3,6,9,12,15,18,21,24-octaoxaheptacosan-27-amide (I-11)

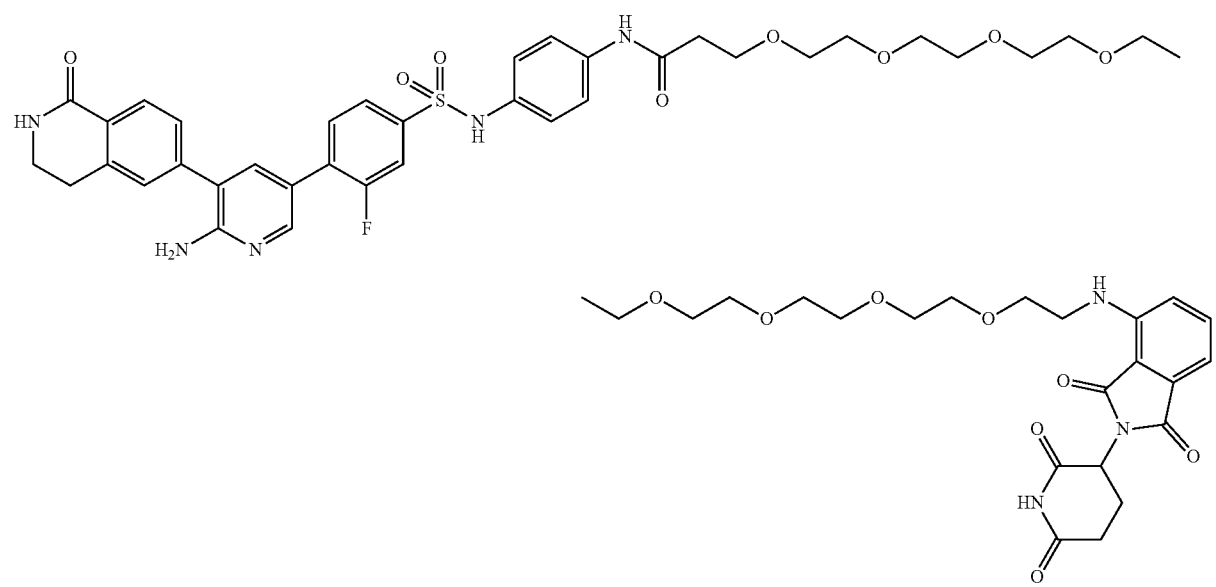

The title compound was synthesized according to Example 8. LCMS (ESI) m/z 1183.53 [(M+H)⁺; calcd for $C_{58}H_{67}FN_8O_{16}S^+$: 1183.27].

Example 14: N-(3-((4-(6-amino-5-(1-oxo-1,2,3,4-tetrahydroisoquinolin-6-yl)pyridin-3-yl)-3-fluorophenyl)sulfonamido)phenyl)-1-((2-(2,6-dioxopiperidin-3-yl)-1,3-dioxoisoindolin-4-yl)amino)-3,6,9,12,15,18,21,24-octaoxaheptacosan-27-amide (I-12)

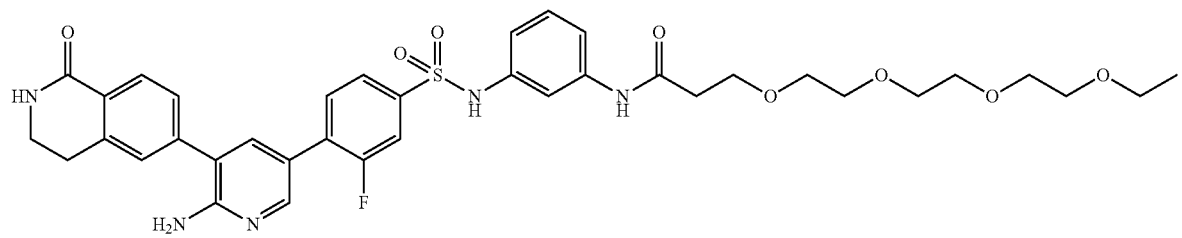

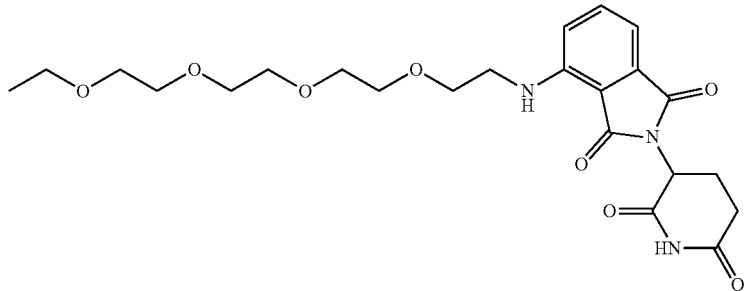

The title compound was synthesized according to Example 8. LCMS (ESI) m/z 1183.53 [(M+H)⁺; calcd for $C_{58}H_{67}FN_8O_{16}S^+$: 1183.27].

Example 15: 4-(6-amino-5-(1-oxo-1,2,3,4-tetrahydroisoquinolin-1-yl)pyridin-3-yl)-N-(1-(1-((2-(2,6-dioxopiperidin-3-yl)-1,3-dioxoisoindolin-4-yl)amino)-3,6,9,12,15-pentaoxaoctadecan-18-oyl)piperidin-3-yl)-3-fluorobenzenesulfonamide (I-20)

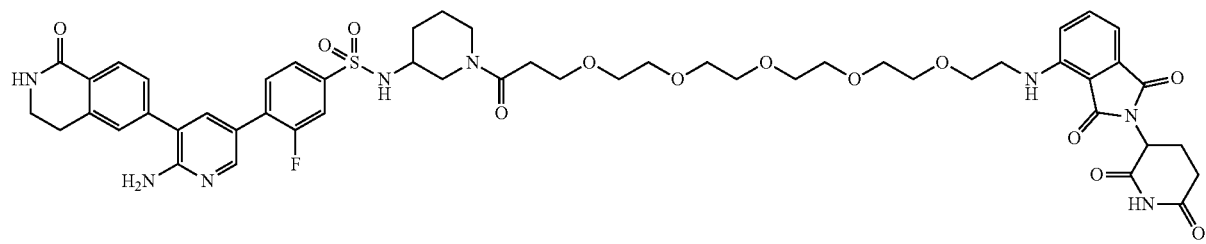 [SMILES: Nc1ncc(-c2ccc(S(=O)(=O)NC3CCCN(C(=O)CCOCCOCCOCCOCCOCCNc4cccc5c4C(=O)N(C4CCC(=O)NC4=O)C5=O)C3)cc2F)cc1-c1ccc2c(c1)CCNC2=O]

The title compound was synthesized according to Example 8. LCMS (EST) m/z 1043.64 [(M+H)⁺; calcd for $C_{51}H_{59}FN_8O_{13}S^+$: 1043.13].

Example 16: N-(3-((4-(6-amino-5-(1-oxo-1,2,3,4-tetrahydroisoquinolin-6-yl)pyridin-3-yl)-N-cyclopropyl-3-fluorophenyl)sulfonamido)propyl)-1-((2-(2,6-dioxopiperidin-3-yl)-1,3-dioxoisoindolin-4-yl)amino)-3,6,9,12,15-pentaoxaoctadecan-18-amide (I-19)

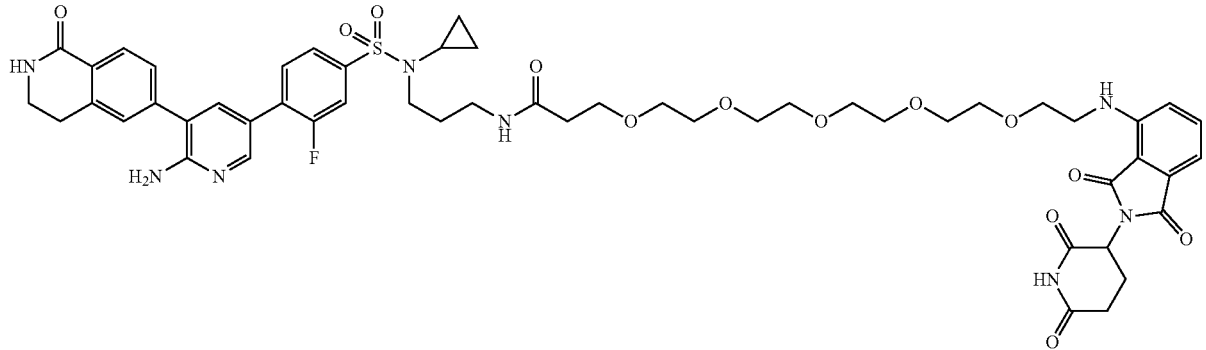

The title compound was synthesized according to Example 8. $^1$H NMR (500 MHz, CDCl$_3$) δ 10.58 (s, 1H), 8.36 (s, 1H), 8.18 (d, J=7.9 Hz, 1H), 7.75-7.55 (m, 2H), 7.49 (t, J=7.7 Hz, 1H), 7.37 (s, 1H), 7.10 (d, J=7.1 Hz, 1H), 7.00 (t, J=5.7 Hz, 1H), 6.93 (d, J=8.6 Hz, 1H), 6.51 (dd, J=12.3, 6.7 Hz, 1H), 5.34 (s, 1H), 4.94 (dd, J=12.1, 5.3 Hz, 1H), 3.72 (dt, J=17.4, 8.9 Hz, 3H), 3.69-3.57 (m, 9H), 3.54-3.42 (m, 2H), 3.35-3.22 (m, 2H), 3.07 (t, J=6.5 Hz, 1H), 2.94-2.68 (m, 2H), 2.49 (t, J=5.7 Hz, 1H), 2.22-2.01 (m, 1H), 1.91-1.77 (m, 1H), 0.88 (t, J=7.7 Hz, 1H), 0.73 (q, J=6.1 Hz, 1H). $^{13}$C NMR (126 MHz, CDCl$_3$) δ 172.46, 171.84, 169.36, 169.27, 167.72, 165.73, 160.16, 158.15, 155.81, 146.83, 141.05, 140.02, 138.41, 136.05, 132.52, 130.35, 129.07, 128.72, 127.59, 127.33, 123.74, 120.45, 116.83, 115.85, 115.64, 111.61, 110.29, 70.64, 70.48, 70.43, 70.36, 70.25, 70.10, 69.41, 67.35, 48.95, 48.80, 42.36, 42.26, 40.15, 40.01, 36.89, 36.40, 36.27, 31.56, 30.72, 28.46, 28.37, 22.81, 7.11. LCMS (ESI) m/z 1057.54 [(M+H)$^+$; calcd for C$_{52}$H$_{61}$FN$_8$O$_{13}$S$^+$: 1057.16].

Example 17: N-(3-((4-(6-amino-5-(1-oxo-1,2,3,4-tetrahydroisoquinolin-6-yl)pyridin-3-yl)-N-cyclopropyl-3-fluorophenyl)sulfonamido)propyl)-3-(2-(2-((2-(2,6-dioxopiperidin-3-yl)-1,3-dioxoisoindolin-4-yl)amino)ethoxy)ethoxy)ethoxy)propanamide (I-22)

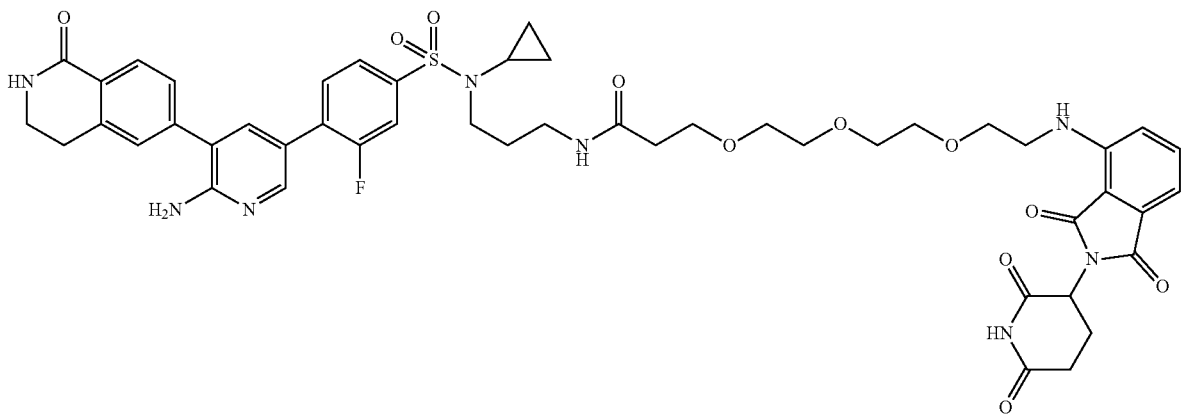 [SMILES: Nc1ncc(-c2ccc(S(=O)(=O)N(CCCNC(=O)CCOCCOCCOCCNc3cccc4c3C(=O)N(C3CCC(=O)NC3=O)C4=O)C3CC3)cc2F)cc1-c1ccc2c(c1)CCNC2=O]

The title compound was synthesized according to Example 8. LCMS (ESI) m/z 969.53 [(M+H)$^+$; calcd for C$_{48}$H$_{53}$FN$_8$O$_{11}$S$^+$: 969.06].

Example 18: N-(3-((4-(6-amino-5-(1-oxo-1,2,3,4-tetrahydroisoquinolin-6-yl)pyridin-3-yl)-3-fluorophenyl)sulfonamido)phenyl)-1-(2-((2-(2,6-dioxopiperidin-3-yl)-1,3-dioxoisoindolin-4-yl)amino)acetamido)-3,6,9,12-tetraoxapentadecan-15-amide (I-14)

Step 1

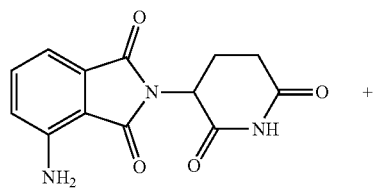

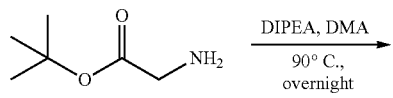

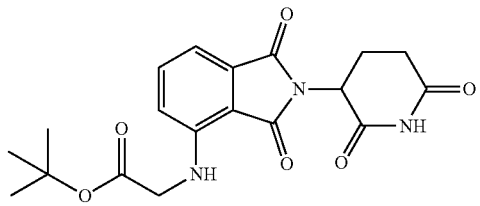

2-(2,6-dioxopiperidin-3-yl)-4-fluoroisoindoline-1,3-dione (0.19g, 0.7 mmol), glycine tert-butyl ester hydrochloride (0.12g, 0.7 mmol), and DIPEA (0.23 mL, 1.4 mmol) were added into 0.75 mL DMA. The mixture was heated at 90° C. overnight in a sealed tube, and then cooled to room temperature. The crude was directly subjected to HPLC purification (MeCN/H$_2$O w/0.5‰ TFA). Isolated products was then purified again using normal phase CombiFlash Rf+ system (80%-100% EtOAc in hexanes). Final products were collected as condensed yellow solid (15%). LCMS (ESI) m/z 331.98 (show as free acid instead of t-butyl ester) [(M+H)$^+$; calcd for C$_{19}$H$_{22}$N$_3$O$_6$$^+$: 388.15]

Step 2

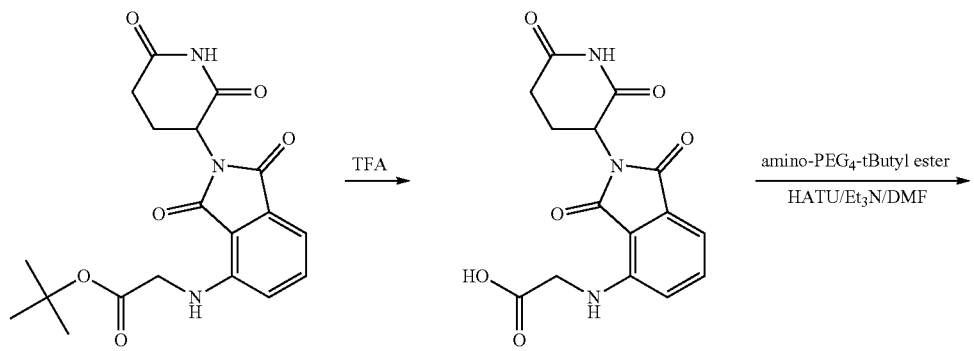

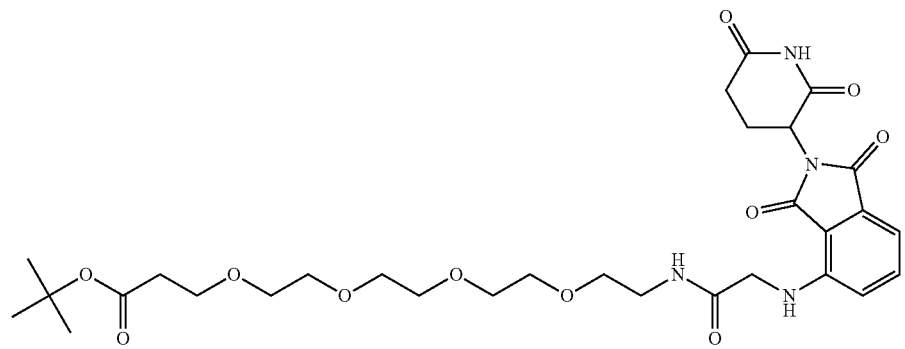

tert-butyl (2-(2,6-dioxopiperidin-3-yl)-1,3-dioxoisoindolin-4-yl)glycinate (0.1g 0.25 mmol) was dissolved in 1 mL TFA. The mixture was stirred at room temperature for 2 hours, then concentrated under reduced pressure to afford solid product which was used in the following reaction without further purification. (2-(26-dioxopiperidin-3-yl)-1,3-dioxoisoindolin-4-yl)glycine product (0.05g, 0.15 mmol) was mixed with HATU (0.114g, 0.3 mmol) in 3 mL DMF. Et$_3$N (0.105 mL, 0.75 mmol) was added. The mixture was stirred for 10 mins before the amino-PEG4-t-Butyl ester (0.05g, 0.15 mmol) was added. The reaction was then stirred at room temperature overnight. The solution was next subjected to preparative HPLC purification to afford 48 mg product (51%). LCMS (ESI) m/z 579.32 (show as free acid instead of t-butyl ester)[(M+H); calcd for $C_{30}H_{43}N_4O_{11}^+$: 635.29]

Step 3

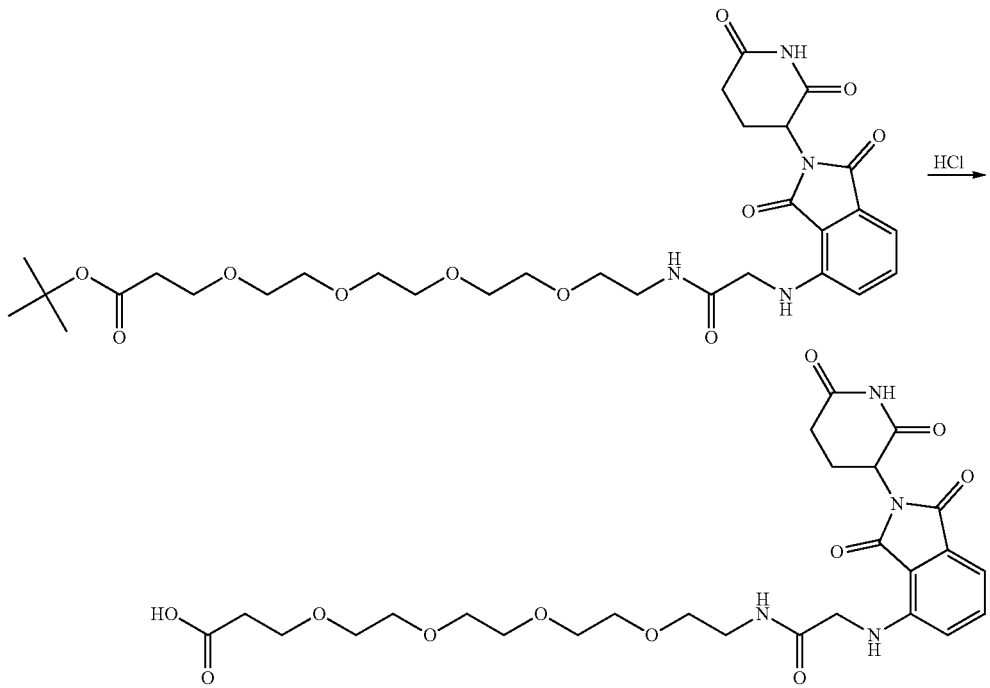

tert-butyl 1-((2-(2-(2,6-dioxopiperidin-3-yl)-1,3-dioxoisoindolin-4-yl)amino)-2-oxo-6,9,12,15-tetraoxa-3-azaoctadecan-18-oate (48 mg, 0.076 mmol) was treated with 4M HCl in dioxane/H$_2$O at room temperature. The solution was stirred at room temperature for 2 hours, then concentrated under reduced pressure. The crude product was used in following reactions without further purification.

Step 4

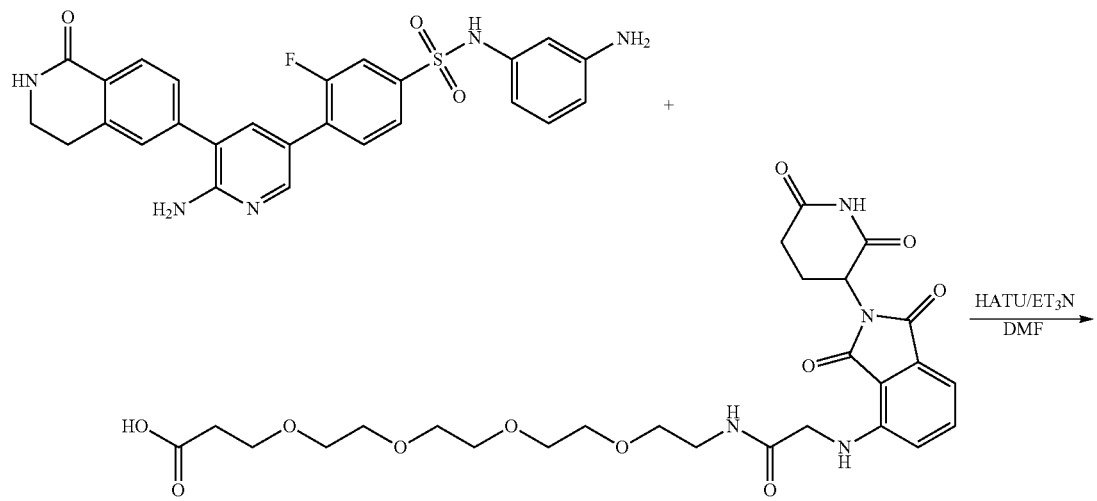

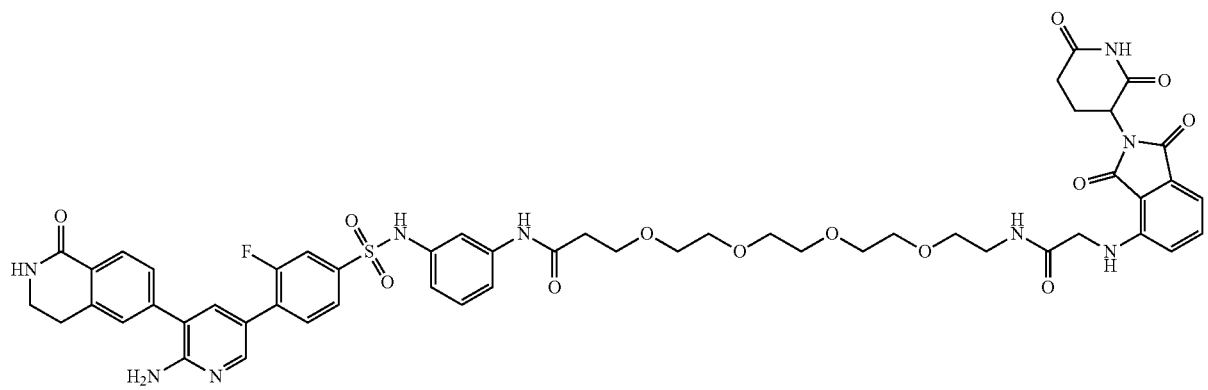

1-((2-(2,6-dioxopiperidin-3-yl)-1,3-dioxoisoindolin-4-yl)amino)-2-oxo-6,9,12,15-tetraoxa-3-azaoctadecan-18-oic acid (0.043g, 0.076 mmol) and HATU (0.058g, 0.152 mmol) were mixed in 2 mL DMF. Et₃N (54 uL, 0.38 mmol) was added in the solution. The mixture was stirred for 10 min before 4-(6-amino-5-(1-oxo-1,2,3,4-tetrahydroisoquinolin-6-yl)pyridin-3-yl)-N-(3-aminophenyl)-3-fluorobenzenesulfonamide (15) (0.038g, 0.076 mmol) was added into the reaction. The reaction was then stirred at room temperature overnight, and directly subjected to preparative HPLC purification, followed by flash chromatography (5%-50% MeOH in EtOAc) to afford 34 mg I-14 (43%). LCMS (ESI) m/z 1064.26 [(M+H)⁺; calcd for $C_{52}H_{55}FN_9O_{13}S^+$: 1064.36]

Example 19: N-(4-((4-(6-amino-5-(1-oxo-1,2,3,4-tetrahydroisoquinolin-6-yl)pyridin-3-yl)-3-fluorophenyl)sulfonamido)phenyl)-1-((2-(2,6-dioxopiperidin-3-yl)-1,3-dioxoisoindolin-4-yl)amino)-3,6,9,12,15,18,21,24-octaoxaheptacosan-27-amide (I-18)

Step 1

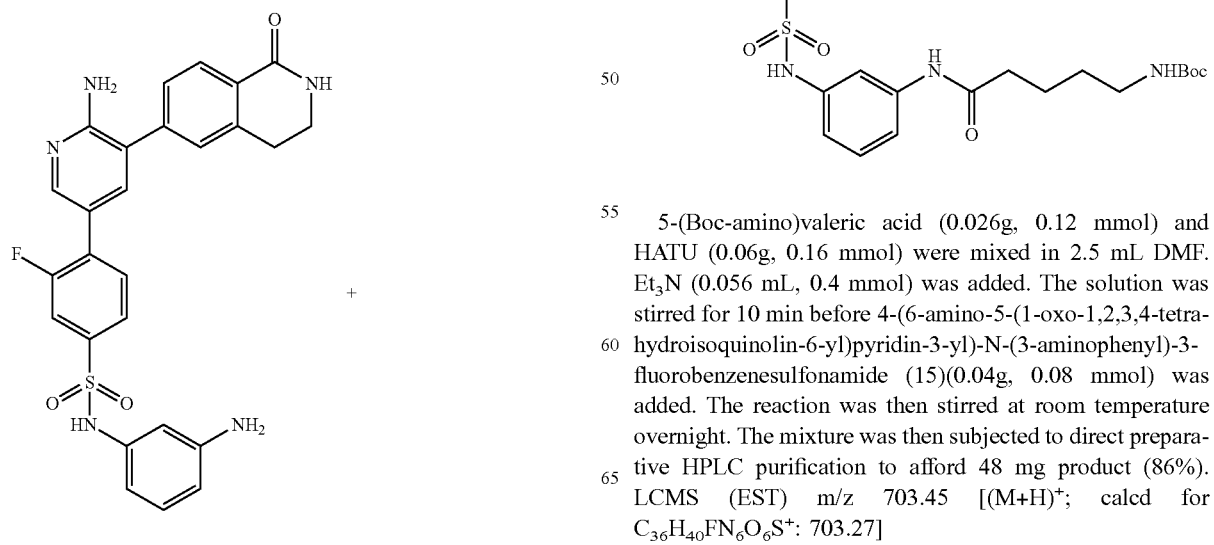

5-(Boc-amino)valeric acid (0.026g, 0.12 mmol) and HATU (0.06g, 0.16 mmol) were mixed in 2.5 mL DMF. Et₃N (0.056 mL, 0.4 mmol) was added. The solution was stirred for 10 min before 4-(6-amino-5-(1-oxo-1,2,3,4-tetrahydroisoquinolin-6-yl)pyridin-3-yl)-N-(3-aminophenyl)-3-fluorobenzenesulfonamide (15)(0.04g, 0.08 mmol) was added. The reaction was then stirred at room temperature overnight. The mixture was then subjected to direct preparative HPLC purification to afford 48 mg product (86%). LCMS (ESI) m/z 703.45 [(M+H)⁺; calcd for $C_{36}H_{40}FN_6O_6S^+$: 703.27]

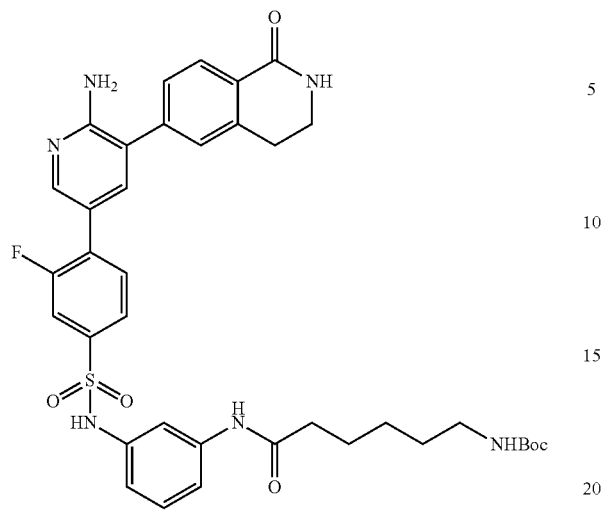
19 mg (33%); LCMS (ESI) m/z 717.45 [(M+H)+; calcd for $C_{37}H_{42}FN_6O_6S^+$: 717.29]
Step 2
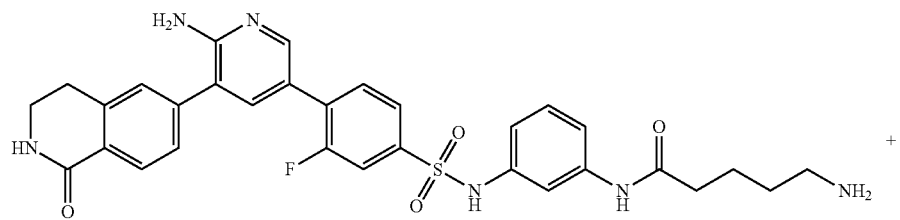
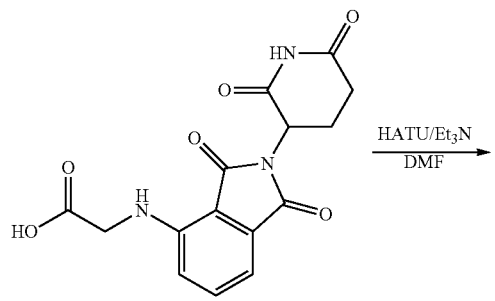
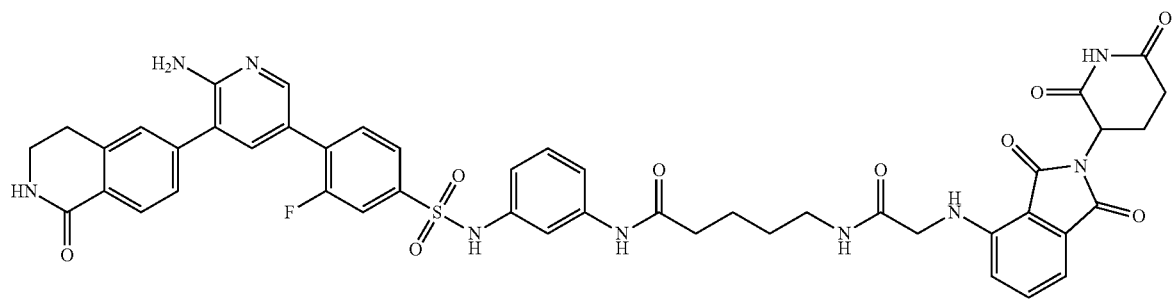

(2-(2,6-dioxopiperidin-3-yl)-1,3-dioxoisoindolin-4-yl) glycine (0.01g, 0.032 mmol) and HATU (0.02g, 0.052 mmol) were mixed in 1 mL DMF. Et₃N (36 uL, 0.26 mmol) was added in the solution. The mixture was stirred for 10 min before 5-amino-N-(3-((4-(6-amino-5-(1-oxo-1,2,3,4-tetrahydroisoquinolin-6-yl)pyridin-3-yl)-3-fluorophenyl)sulfonamido)phenyl)pentanamide (0.013g, 0.022 mmol) was added into the reaction. The reaction was then stirred at room temperature for 3 hours. The mixture was directly subjected to preparative HPLC purification, followed by flash chromatography (10%-20% MeOH in EtOAc) to afford 10 mg I-18 (50%). LCMS (ESI) m/z 916.30 [(M+H)⁺; calcd for C₄₆H₄₃FN₉O₉S⁺: 916.29])

Example 20: N-(3-((4-(6-amino-5-(1-oxo-1,2,3,4-tetrahydroisoquinolin-6-yl)pyridin-3-yl)-3-fluorophenyl)sulfonamido)phenyl)-6-(2-((2-(2,6-dioxopiperidin-3-yl)-1,3-dioxoisoindolin-4-yl)amino)acetamido)hexanamide (I-15)

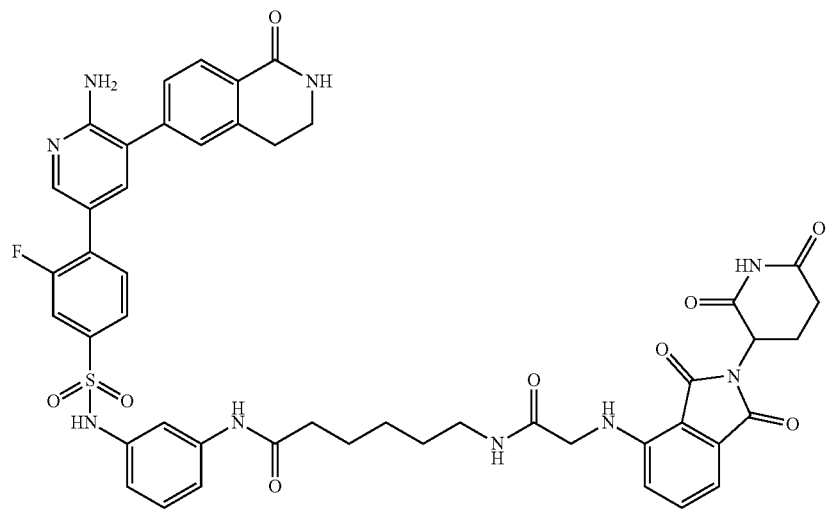 [SMILES: Nc1ncc(-c2ccc(S(=O)(=O)Nc3cccc(NC(=O)CCCCCNC(=O)CNc4cccc5c4C(=O)N(C4CCC(=O)NC4=O)C5=O)c3)cc2F)cc1-c1ccc2c(c1)CCNC2=O]

The title compound was synthesized according to Example 19. 10 mg (42%); LCMS (ESI) m/z 930.21 [(M+H)⁺; calcd for C₄₇H₄₅FN₉O₉S⁺: 930.30]

Example 21: N-(3-((4-(6-amino-5-(1-oxo-1,2,3,4-tetrahydroisoquinolin-1-yl)pyridin-3-yl)-3-fluorophenyl)sulfonamido)phenyl)-1-((2-(2,6-dioxopiperidin-3-yl)-1,3-dioxoisoindolin-4-yl)oxy)-3,6,9,12,15-pentaoxaoctadecan-18-amide (I-17)

Step 1

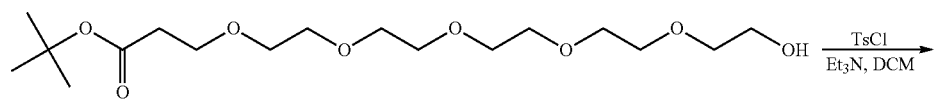

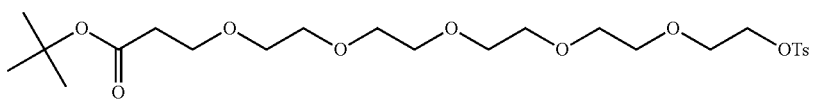

Hydroxy-PEG5-tert-butyl ester (0.18g, 0.5 mmol) was dissolved in 3 mL DCM. Et₃N (0.14 mL, 1.0 mmol) was added into the solution. Then the solution was placed on ice-bath while tosyl chloride (0.13g, 0.7 mmol) was added portionwisely. Upon completion of addition, the reaction was stirred at room temperature overnight. The mixture was then diluted with more DCM, washed with saturated NaHCO₃ (20 mL×2). Combined aqueous layer was extracted with DCM. Combined organic layer was dried over MgSO₄, filtered, and concentrated under reduced pressure. The crude material was purified by flash chromatography (50% to 100% hexanes in EtOAc) to afford 0.15g product (58%).
Step 2

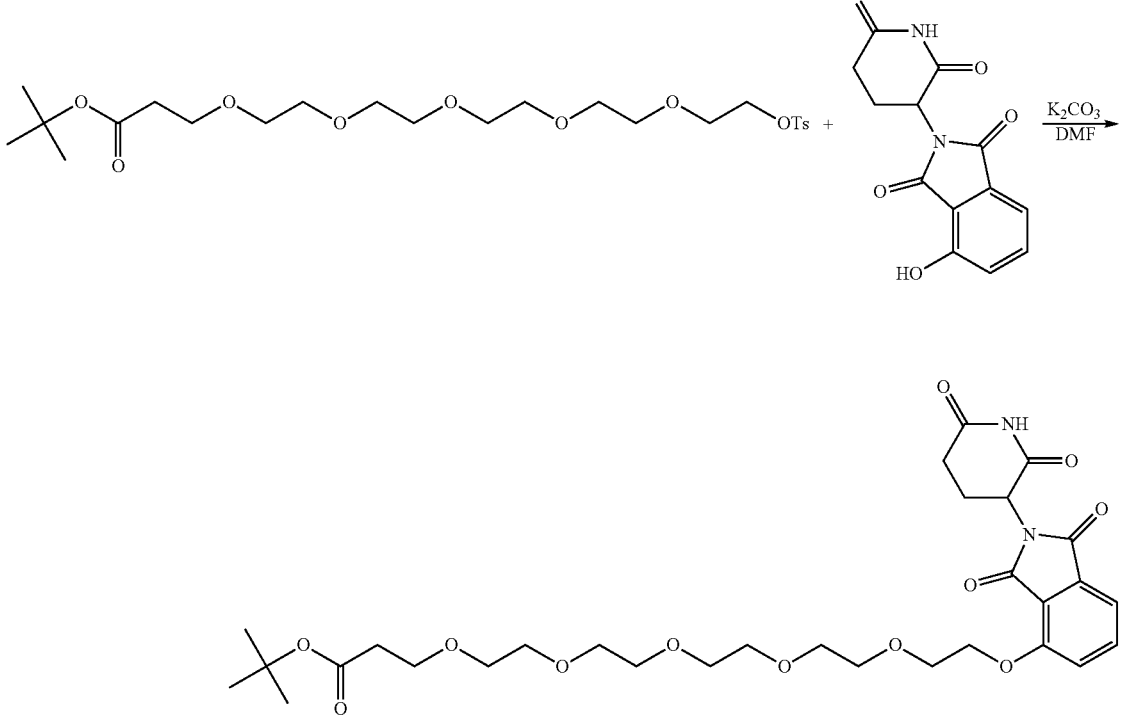

Step 2 tert-butyl 1-(tosyloxy)-3,6,9,12,15-pentaoxaoctadecan-18-oate (0.072g, 0.14 mmol) and 2-(2,6-dioxopiperidin-3-yl)-4-hydroxyisoindoline-1,3-dione (0.038g, 0.14 mmol) in 3 mL DMF. K₂CO₃ (0.029g, 0.21 mmol) was added into the reaction. The mixture was firstly stirred at room temperature, then at 55° C. overnight. The mixture was cooled, then subjected to preparative HPLC to afford 93 mg product (>100%). LCMS (ESI) m/z 567.22 (show as free acid instead of t-butyl ester) [(M+H)⁺; calcd for $C_{30}H_{43}N_2O_{12}^+$: 623.28]
Step 3

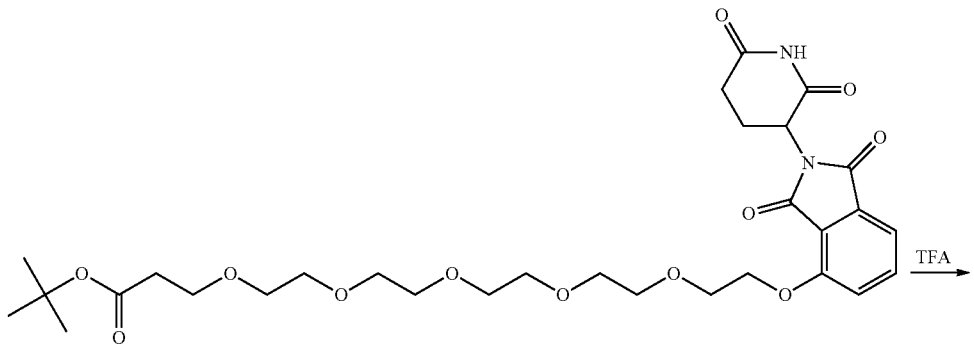

-continued

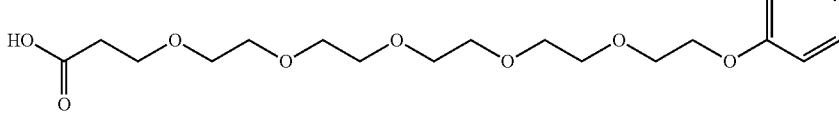

tert-butyl 1-((2-(2,6-dioxopiperidin-3-yl)-1,3-dioxoisoindolin-4-yl)oxy)-3,6,9,12,15-pentaoxaoctadecan-18-oate (0.093g, 0.15 mmol) was dissolved in 2 mL TFA. The solution was stirred at room temperature for 2 hours. Then the mixture was concentrated under reduced pressure to afford solid product, which was used in the following synthesis without further purification.

Step 4

2 mL DMF. Et$_3$N (100 uL, 0.6 mmol) was added in the solution. The mixture was stirred for 10 min before 4-(6-amino-5-(1-oxo-1,2,3,4-tetrahydroisoquinolin-6-yl)pyridin-3-yl)-N-(3-aminophenyl)-3-fluorobenzenesulfonamide (15) (0.06g, 0.12 mmol) was added into the reaction. The reaction was then stirred at room temperature for 5 hours. The mixture was directly subjected to preparative HPLC purifi-

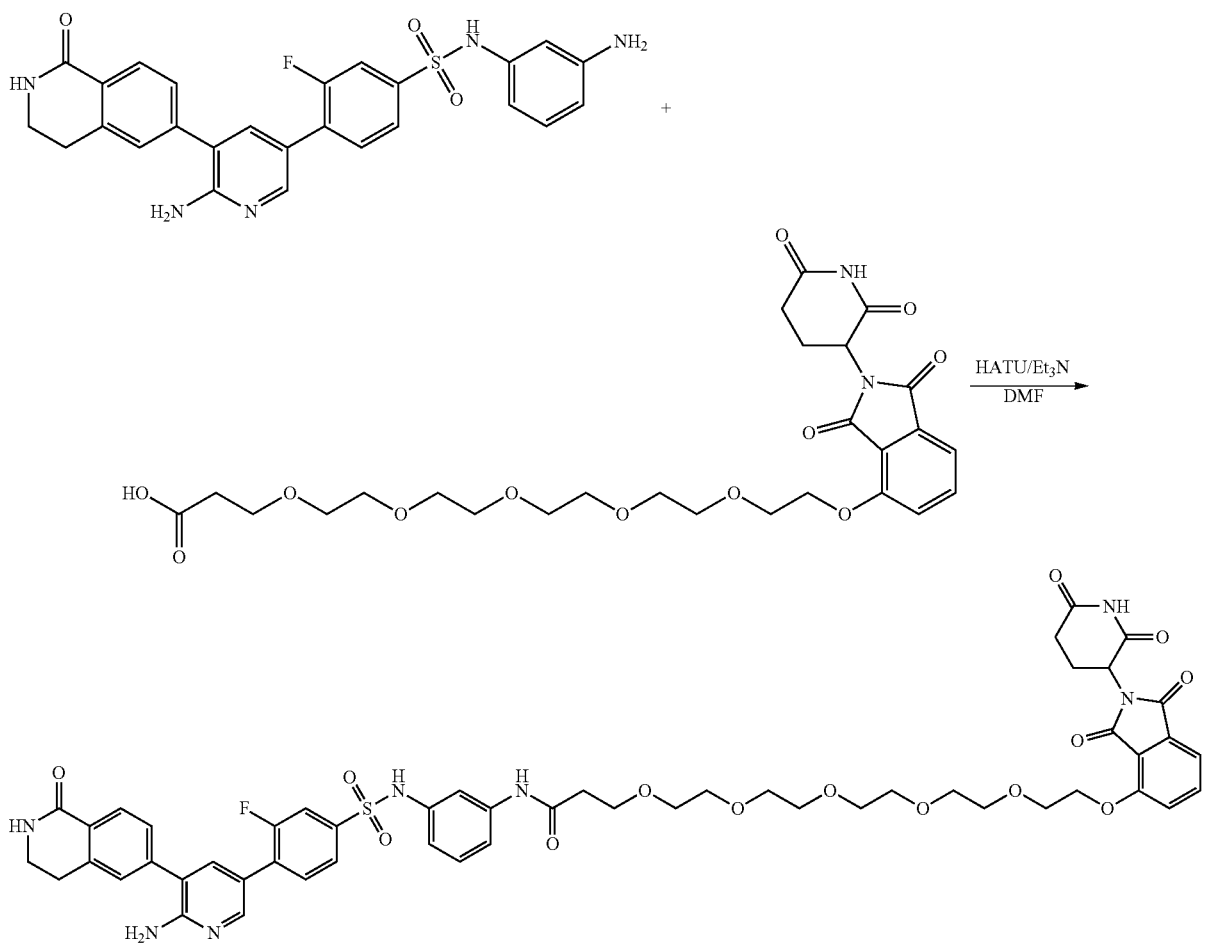

1-((2-(2,6-dioxopiperidin-3-yl)-1,3-dioxoisoindolin-4-yl)oxy)-3,6,9,12,15-pentaoxaoctadecan-18-oic acid (0.085g, 0.15 mmol) and HATU (0.091g, 0.24 mmol) were mixed in cation, followed by flash chromatography (5%-50% MeOH in EtOAc) to afford 55 mg I-17 (44%). LCMS (ESI) m/z 1052.44 [(M+H)$^+$; calcd for C$_{52}$H$_{55}$FN$_7$O$_{14}$S$^+$: 1052.35]

Example 22: N-(3-((4-(6-amino-5-(1-oxo-1,2,3,4-tetrahydroisoquinolin-6-yl)pyridin-3-yl)-N-cyclopropyl-3-fluorophenyl)sulfonamido)propyl)-1-((2-(2,6-dioxopiperidin-3-yl)-1,3-dioxoisoindolin-4-yl)oxy)-3,6,9,12,15-pentaoxaoctadecan-18-amide (I-23)

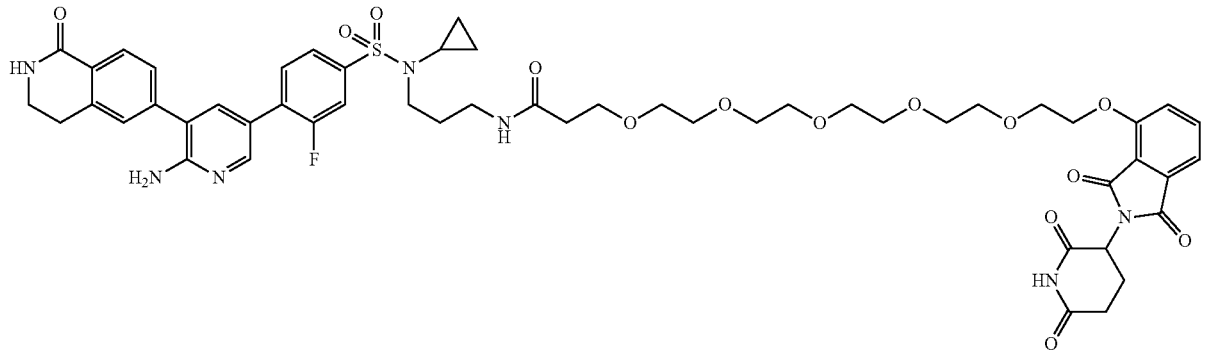 [SMILES: Nc1ncc(-c2ccc(S(=O)(=O)N(CCCNC(=O)CCOCCOCCOCCOCCOCCOc3cccc4c3C(=O)N(C3CCC(=O)NC3=O)C4=O)C3CC3)cc2F)cc1-c1ccc2c(c1)CCNC2=O]

The title compound was synthesized according to Example 21. N-(3-(4-(6-amino-5-(1-oxo-1,2,3,4-tetrahydroisoquinolin-6-yl)pyridin-3-yl)-N-cyclopropyl-3-fluorophenyl)sulfonamido)propyl)-1-((2-(2,6-dioxopiperidin-3-yl)-1,3-dioxoisoindolin-4-yl)oxy)-3,6,9,12,15-pentaoxaoctadecan-18-amide. LCMS (ESI) m/z 1058.54 [(M+H)$^+$; calcd for $C_{52}H_{60}FN_7O_4S^+$: 1058.15].

Example 23: N-(3-((4-(6-amino-5-(1-oxo-1,2,3,4-tetrahydroisoquinolin-6-yl)pyridin-3-yl)-3-fluorophenyl)sulfonamido)phenyl)-1-(2-((2-(2,6-dioxopiperidin-3-yl)-1,3-dioxoisoindolin-4-yl)oxy)acetamido)-3,6,9,12-tetraoxapentadecan-15-amide (I-16)

Step 1.

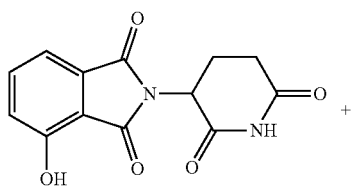

2-(2,6-dioxopiperidin-3-yl)-4-hydroxyisoindoline-1,3-dione (0.28g, 1.0 mmol) and t-butyl bromoacetate (0.24g, 1.2 mmol) in 3 mL DMF. K$_2$CO$_3$ (0.21g, 1.5 mmol) was added into the reaction. The mixture was firstly stirred at room temperature, then at 55° C. overnight. The mixture was cooled and filtered, then subjected to preparative HPLC to afford 0.33g product (85%). LCMS (ESI) m/z 333.18 (show as free acid instead of t-butyl ester)[(M+H)$^+$; calcd for $C_{19}H_{21}N_2O_7^+$: 389.13]

Step 2

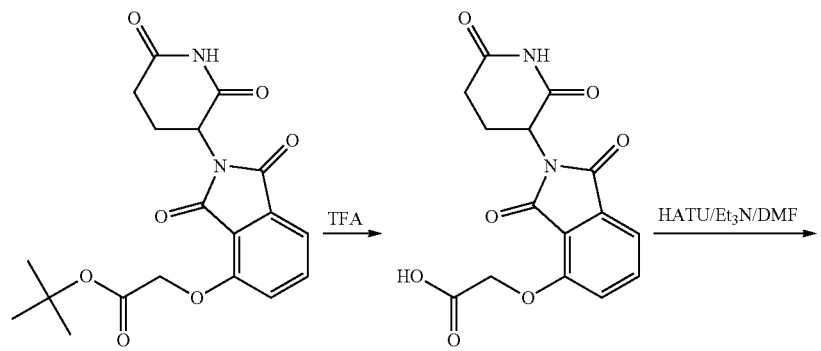

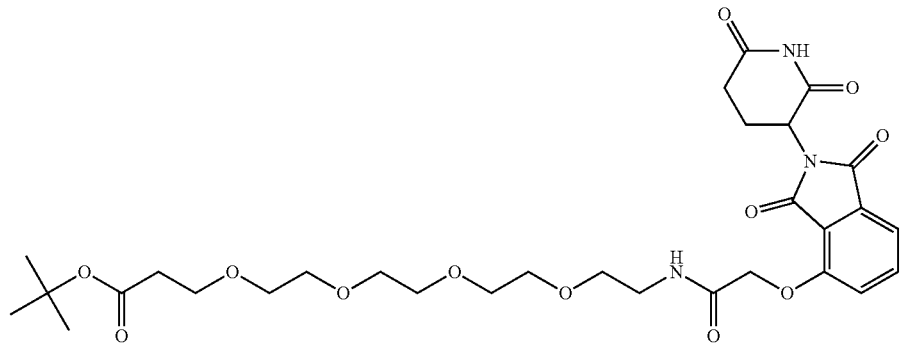

tert-butyl 2-((2-(2,6-dioxopiperidin-3-yl)-1,3-dioxoisoindolin-4-yl)oxy)acetate (0.06 mg, 0.13 mmol) was dissolved in 1 mL TFA. The solution was stirred at room temperature for 2 hours. Then the mixture was concentrated under reduced pressure to afford solid product, which was used in the following synthesis without further purification. Then the product from last step (0.043g, 0.13 mmol) was mixed with HATU (0.099g, 0.26 mmol) in 2 mL DMF with the presence of Et$_3$N (91 uL, 0.65 mmol). The mixture was stirred for 10 min before amino PEG-4-t-butyl ester (0.042g, 0.13 mmol) was added. The reaction was stirred at room temperature for 5 hours. The mixture was next subjected to direct preparative HPLC purification to afford 97 mg product (>100%). LCMS (ESI) m/z 580.22 (show as free acid instead of t-butyl ester) [(M+H)$^+$; calcd for $C_{30}H_{42}N_3O_{12}^+$: 636.28]

Step 3

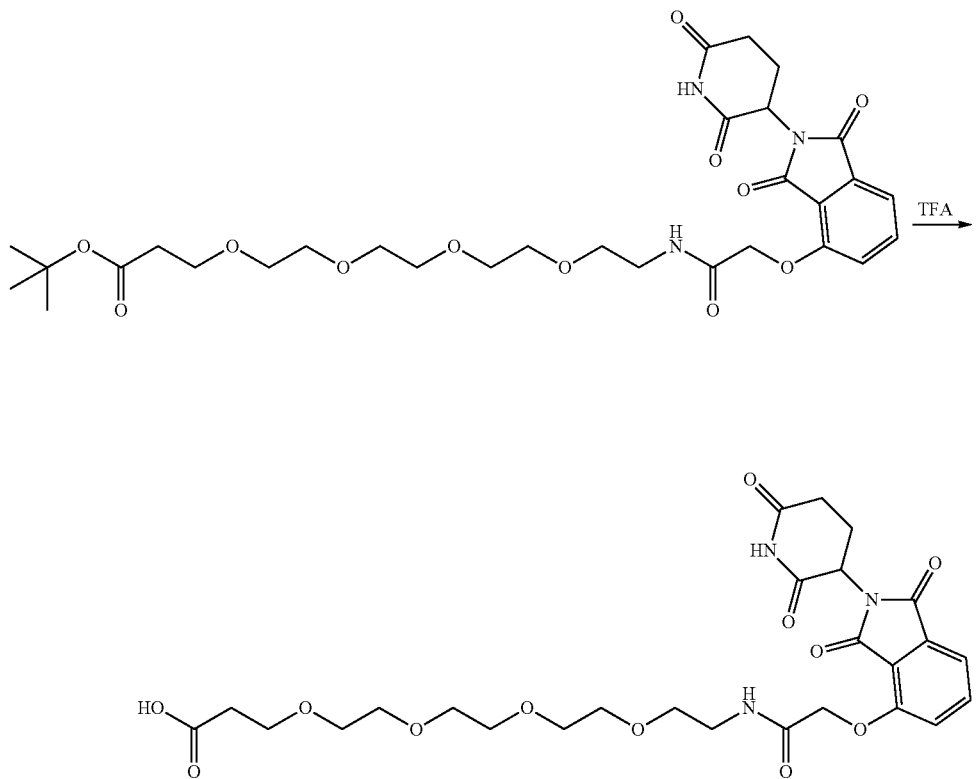

tert-butyl 1-((2-(2,6-dioxopiperidin-3-yl)-1,3-dioxoisoindolin-4-yl)oxy)-2-oxo-6,9,12,15-tetraoxa-3-azaoctadecan-18-oate (0.097g, 0.15 mmol) was dissolved in 2 mL TFA. The solution was stirred at room temperature for 2 hours. Then the mixture was concentrated under reduced pressure to afford solid product, which was used in the following synthesis without further purification.
Step 4

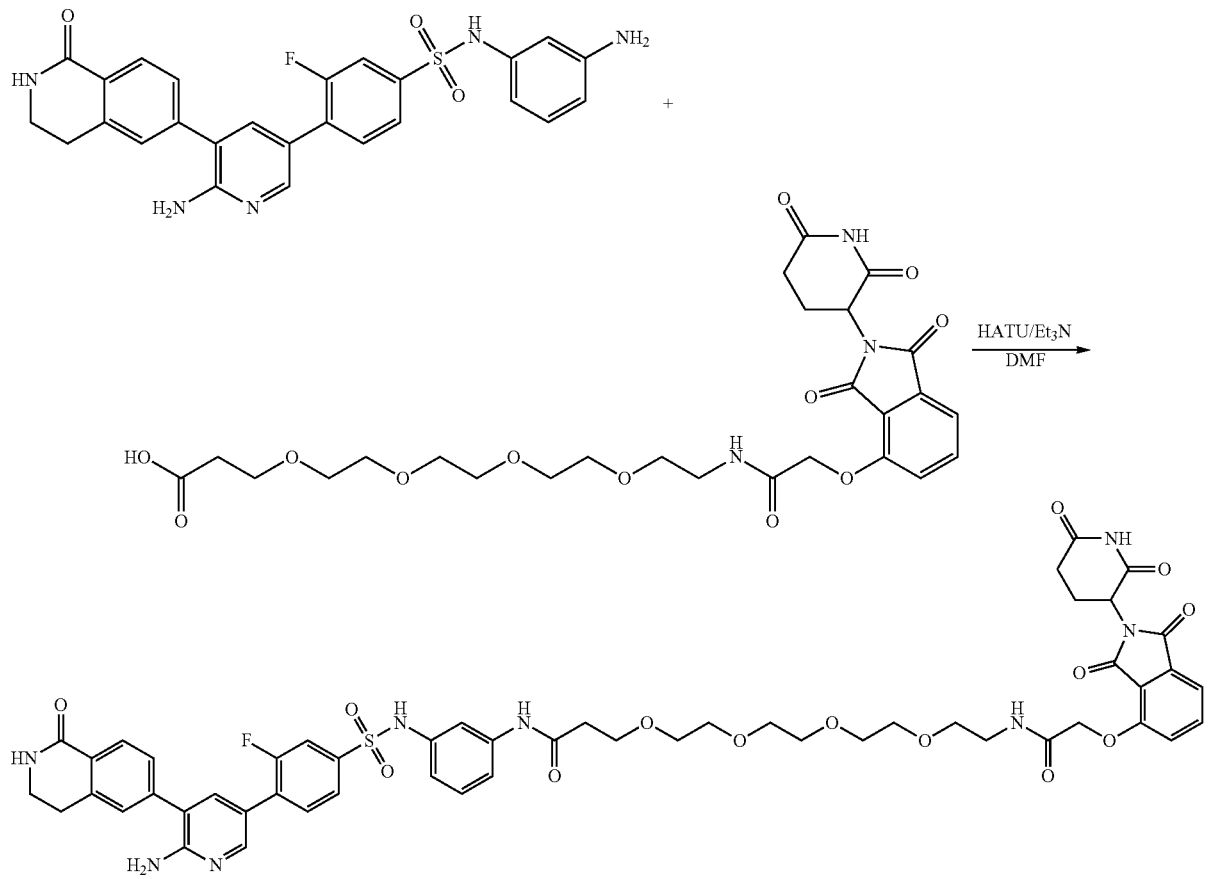

1-((2-(2,6-dioxopiperidin-3-yl)-1,3-dioxoisoindolin-4-yl)oxy)-2-oxo-6,9,12,15-tetraoxa-3-azaoctadecan-18-oic acid (0.089g, 0.15 mmol) and HATU (0.091g, 0.24 mmol) were mixed in 2 mL DMF. Et₃N (100 uL, 0.6 mmol) was added in the solution. The mixture was stirred for 10 min before 4-(6-amino-5-(1-oxo-1,2,3,4-tetrahydroisoquinolin-6-yl)pyridin-3-yl)-N-(3-aminophenyl)-3-fluorobenzenesulfonamide (15) (0.06g, 0.12 mmol) was added into the reaction. The reaction was then stirred at room temperature for 5 hours. The mixture was directly subjected to preparative HPLC purification, followed by flash chromatography (5%-50% MeOH in EtOAc) to afford 57 mg I-16 (45%). LCMS (ESI) m/z 1065.44 [(M+H)⁺; calcd for C₅₂H₅₄FN₈O₁₄S⁺: 1065.35]

Example 24: N-(3-((4-(6-amino-5-(1-oxo-1,2,3,4-tetrahydroisoquinolin-6-yl)pyridin-3-yl)-3-fluorophenyl)sulfonamido)phenyl)-5-(3-(2-(2-(2-((2-(2,6-dioxopiperidin-3-yl)-1,3-dioxoisoindolin-4-yl)amino)ethoxy)ethoxy)ethoxy)propanamido)pentanamide (I-13)

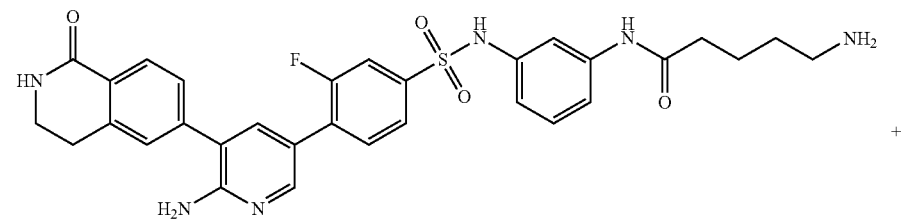

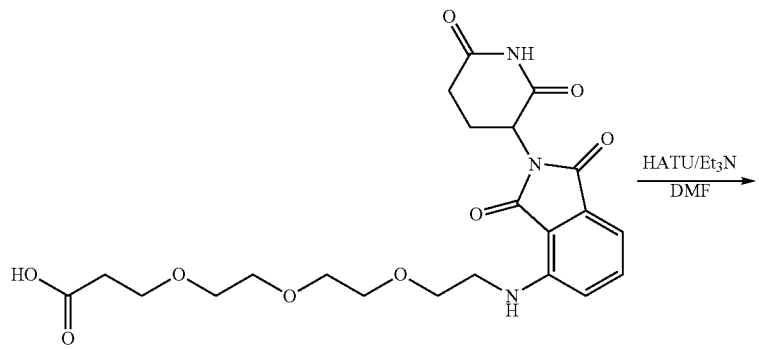

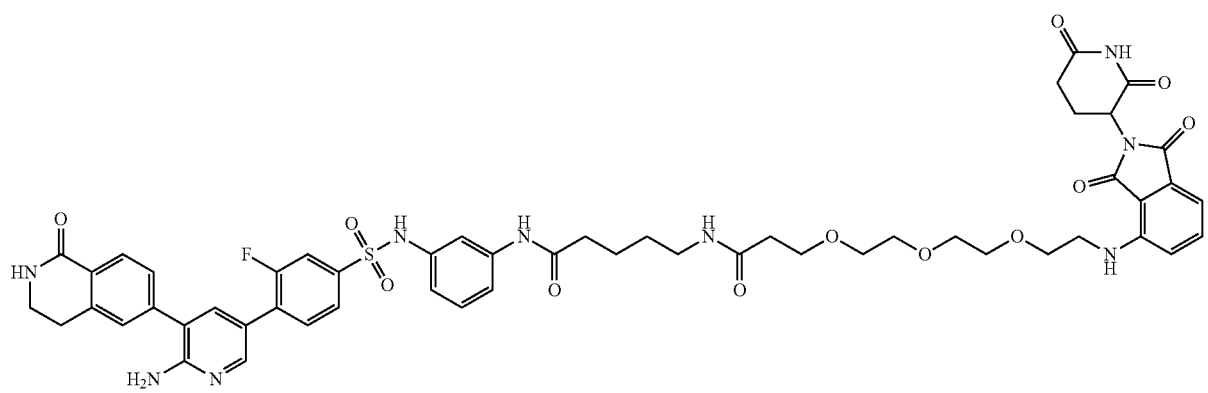

3-(2-(2-(2-((2-(2,6-dioxopiperidin-3-yl)-1,3-dioxoisoindolin-4-yl)amino)ethoxy)ethoxy)ethoxy)propanoic acid (0.02g, 0.04 mmol) and HATU (0.03g, 0.08 mmol) were mixed in 1 mL DMF. Et$_3$N (56 uL, 0.4 mmol) was added in the solution. The mixture was stirred for 10 min before 5-amino-N-(3-((4-(6-amino-5-(1-oxo-1,2,3,4-tetrahydroisoquinolin-6-yl)pyridin-3-yl)-3-fluorophenyl)sulfonamido)phenyl)pentanamide (0.025g, 0.04 mmol) was added into the reaction. The reaction was then stirred at room temperature for 3 hours. The mixture was directly subjected to preparative HPLC purification, followed by flash chromatography (0%-25% MeOH in EtOAc) to afford 14 mg product (33%). LCMS (ESI) m/z 1062.36 [(M+H)$^+$; calcd for C$_{53}$H$_{57}$FN$_9$O$_{12}$S$^+$: 1062.38])

Example 25: N-(3-((4-(6-amino-5-(1-oxo-1,2,3,4-tetrahydroisoquinolin-6-yl)pyridin-3-yl)-N-cyclopropyl-3-fluorophenyl)sulfonamido)propyl)-1-((2-(2,6-dioxopiperidin-3-yl)-1,3-dioxoisoindolin-4-yl)amino)-3,6,9,12,15-pentaoxaoctadecan-18-amide (I-24)

Step 1. 4-fluoro-2-(1-methyl-24-dioxopiperidin-3-yl)isoindoline-1,3-dione

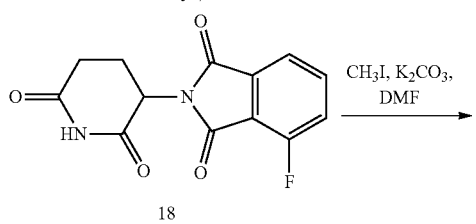

18

-continued

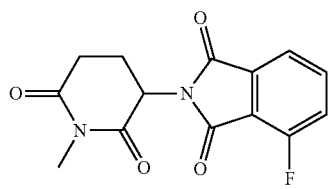

19

A mixture of 18 (280 mg, 1.015 mmol), iodomethane (158 mg, 1.117 mmol) and potassium carbonate (155 mg, 1.117 mmol) in anhydrous DMF (4 mL) was stirred at room temperature for 7 hours. The mixture was purified by prepare HPLC to afford 220 mg of product in 75% yield. LCMS (ESI) m/z 291.07 [(M+H)$^+$; calcd for $C_{14}H_{11}FN_2O_{4+}$: 291.08].

Step 2. tert-butyl 1-((2-(1-methyl-2,6-dioxopiperidin-3-yl)-1,3-dioxoisoindolin-4-yl)amino)-3,6,9,12,15-pentaoxaoctadecan-18-oate

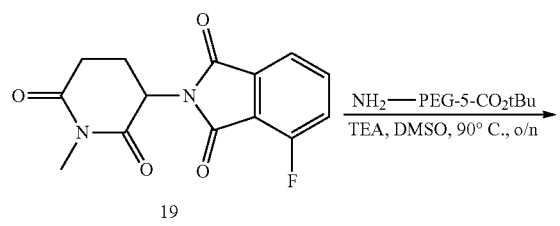

19

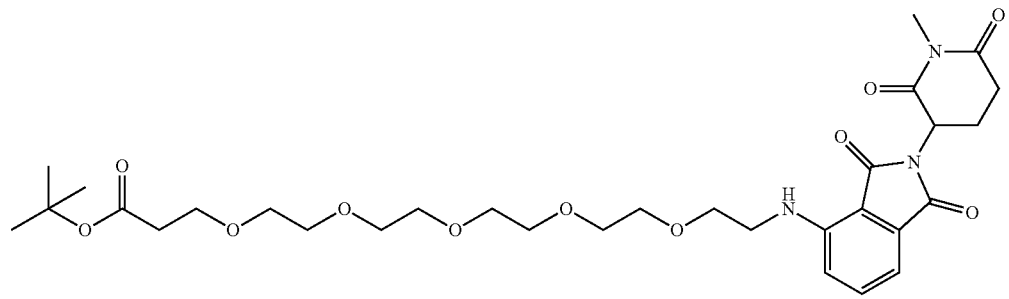

20

A mixture of 19 (220 mg, 0.756 mmol), NH$_2$-PEG-5-CO$_2$tBu (276 mg, 0.756 mmol) and TEA (0.21 mL, 1.51 mmol) in DMSO (5 mL) was stirred at 90° C. overnight. The mixture was purified by prepare HPLC to afford 225 mg product in 47% yield. LCMS (ESI) m/z 636.40 [(M+H)$^+$; calcd for $C_{31}H_{45}N_3O_{11}^+$: 635.71].

Step 3. 1-((2-(1-methyl-2,6-dioxopiperidin-3-yl)-1,3-dioxoisoindolin-4-yl)amino)-3,6,9,12,15-pentaoxaoctadecan-18-oic Acid

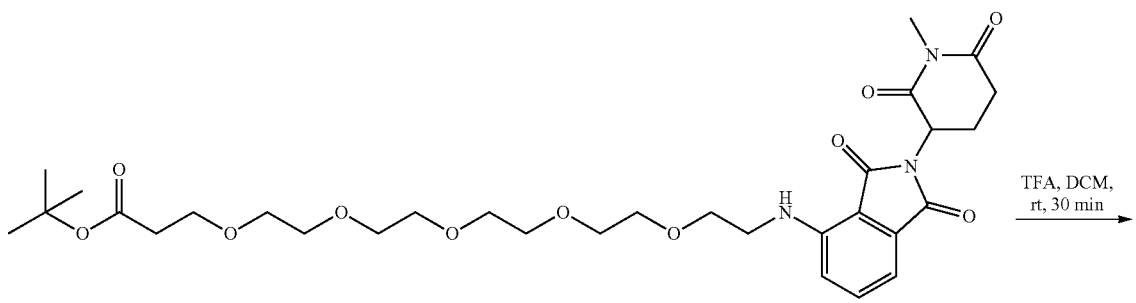

20

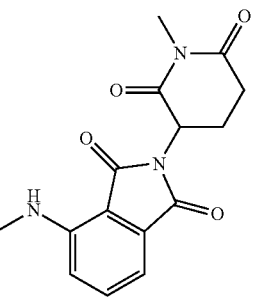

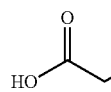

21

To a solution of 20 (100 mg, 0.157 mmol) in DCM (1 mL) was added TFA (1 mL), then stirred at room temperature for 30 min. The mixture was concentrated and purified by prepare HPLC to afford 83 mg product in 99% yield. LCMS (ESI) m/z 580.29 [(M+H)$^+$; calcd for $C_{27}H_{37}N_3O_{11}{}^+$: 579.60].

Step 4. N-(3-((4-(6-amino-5-(1-oxo-1,2,3,4-tetrahydroisoquinolin-6-yl)pyridin-3-yl)-N-cyclopropyl-3-fluorophenyl)sulfonamido)propyl)-1-((2-(2,6-dioxopiperidin-3-yl)-1,3-dioxoisoindolin-4-yl)amino)-3,6,9,12,15-pentaoxaoctadecan-18-amide (I-24)

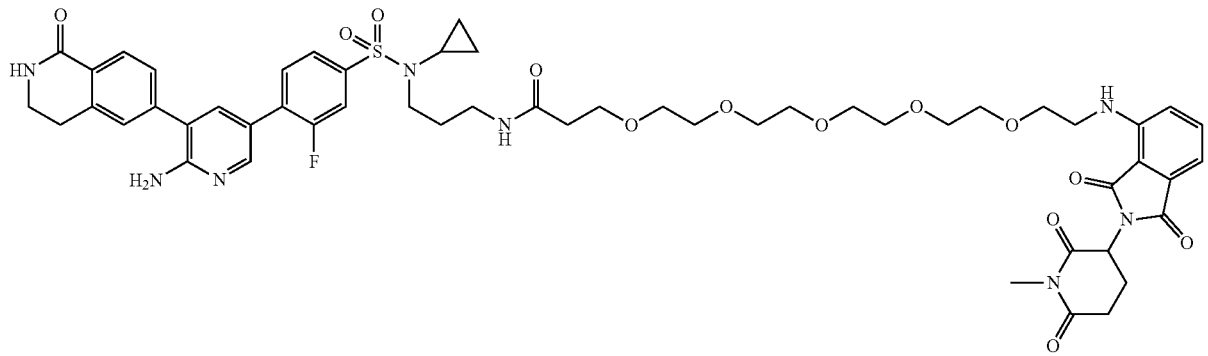 [SMILES: CN1C(=O)CCC(N2C(=O)c3cccc(NCCOCCOCCOCCOCCOCCC(=O)NCCCN(C4CC4)S(=O)(=O)c4ccc(-c5cnc(N)c(-c6ccc7c(c6)CCNC7=O)c5)c(F)c4)c3C2=O)C1=O]

N-(3-((4-(6-amino-5-(1-oxo-1,2,3,4-tetrahydroisoquinolin-6-yl)pyridin-3-yl)-N-cyclopropyl-3-fluorophenyl)sulfonamido)propyl)-1-((2-(1-methyl-2,6-dioxopiperidin-3-yl)-1,3-dioxoisoindolin-4-yl)amino)-3,6,9,12,15-pentaoxaoctadecan-18-amide. LCMS (ESI) m/z 1071.64 [(M+H)$^+$; calcd for $C_{53}H_{63}FN_8O_{13}S^+$: 1071.19].

Example 26: Cell Viability and Proliferation Assay

Cell Culture and Reagents
Cells and Culture.
Dexamethasone-sensitive MM.1S human MM cell line were kindly provided by Dr. Steven Rosen (Northwestern University, Chicago, Ill., United States). Creblon stable knockout MM.1S cells were established in our laboratory using lentiviral CRBN shRNA system. The cell lines were routinely tested for Mycoplasma, and genotyped with two different methods. Peripheral blood mononuclear cells were obtained from healthy volunteer by Ficoll-Paque centrigution. All MM cell lines and PBMCs were cultured in RPMI-1640 media (EuroClone, Pero, Italy) containing 10% fetal bovine serum (FBS, GIBCO, Life technologies, Carlsbad, Calif., United States), and a mix of penicillin and streptomycin to 1% from EuroClone (ECB3001).

Cell Proliferation Assays and Growth Assays
MM.1S and CRBN-knockout MM.1S cells were counted and diluted to a final concentration of 400,000 cells/mL. The cell were plated in 96-well plates and mixed with an equal volume of culture media containing DMSO or increasing concentration of a compound of the present application diluted in DMSO (the final DMSO concentration is equal between all tested samples), using a STARlet Robot (Hamiltonrobotics, Reno, Nev., United States). Cells with increasing concentration of compound of the present application and DMSO were harvested at different time points (24 hrs to 72 hrs). For assessment of celll growth MTT assay, the 3-[4,5 dimethylthiazol-2-yl]-2,5 diphenyltetrazolium bromide-MTT (Sigma-Aldrich, St. Louis, Mo., Unites States) colorimetric assay was used. At the various time points (24-72 hrs), 10 μL of 5 mg/mL MTT were added to cells. After 4 hrs incubation at 37° C., medium was discarded and 100 μL MTT stop solution (Isopropanol with 1 N HCl) was used to dissolve MTT metabolic products. Absorbance was read at 570/630 nm.

Western Blotting
MM.1S and CRBN knockout MM.1S cells were counted, diluted and plated in six-well plates to a final concentration of 500,000 cells/well. Cells were then harvested with DMSO or different concentration of a compound of the present application (4 h-24 h). MM cells were then collected and centrifuged for 5 min, 1300 rpm at RT. The pellets were re-suspended in cell lysis buffer (20 mM Tris-HCl (pH 7.5), 150 mM NaCl, 1 mM Na2EDTA, 1 mM EGTA, 1% Triton, 2.5 mM sodium pyrophosphate, 1 mM beta-glycerophosphate, 1 mM Na3VO4, 1 μg/ml leupeptin. Cell lysates were subjected to sodium dodecyl sulfate-polyacrylamide gel electrophoresis SDS-PAGE, transferred to nitrocellulose membranes, and immunoblotted with different antibodies: MST1 (STK4) (#14946), K48-linkage Specific Polyubiquitin (#8081) and GAPDH (#5174) from Cell Signaling, Beverly, Mass., United States: IKZF1 (AF4984) (from R&D Systems, Mineapolis, Minn., United States). All antibodies were diluted 1:1000, except for GAPDH antibody (1:4,000 dilution).

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:

1. A compound of Formula I:

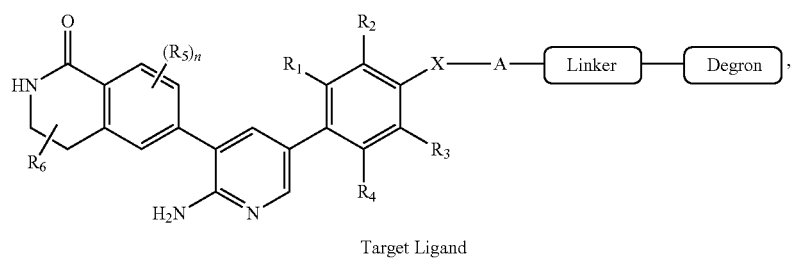

or a stereoisomer or pharmaceutically acceptable salt thereof,
wherein:
  A is phenylene, ($C_1$-$C_4$) alkylene, ($C_3$-$C_6$) cycloalkylene, or heterocyclylene comprising one 5- or 6-membered ring and 1 to 3 heteroatoms selected from N, O, and S, wherein the phenylene, alkylene, cycloalkylene, or heterocyclylene is optionally substituted with one or more ($C_1$-$C_3$) alkyl, ($C_1$-$C_3$) alkoxy, $NO_2$, $NH_2$, or halogen;
  X is $NR_xS(O)_m$, $S(O)_mNR_x$, $NR_xC(O)$, $C(O)NR_x$, or $NR_x$;
  $R_x$ is H, ($C_1$-$C_3$) alkyl, or ($C_3$-$C_6$) cycloalkyl;
  $R_1$ is H, ($C_1$-$C_3$) alkyl, ($C_1$-$C_3$) alkoxy, $NO_2$, or halogen;
  $R_2$ is H, ($C_1$-$C_3$) alkyl, ($C_1$-$C_3$) alkoxy, $NO_2$, or halogen;
  $R_3$ is H, ($C_1$-$C_3$) alkyl, ($C_1$-$C_3$) alkoxy, $NO_2$, or halogen;
  $R_4$ is H, ($C_1$-$C_3$) alkyl, ($C_1$-$C_3$) alkoxy, $NO_2$, or halogen;
  each $R_5$ is independently ($C_1$-$C_4$) alkyl, $C(O)NR_7R_8$, CN, OH, or halogen;
  $R_6$ is H, ($C_1$-$C_4$) alkyl, ($C_1$-$C_4$) alkoxy, or halogen;
  $R_7$ and $R_8$ are each independently H or ($C_1$-$C_4$) alkyl;
  m is 0, 1, or 2; and
  n is 0, 1, 2, or 3,
  the Targeting Ligand is capable of binding to STK4;
  the Linker is a group that covalently binds to the Targeting Ligand and the Degron; and the Degron is of Formula D1:

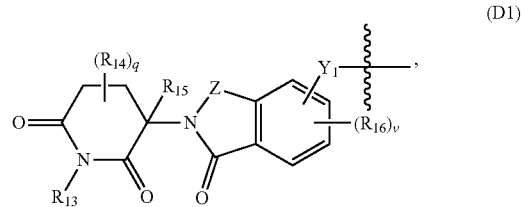

or a stereoisomer thereof, wherein:
  $Y_1$ is a bond, $(CH_2)_{1-6}$, $(CH_2)_{0-6}$-O, $(CH_2)_{0-6}$-C(O)$NR_{11}$, $(CH_2)_{0-6}$-$NR_{11}$C(O), $(CH_2)_{0-6}$-NH, or $(CH_2)_{0-6}$-$NR_{12}$;
  Z is C(O) or C($R_{13}$)$_2$;
  $R_{11}$ is H or $C_1$-$C_6$ alkyl;
  $R_{12}$ is $C_1$-$C_6$ alkyl or C(O)-$C_1$-$C_6$ alkyl;
  each $R_{13}$ is independently H or $C_1$-$C_3$ alkyl;
  each $R_{14}$ is independently $C_1$-$C_3$ alkyl;
  $R_{15}$ is H, deuterium, $C_1$-$C_3$ alkyl, F, or Cl;
  each $R_{16}$ is independently halogen, OH, $C_1$-$C_6$ alkyl, or $C_1$-$C_6$ alkoxy;
  q is 0, 1, or 2; and
  v is 0, 1, 2, or 3,
  wherein the Degron is covalently bonded to a Linker via

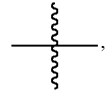

wherein:
  when $Y_1$ is $(CH_2)_{1-6}$-O, $Y_1$ can be bonded to the Degron via either the carbon atom or the oxygen atom,
  when $Y_1$ is $(CH_2)_{1-6}$-C(O)$NR_{11}$, $(CH_2)_{1-6}$-NH, or $(CH_2)_{1-6}$-$NR_{12}$, $Y_1$ can be bonded to the Degron via either the carbon atom or the nitrogen atom, and
  when $Y_1$ is $(CH_2)_{1-6}$-$NR_{11}$(O), $Y_1$ can be bonded to the Degron via either the carbon atom in the $CH_2$ moiety or the carbon atom in the C(O) moiety.

2. The compound of claim 1, wherein A is phenylene optionally substituted with one or more ($C_1$-$C_3$) alkyl, ($C_1$-$C_3$) alkoxy, $NO_2$, $NH_2$, or halogen.

3. The compound of claim 1, wherein A is ($C_1$-$C_4$) alkylene optionally substituted with one or more ($C_1$-$C_3$) alkyl, ($C_1$-$C_3$) alkoxy, $NO_2$, $NH_2$, or halogen.

4. The compound of claim 1, wherein A is heterocyclylene optionally substituted with one or more ($C_1$-$C_3$) alkyl, ($C_1$-$C_3$) alkoxy, $NO_2$, $NH_2$, or halogen.

5. The compound of claim 1, wherein X is $NR_xS(O)_2$ or $S(O)_2NR_x$.

6. The compound of claim 1, wherein $R_1$ is H.

7. The compound of claim 1, wherein $R_2$ is H.

8. The compound of claim 1, wherein $R_3$ is H.

9. The compound of claim 1, wherein $R_4$ is H.

10. The compound of claim 1, wherein $R_4$ is F.

11. The compound of claim 1, wherein n is 0.

12. The compound of claim 1, wherein $R_6$ is H.

13. The compound of claim 1, wherein the Degron of Formula D1 is of Formula D1a, D1b, D1c, D1d, D1e, D1f, D1g, D1h, D1i, D1j, D1k, or D1l:

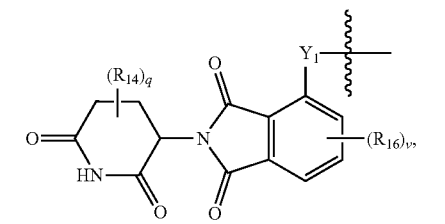

(D1a)

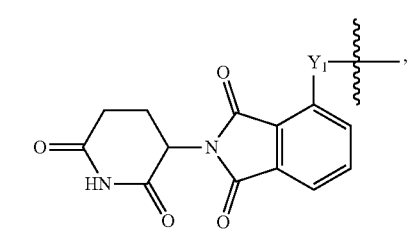

(D1b)

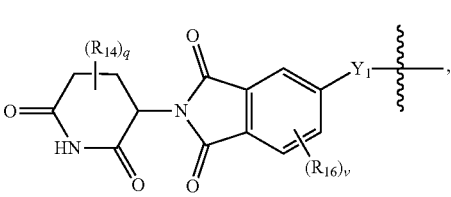

(D1c)

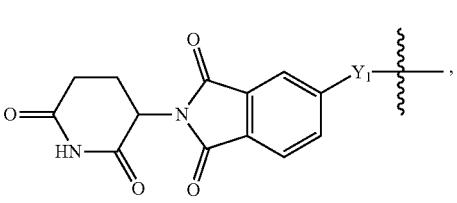

(D1d)

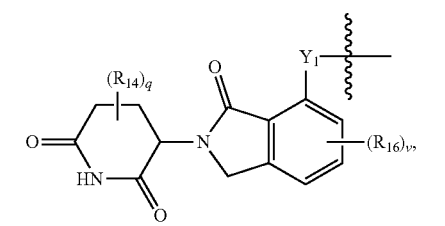

(D1e)

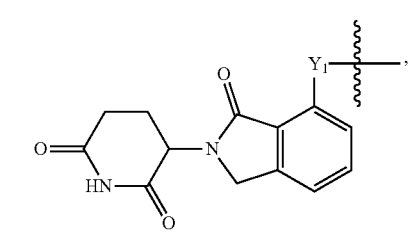

(D1f)

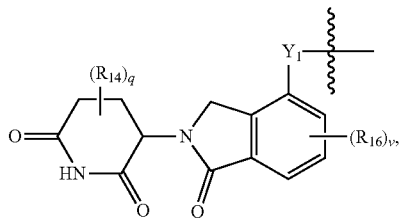

(D1g)

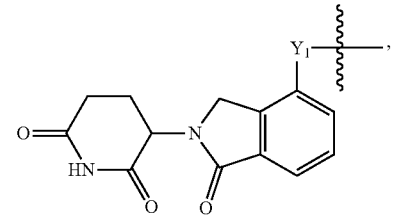

(D1h)

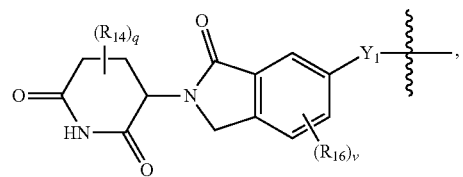

(D1i)

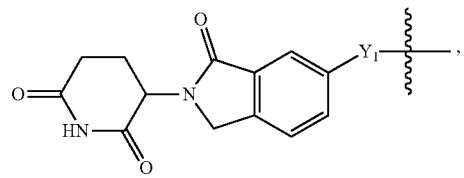

(D1j)

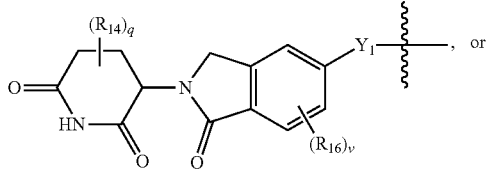

(D1k)

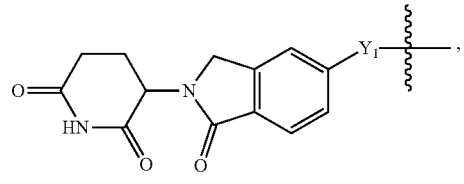

(D1l)

or a stereoisomer thereof.

14. The compound of claim 1, wherein the Linker is of Formula L0:

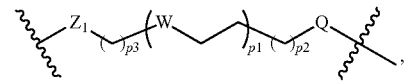

(L0)

or a stereoisomer thereof, wherein
p1 is an integer selected from 0 to 12;
p2 is an integer selected from 0 to 12;
p3 is an integer selected from 1 to 6;
each W is independently absent, NHC(O), C(O)NH, $CH_2$, O, S, or NH;

$Z_1$ is absent, $OCH_2C(O)NH$, $CH_2C(O)NH$, $OC(O)NH$, $C(O)NH$, $C(O)$, $CH_2$, $O$, or $NH$; and Q is absent, $NHC(O)CH_2$, or $O(CH_2)_{0-2}$, wherein the Linker is covalently bonded to a Degron via the

next to Q, and covalently bonded to a Targeting Ligand via the

next to $Z_1$ wherein:
- when Q is $NHC(O)CH_2$, Q can be bonded to a Degron via either the carbon atom or the nitrogen atom,
- when Q is $O(CH_2)_{1-2}$, Q can be bonded to a Degron via either the carbon atom or the oxygen atom,
- when $Z_1$ is $OCH_2C(O)NH$ or $OC(O)NH$, $Z_1$ can be bonded to a Targeting Ligand via either the oxygen atom or the nitrogen atom, and
- when $Z_1$ is $CH_2C(O)NH$ or $C(O)NH$, $Z_1$ can be bonded to a Targeting Ligand via either the carbon atom or the nitrogen atom.

15. The compound of claim 14, wherein the Linker of Formula L0 has the structure selected from:

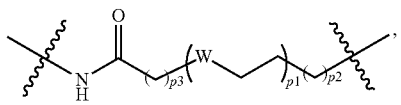 (L1)

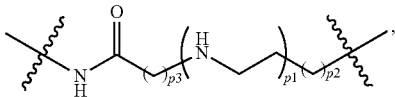 (L2)

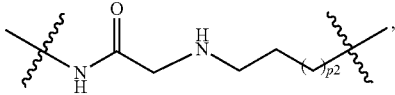 (L3)

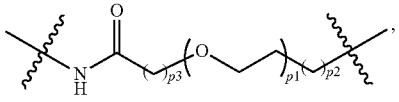 (L4)

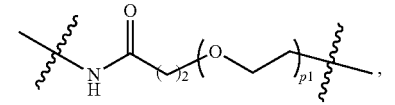 (L5)

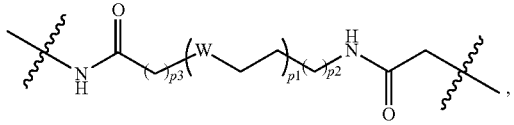 (L6)

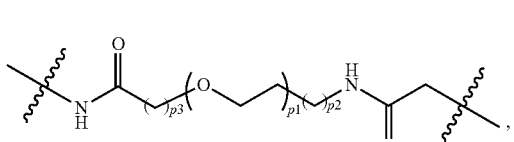 (L7)

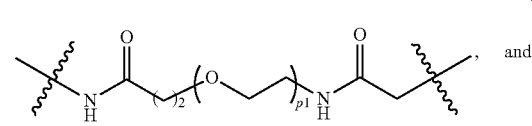 (L8), and

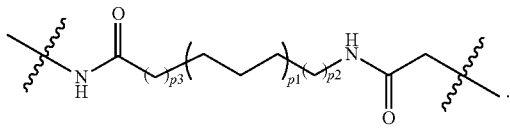 (L9).

16. The compound of claim 1, selected from:

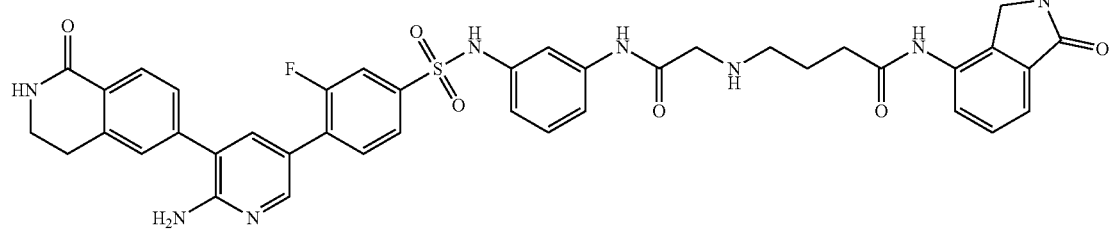 (I-1)

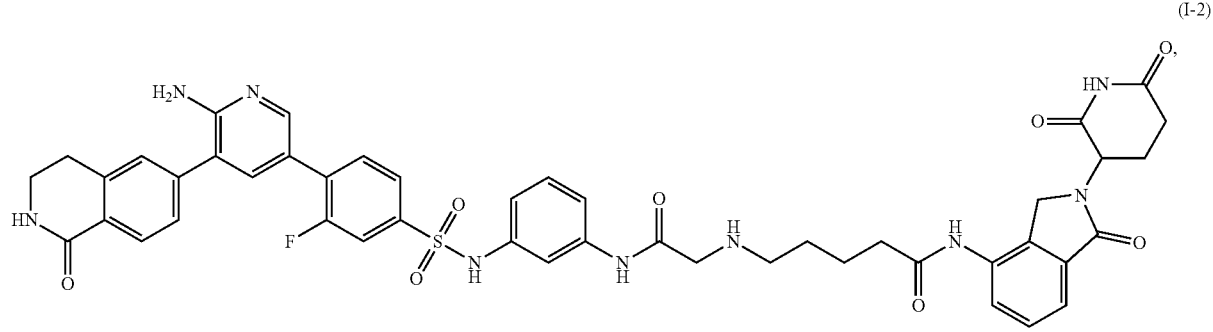
(I-2)
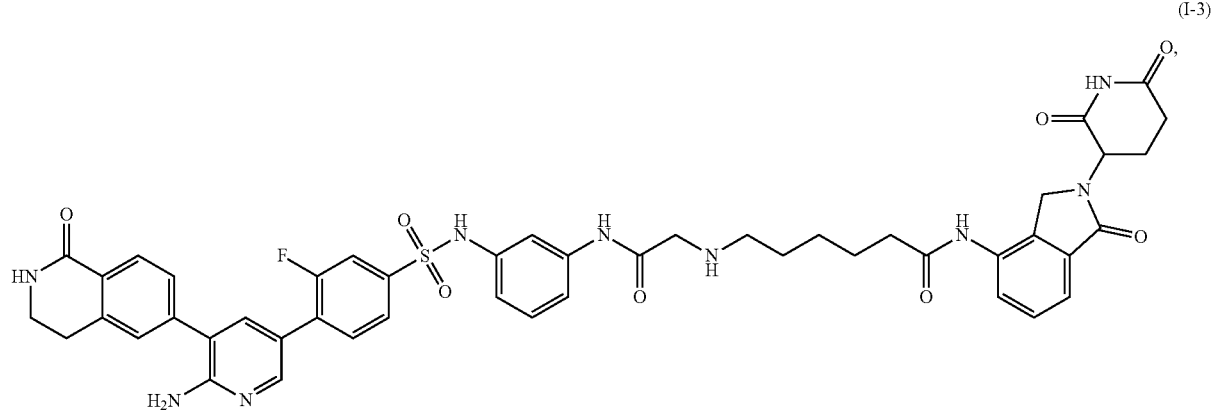
(I-3)
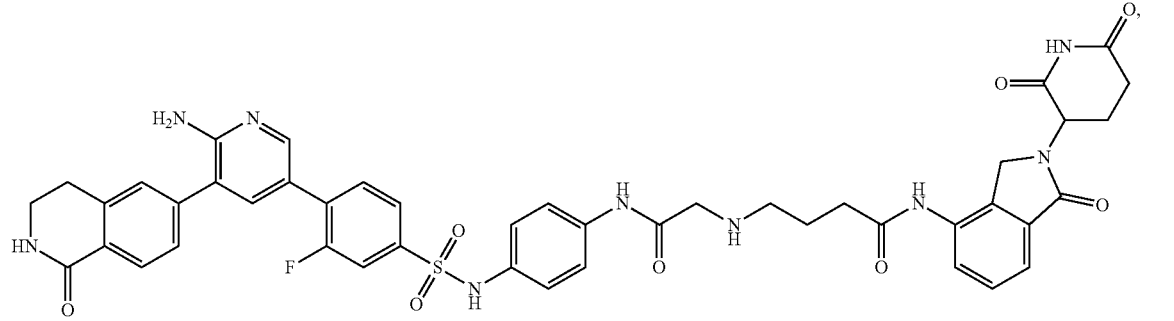
(I-4)
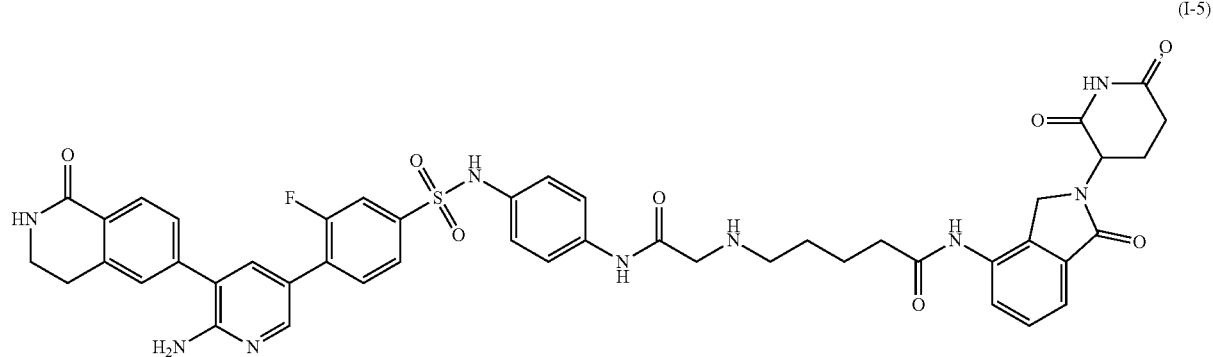
(I-5)

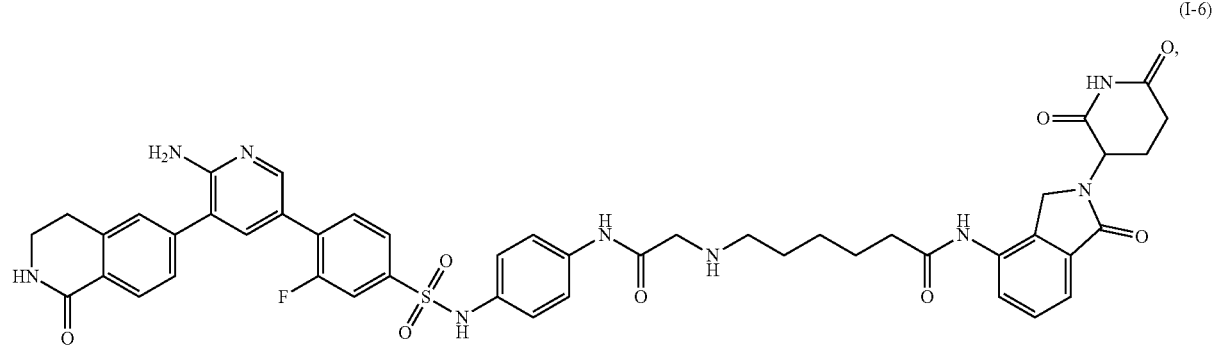
(I-6)
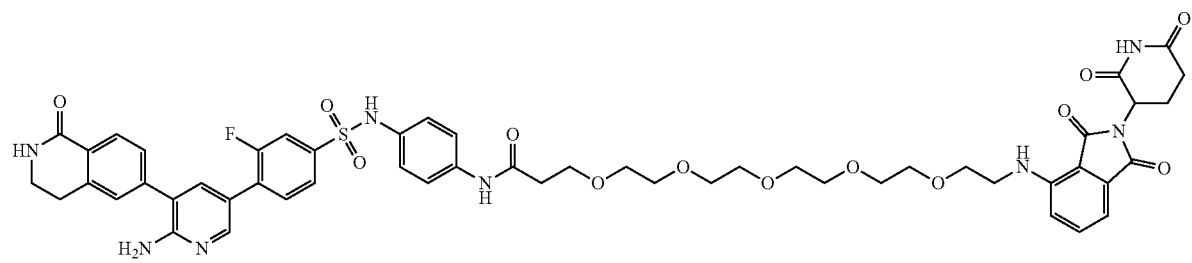
(I-7)
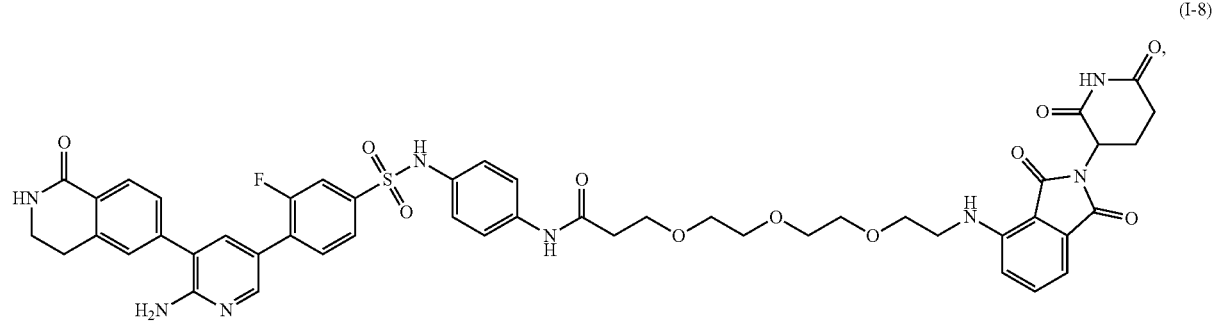
(I-8)
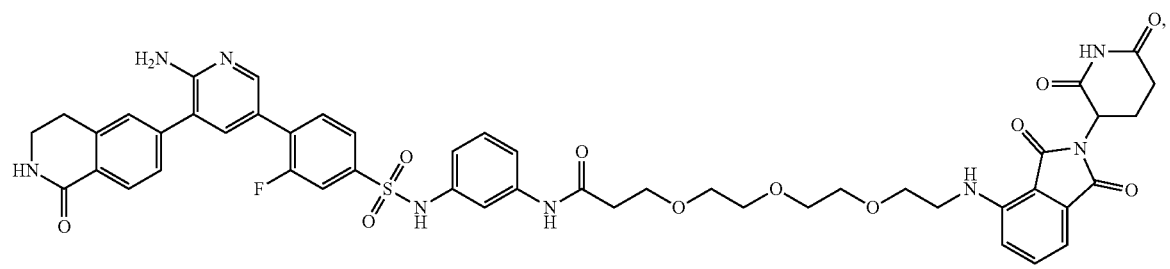
(I-9)
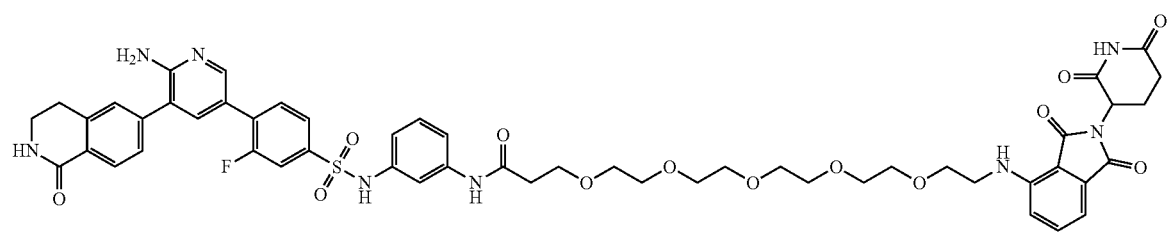
(I-10)

(I-11)
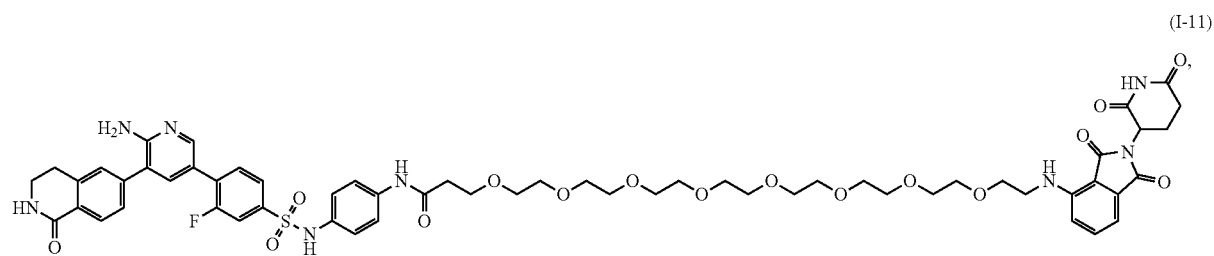
(I-12)
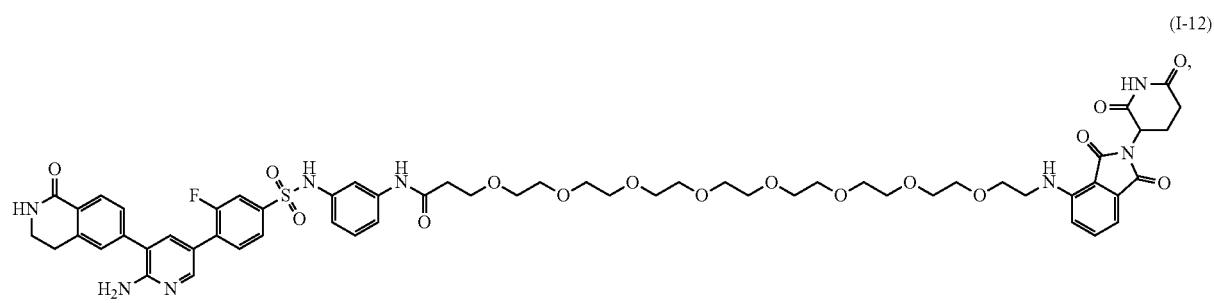
(I-13)
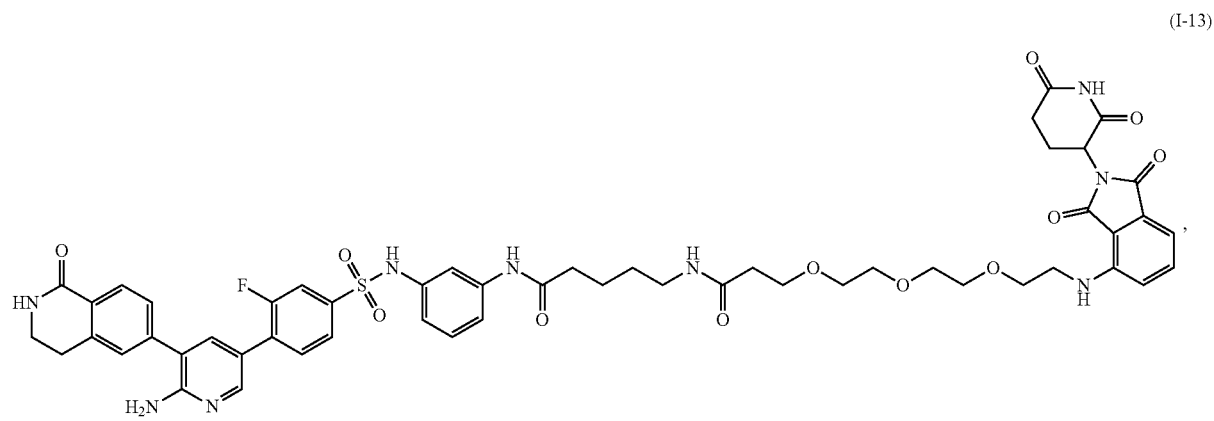
(I-14)
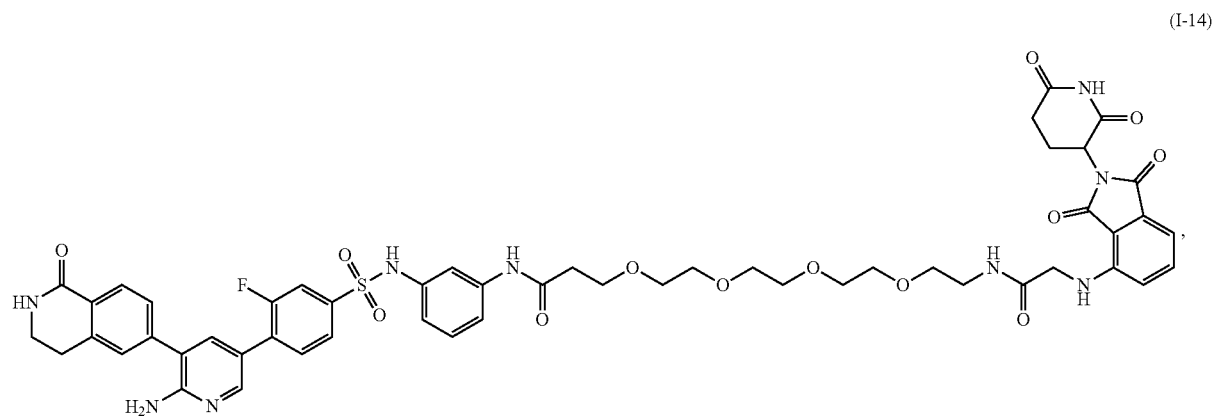

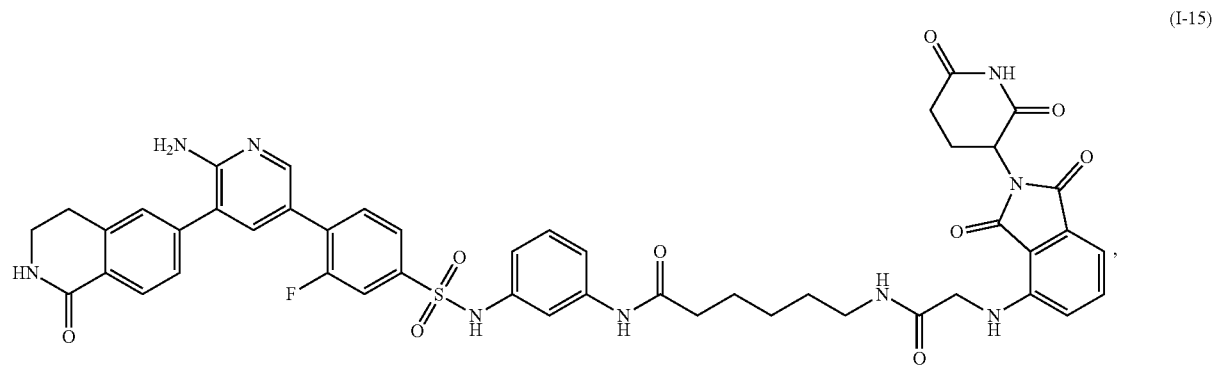
(I-15)
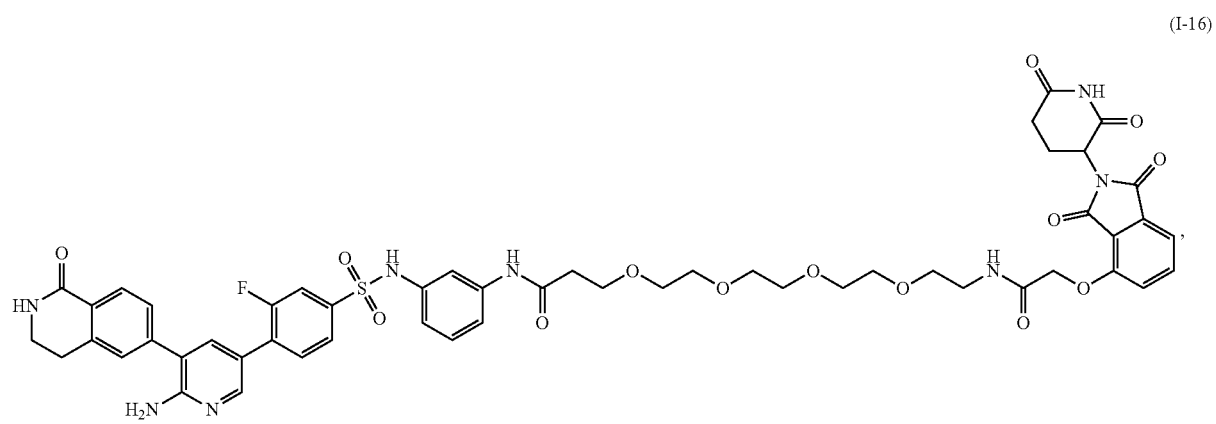
(I-16)
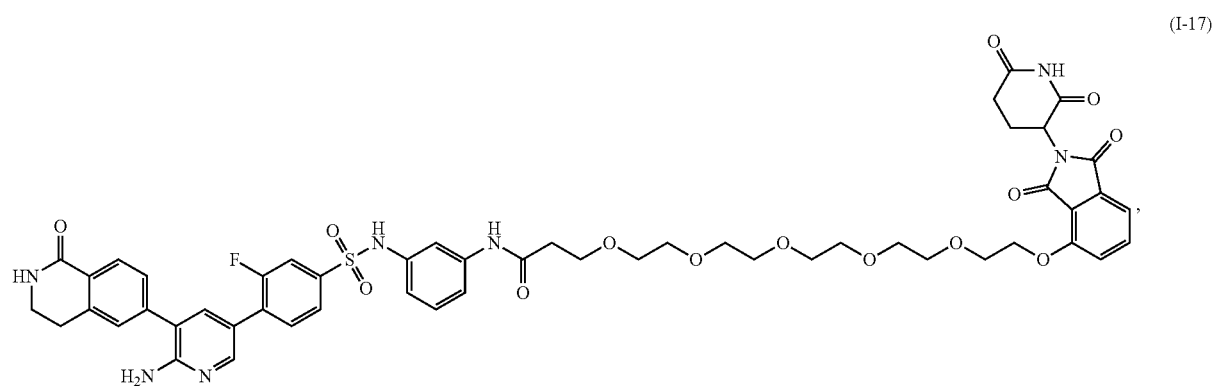
(I-17)
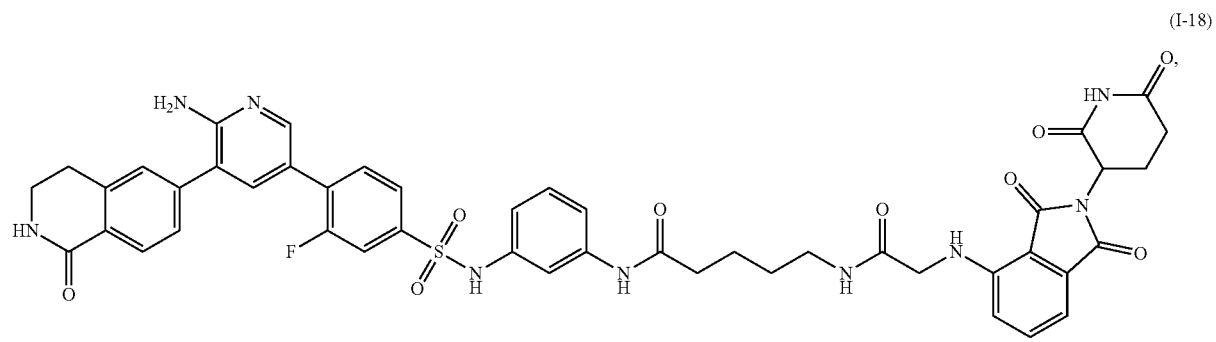
(I-18)

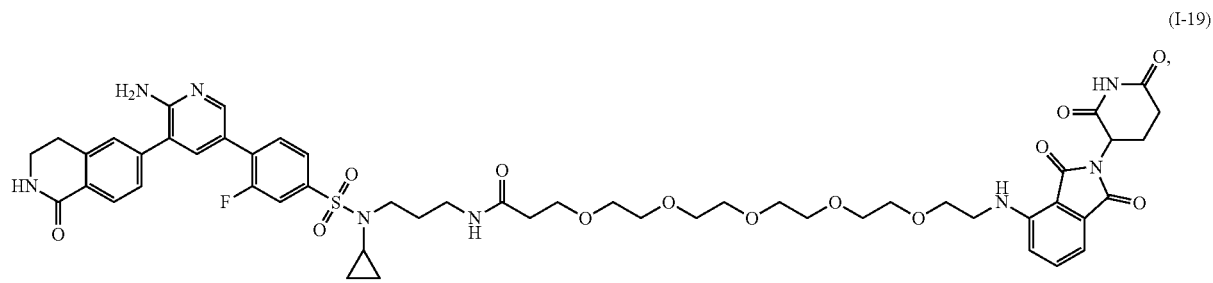
(I-19)
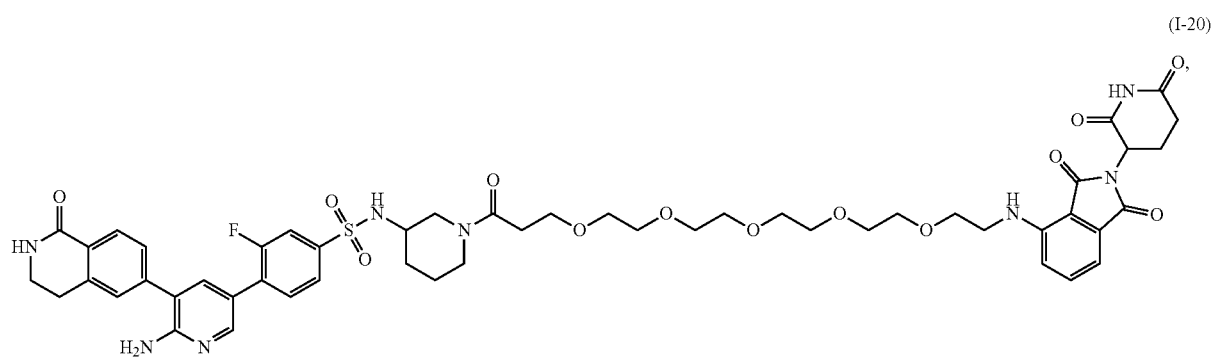
(I-20)
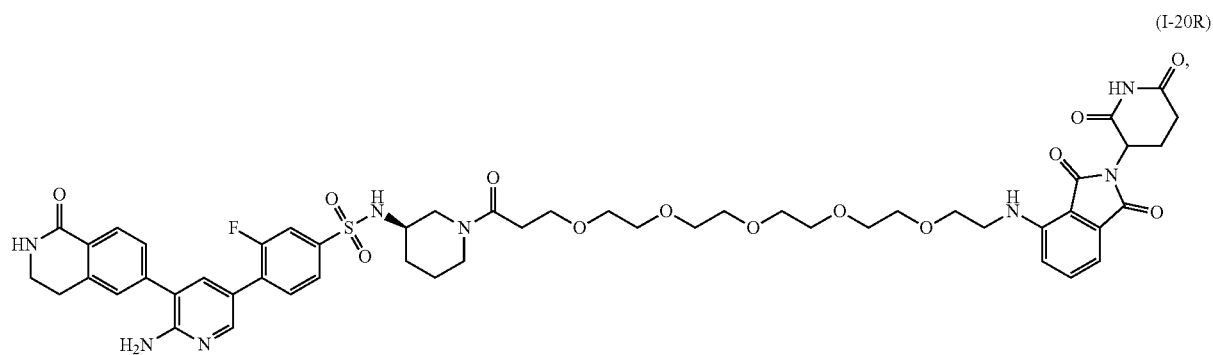
(I-20R)
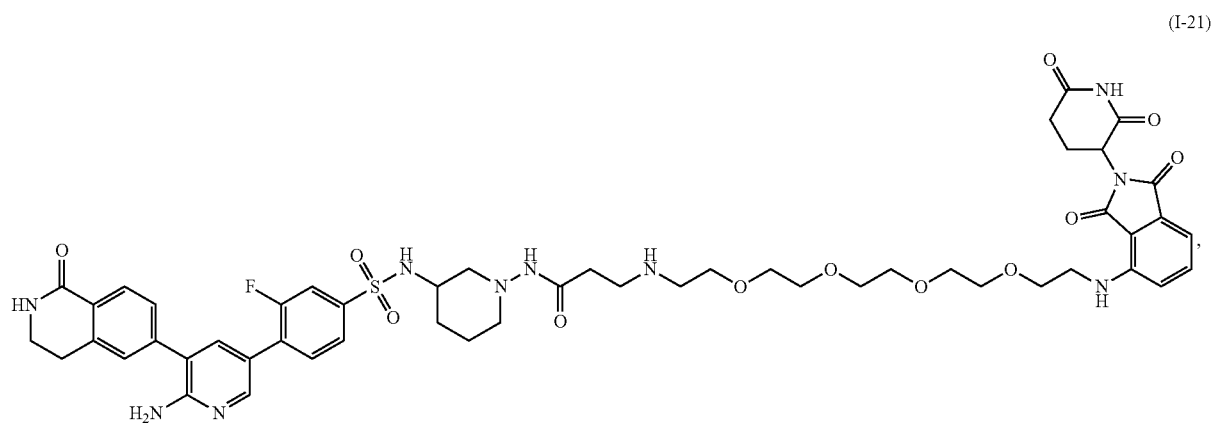
(I-21)

-continued (I-22)
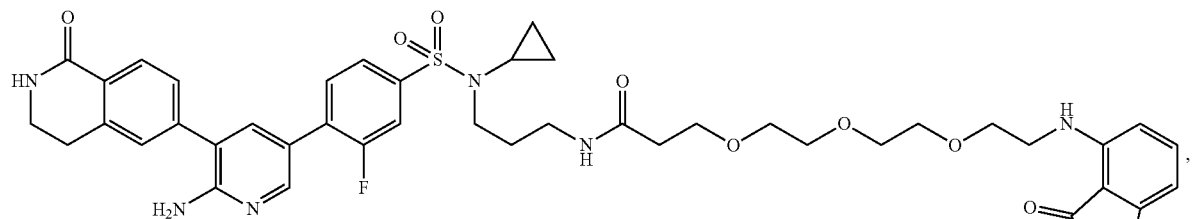

(I-23)
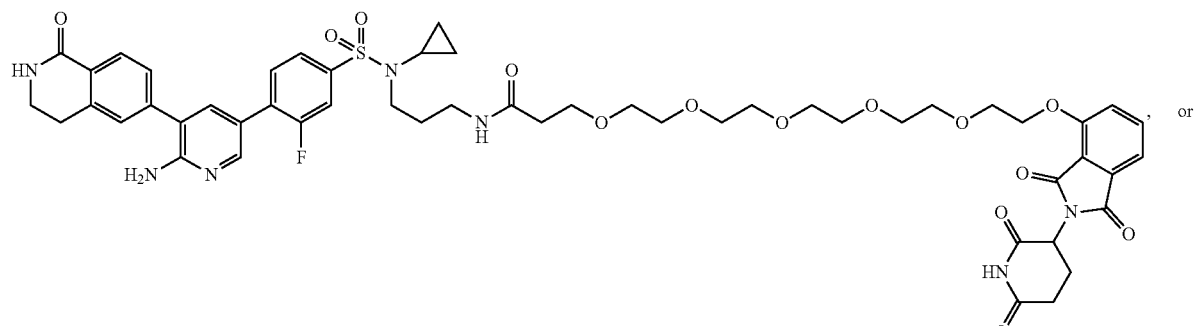
or (I-24)
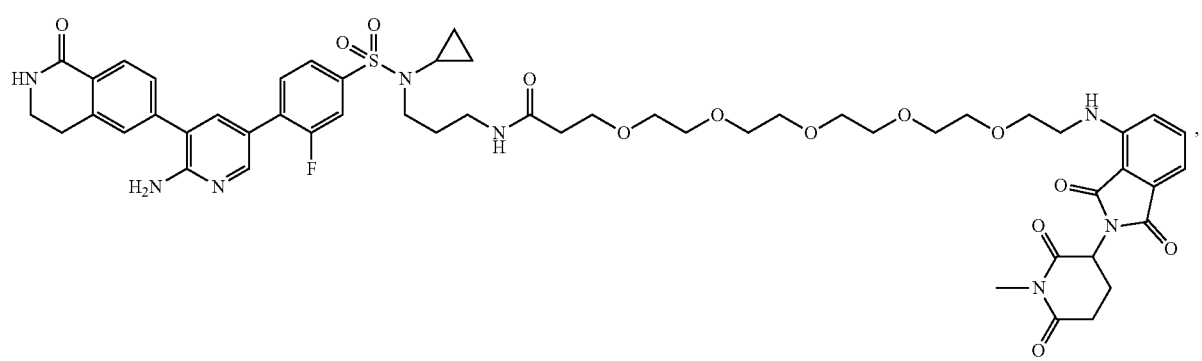

or a stereoisomer or pharmaceutically acceptable salt thereof.

17. A pharmaceutical composition comprising a compound of claim 1 or a stereoisomer or pharmaceutically acceptable salt thereof, and a pharmaceutically acceptable carrier.

18. A method of treating cancer or hematopoietic disorder which is mediated by STK4, comprising administering to a subject in need thereof an effective amount of a compound of claim 1, or a pharmaceutically acceptable salt or stereoisomer thereof.

19. A method of modulating the amount of STK4 and/or of YAP1, comprising administering to a subject in need thereof an effective amount of a compound of claim 1, or a pharmaceutically acceptable salt or stereoisomer thereof.

20. The method of claim 18, wherein the cancer is multiple myeloma.

* * * * *

UNITED STATES PATENT AND TRADEMARK OFFICE
CERTIFICATE OF CORRECTION

PATENT NO. : 11,447,467 B2  
APPLICATION NO. : 16/769059  
DATED : September 20, 2022  
INVENTOR(S) : Sara Buhrlage et al.

Page 1 of 1

It is certified that error appears in the above-identified patent and that said Letters Patent is hereby corrected as shown below:

In the Claims

Column 151-152, Line 4 In Claim 16:
Delete the fourth structure, i.e., I-21, as follows:

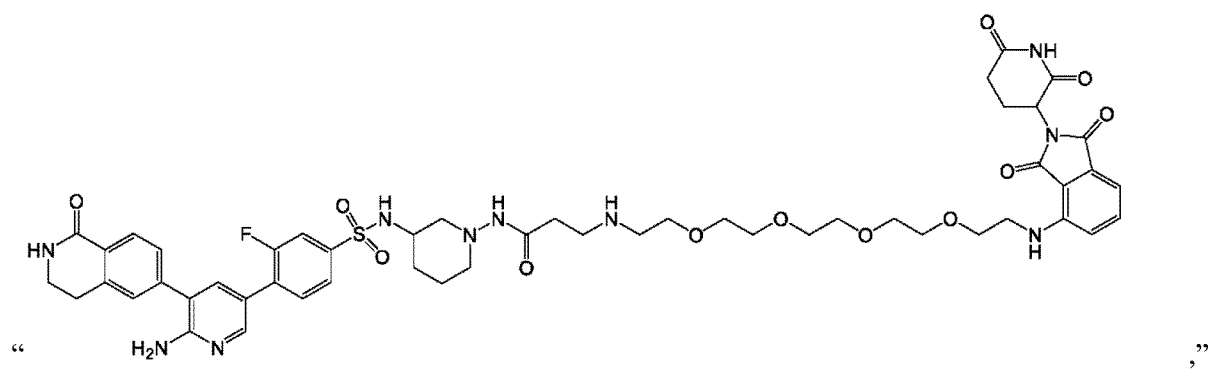

Replace with the following structure:

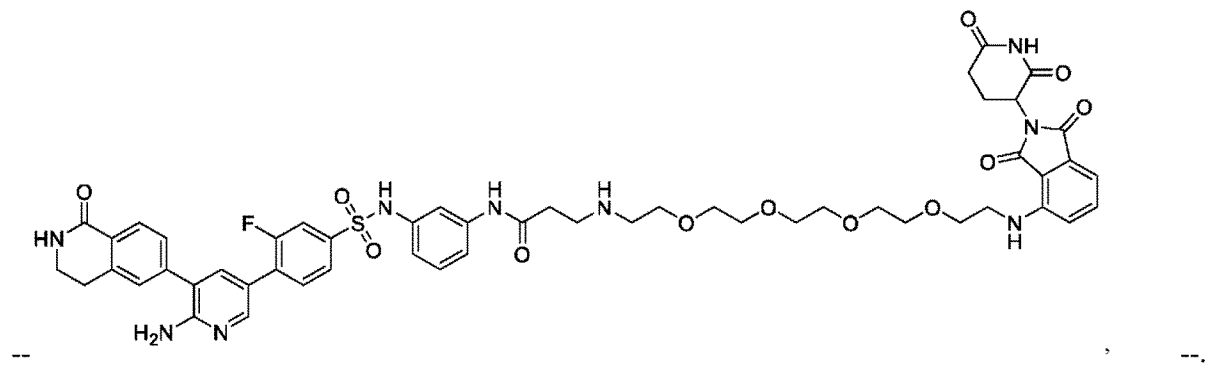

Signed and Sealed this  
Twenty-ninth Day of November, 2022

Katherine Kelly Vidal  
*Director of the United States Patent and Trademark Office*